US008598409B2

(12) United States Patent
Kapitskaya et al.

(10) Patent No.: US 8,598,409 B2
(45) Date of Patent: Dec. 3, 2013

(54) NON-HUMAN ORGANISM COMPRISING A GENE EXPRESSION MODULATION SYSTEM ENCODING A CHIMERIC RETINOID X RECEPTOR

(75) Inventors: Marianna Zinovievna Kapitskaya, North Wales, PA (US); Subba Reddy Palli, Lansdale, PA (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 11/841,648

(22) Filed: Aug. 24, 2007

(65) Prior Publication Data

US 2008/0263687 A1 Oct. 23, 2008

Related U.S. Application Data

(63) Continuation of application No. 10/468,199, filed as application No. PCT/US02/05706 on Feb. 20, 2002, now Pat. No. 7,531,326.

(60) Provisional application No. 60/269,799, filed on Feb. 20, 2001, provisional application No. 60/294,819, filed on May 31, 2001, provisional application No. 60/269,814, filed on May 31, 2001.

(51) Int. Cl.
*A01K 67/00* (2006.01)
*A01K 67/033* (2006.01)
*A01K 67/027* (2006.01)

(52) U.S. Cl.
USPC ........ 800/8; 800/13; 800/14; 800/15; 800/16; 800/17; 800/18; 800/19; 800/20

(58) Field of Classification Search
USPC ...................... 800/8–20, 21; 435/325; 514/44
See application file for complete search history.

(56) References Cited

U.S. PATENT DOCUMENTS 4,631,211 A 12/1986 Houghten
4,859,609 A 8/1989 Dull et al.
4,954,655 A 9/1990 Kelly
4,981,784 A 1/1991 Evans et al.
4,985,461 A 1/1991 Hsu et al.
5,010,175 A 4/1991 Rutter et al.
5,071,773 A 12/1991 Evans et al.
5,117,057 A 5/1992 Hsu et al.
5,171,671 A 12/1992 Evans et al.
5,225,443 A 7/1993 Murphy et al.
5,283,173 A 2/1994 Fields et al.
5,378,726 A 1/1995 Yanagi et al.
5,424,333 A 6/1995 Wing
5,429,952 A 7/1995 Garner et al.
5,459,127 A 10/1995 Felgner et al.
5,514,578 A 5/1996 Hogness et al.
5,530,021 A 6/1996 Yanagi et al.
5,530,028 A 6/1996 Lidert et al.
5,599,904 A 2/1997 Evans et al.
5,639,616 A 6/1997 Liao et al.
5,641,652 A 6/1997 Oro et al.
5,668,175 A 9/1997 Evans et al.
5,688,691 A 11/1997 Oro et al.
5,710,004 A 1/1998 Evans et al.
5,723,329 A 3/1998 Mangelsdorf et al.
5,789,214 A 8/1998 Ryals et al.
5,880,333 A 3/1999 Goff et al.
5,891,698 A 4/1999 Prieto et al.
5,919,667 A 7/1999 Gage et al.
5,939,442 A 8/1999 Evans et al.
5,989,863 A 11/1999 Tang et al.
6,004,941 A 12/1999 Bujard et al.
6,013,836 A 1/2000 Hsu et al.
6,025,483 A 2/2000 Yanofsky
6,096,787 A 8/2000 Evans et al.
6,107,543 A 8/2000 Sims et al.
6,117,639 A 9/2000 Germann et al.
6,147,276 A 11/2000 Campbell et al.
6,147,282 A 11/2000 Goff et al.
6,166,288 A 12/2000 Diamond et al.
6,214,620 B1 4/2001 Johns et al.
6,235,969 B1 5/2001 Stice et al.
6,245,531 B1 6/2001 Hogness et al.
6,258,603 B1 7/2001 Carlson et al.
6,265,173 B1 7/2001 Evans et al.
6,281,330 B1 8/2001 Evans et al.

(Continued)

FOREIGN PATENT DOCUMENTS

EP 0 729 975 A1 9/1996
EP 0 798 378 A2 10/1997

(Continued)

OTHER PUBLICATIONS

Hoppe (2000. Molecular Therapy 1:159-164.*
Saez (PNAS, 2000, vol. 97, p. 14512-14517).*
Andrianov, V.G., et al., "4-Amino-2-1,2,4-oxadiazolines," *Chemistry of Heterocyclic Compounds 27*:216-218, Spring New York (1991).
Andrianov, V.G., et al., "4-Aminofurazan-3-hydroximic halides," *Chemistry of Heterocyclic Compounds 28*:581-55, Springer-Verlag (1992).
Antoniewski, C., et al., "The ecdysone response enhancer of the Fbpl gene of *Drosophila melanogaster* is a direct target for the Ecr/USP nuclear receptor," *Mol. Cell. Biol. 14*:4465-4474, American Society for Microbiology (1994).

(Continued)

*Primary Examiner* — Michael C. Wilson
(74) *Attorney, Agent, or Firm* — Sterne, Kessler, Goldstein & Fox P.L.L.C.

(57) ABSTRACT

This invention relates to the field of biotechnology or genetic engineering. Specifically, this invention relates to the field of gene expression. More specifically, this invention relates to a novel ecdysone receptor/chimeric retinoid X receptor-based inducible gene expression system and methods of modulating gene expression in a host cell for applications such as gene therapy, large-scale production of proteins and antibodies, cell-based high throughput screening assays, functional genomics and regulation of traits in transgenic organisms.

36 Claims, 9 Drawing Sheets

(56) References Cited

U.S. PATENT DOCUMENTS

| | | | |
|---|---|---|---|
| 6,300,488 | B1 | 10/2001 | Gage et al. |
| 6,326,166 | B1 | 12/2001 | Pomerantz et al. |
| 6,333,318 | B1 | 12/2001 | Evans et al. |
| 6,379,945 | B1 | 4/2002 | Jepson et al. |
| 6,410,245 | B1 | 6/2002 | Northrop et al. |
| 6,458,926 | B1 | 10/2002 | Evans et al. |
| 6,504,082 | B1 | 1/2003 | Albertsen et al. |
| 6,635,429 | B1 | 10/2003 | Leid et al. |
| 6,723,531 | B2 | 4/2004 | Evans et al. |
| 6,756,491 | B2 | 6/2004 | Evans et al. |
| 6,875,569 | B2 | 4/2005 | Gage et al. |
| 6,939,711 | B2 | 9/2005 | Goff et al. |
| 7,038,022 | B1 | 5/2006 | Evans et al. |
| 7,045,315 | B2 | 5/2006 | Evans et al. |
| 7,057,015 | B1 | 6/2006 | Gage et al. |
| 7,091,038 | B2 | 8/2006 | Palli et al. |
| 7,119,077 | B1 | 10/2006 | Evans et al. |
| 7,183,061 | B2 | 2/2007 | Jepson et al. |
| 7,456,315 | B2 | 11/2008 | Hormann et al. |
| 7,531,326 | B2 | 5/2009 | Kapitskaya et al. |
| 7,776,587 | B2 | 8/2010 | Palli et al. |
| 7,807,417 | B2 | 10/2010 | Palli et al. |
| 7,935,510 | B2 | 5/2011 | Palli et al. |
| 8,076,454 | B2 | 12/2011 | Palli et al. |
| 8,105,825 | B2 | 1/2012 | Dhadialla et al. |
| 8,115,059 | B1 | 2/2012 | Palli et al. |
| 8,168,426 | B2 | 5/2012 | Dhadialla et al. |
| 8,202,718 | B2 | 6/2012 | Palli et al. |
| 8,236,556 | B2 | 8/2012 | Kapitskaya et al. |
| 2002/0110861 | A1 | 8/2002 | Dhadialla et al. |
| 2002/0119521 | A1 | 8/2002 | Palli et al. |
| 2004/0033600 | A1 | 2/2004 | Palli et al. |
| 2004/0096942 | A1 | 5/2004 | Palli et al. |
| 2004/0197861 | A1 | 10/2004 | Palli et al. |
| 2004/0235097 | A1 | 11/2004 | Zhang et al. |
| 2005/0266457 | A1 | 12/2005 | Palli et al. |
| 2006/0100416 | A1 | 5/2006 | Palli et al. |
| 2007/0161086 | A1 | 7/2007 | Palli et al. |
| 2007/0300313 | A1 | 12/2007 | Palli et al. |
| 2008/0064097 | A1 | 3/2008 | Palli et al. |
| 2008/0115237 | A1 | 5/2008 | Palli et al. |
| 2008/0145935 | A1 | 6/2008 | Palli et al. |
| 2008/0176280 | A1 | 7/2008 | Kapitskaya et al. |
| 2008/0216184 | A1 | 9/2008 | Palli et al. |
| 2008/0235816 | A1 | 9/2008 | Dhadialla et al. |
| 2008/0301825 | A1 | 12/2008 | Palli et al. |
| 2010/0275281 | A1 | 10/2010 | Dhadialla et al. |
| 2011/0059525 | A1 | 3/2011 | Palli et al. |
| 2011/0059530 | A1 | 3/2011 | Palli et al. |
| 2012/0185954 | A1 | 7/2012 | Palli et al. |
| 2012/0322148 | A1 | 12/2012 | Palli et al. |

FOREIGN PATENT DOCUMENTS

| | | | |
|---|---|---|---|
| EP | 0 965 644 | A2 | 12/1999 |
| EP | 1 266 601 | B1 | 12/2002 |
| WO | WO 89/12690 | A1 | 12/1989 |
| WO | WO 92/00252 | A1 | 1/1992 |
| WO | WO 94/28028 | A1 | 12/1994 |
| WO | WO 95/13373 | A1 | 5/1995 |
| WO | WO 95/18863 | A1 | 7/1995 |
| WO | WO 95/21931 | A1 | 8/1995 |
| WO | WO 96/05300 | A2 | 2/1996 |
| WO | WO 96/17823 | A1 | 6/1996 |
| WO | WO 96/21677 | A1 | 7/1996 |
| WO | WO 96/25508 | A1 | 8/1996 |
| WO | WO 96/27673 | A1 | 9/1996 |
| WO | WO 96/37609 | A1 | 11/1996 |
| WO | WO 97/35985 | A1 | 10/1997 |
| WO | WO 97/38117 | A1 | 10/1997 |
| WO | WO 98/33162 | A1 | 7/1998 |
| WO | WO 98/35550 | A2 | 8/1998 |
| WO | WO 99/02683 | A1 | 1/1999 |
| WO | WO 99/10510 | A2 | 3/1999 |
| WO | WO 99/26966 | A2 | 6/1999 |
| WO | WO 99/27365 | A1 | 6/1999 |
| WO | WO 99/36520 | A1 | 7/1999 |
| WO | WO 99/51777 | A2 | 10/1999 |
| WO | WO 99/58155 | A1 | 11/1999 |
| WO | WO 00/71743 | A1 | 11/2000 |
| WO | WO 01/02436 | A1 | 1/2001 |
| WO | WO 01/36447 | A1 | 5/2001 |
| WO | WO 01/62780 | A1 | 8/2001 |
| WO | WO 01/70816 | A2 | 9/2001 |
| WO | WO 02/66613 | A2 | 2/2002 |
| WO | WO 02/66614 | A2 | 2/2002 |
| WO | WO 02/66615 | A2 | 2/2002 |
| WO | WO 02/29075 | A2 | 4/2002 |
| WO | WO 02/066612 | A2 | 8/2002 |
| WO | WO 03/105849 | A1 | 12/2003 |
| WO | WO 2004/005478 | A2 | 1/2004 |
| WO | WO 2004/072254 | A2 | 8/2004 |
| WO | WO 2004/078924 | A2 | 9/2004 |
| WO | WO 2005/017126 | A2 | 2/2005 |
| WO | WO 2005/108617 | A2 | 11/2005 |
| WO | WO 2006/083253 | A1 | 8/2006 |

OTHER PUBLICATIONS

Ashburner, M., et al., "Temporal control of puffing activity in polytene chromosomes," *Cold Spring Harb. Symp. Quant. Biol. 38*:655-662, Cold Spring Harbor Laboratory Press (1974).

Belshaw, P.J., et al., "Controlling protein association and subcellular localization with synthetic ligand that induces heterodimerization of proteins," *Proc. Natl. Acad. Sci. U.S.A. 93*:4604-4607, National Academy of Science (1996).

Belshaw, P.J., et al., "Rational Design of Orthogonal Receptor-Ligand Combinations," *Angew. Chem. Int. Ed. Engl. 34*:2129-2132, Wiley-VCH (1995).

Bonneton, F., et al., "Rapid divergence of the ecdysone receptor in Diptera and Lepidoptera suggests coevolution between ECR and USP-RXR," *Mol. Biol. Evol. 20*:541-553, Oxford University Press (Mar. 2003).

Brennan, J.D., "Preparation and Entrapment of Fluorescently Labeled Proteins for the Development of Reagentless Optical Biosensor," *J. Fluorescence 9*:295-312, Kluwer Academic (1999).

Cao, S., et al., "N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis," *Canada. J. Chem. 79*:272-278, NRC Research Press (Mar. 2001).

Carlson, G.R., et al., "The chemical and biological properties of methoxyfenozide, a new insecticidal ecdysteroid agonist," *Pest Manag. Sci. 57*:115-119, Wiley (Jun. 2001).

Cherbas, L., et al., "Identification of ecdysone response elements by analysis of the Drosophila Eip28/29 gene," *Genes Dev. 5*:120-131, Cold Spring Harbor Laboratory Press (1991).

Cho, W.L., et al., "Mosquito ecdysteroid receptor: analysis of the cDNA and expression during vitellogenesis," *Insect. Biochem. Mol. Biol. 25*:19-27, Pergamon Press (1995).

Christopherson, K.S., et al., "Ecdysteroid-dependent regulation of genes in mammalian cells by a Drosophila ecdysone receptor and chimeric transactivators," *Proc. Natl. Acad. Sci. U.S.A. 89*:6314-6318, National Academy of Science (1992).

Chung, A.C., et al., "Cloning of crustacean ecdysteroid receptor and retinoid-X receptor gene homologs and elevation of retinoid-X receptor mRNA by retinoic acid," *Mol. Cell. Endocrinol. 139*:209-227, Elsevier Science (1998).

D'Avino, P.P., et al., "The moulting hormone ecdysone is able to recognize target elements composed of direct repeats," *Mol. Cell. Endocrinol. 113*:1-9, Elsevier Science (1995).

Dhadialla, T.S., et al., "New insecticides with ecdysteroidal and juvenile hormone activity," *Annu. Rev. Entomol. 43*:545-569, Annual Reviews (1998).

Doyle, D.F., et al., "Engineering orthogonal ligand-receptor pairs from near drugs," *J. Am. Chem. Soc. 123*:11367-11371, American Chemical Society (Oct. 2001).

(56) References Cited

OTHER PUBLICATIONS

Egea, P.F., et al., "Effects of ligand binding on the association properties and conformation in solution of retinoic acid receptors RXR and RAR," *Mol. Endocrinol. 16*:987-997, Endocrine Society (May 2002).

Evans, R.M., "The steroid and thyroid hormone receptor superfamily," *Science 240*:889-895, Association for the Advancement of Science (1988).

Fields, S., et al., "A novel genetic system to detect protein-protein interactions," *Nature 340*:245-246, Nature Publishing Group (1989).

Filmus, J., et al., "Synergistic induction of promoters containing metal- and glucocorticoid-responsive elements," *Nucleic Acids Res. 20*:2755-2760, Oxford University Press (1992).

Fujiwara, H., et al., "Cloning of an ecdysone receptor homolog from *Manduca sexta* and the development profile of its mRNA in wings," *Insect. Biochem. Mol. Biol. 25*:845-856, Pergamon Press (1995).

Glass, C.K., et al., "Nuclear receptor coactivators," *Curr. Opin. Cell. Biol. 9*:222-232, Current Science (1997).

Godowski, P.J., et al., "Signal transduction and transcriptional regulation by glucocorticoid receptor-LexA fusion proteins," *Science 241*:812-816, Association for the Advancement of Science (1988).

Guo, X., et al., "Isolation of a functional ecdysteroid receptor homologue from the ixodid tick *Amblyomma americanum* (L.)," *Insect Biochem. Mol. Biol. 27*:945-962, Pergamon Press (1997).

Hannan, G.N., et al., "Cloning and characterization of LcEcR: a functional ecdysone receptor from the sheep blowfly *Lucilia cuprina," Insect. Biochem. Mol. Biol. 27*:479-488, Pergamon Press (1997).

Hayward, D.C., et al., "The sequence of *Locusta* RXR, homologous to *Drosophila ultraspiracle*, and its evolutionary implications," *Dev. Genes Evol. 209*:564-571, Springer-Verlag (1999).

Hayward, D.C., et al., "The structure of the USP/RXR of *Xenos pecki* indicates that Strepsiptera are not closely related to Diptera," *Dev. Genes Evol. 215*:213-219, Springer-Verlag (Jan. 2005).

Heberlein, U., et al., "Characterization of *Drosophila* transcription factors that activate the tandem promoters of the alcohol dehydrogenase gene," *Cell 41*:965-977, Cell Press (1985).

Helmreich E.J.M., "The Biochemistry of Cell Signalling," p. 192, Oxford University Press (2001).

Hofmann, A., et al., "Rapid retroviral delivery of tetracycline-inducible genes in a single autoregulatory cassette," *Proc. Natl. Acad. Sci. 93*:5185-5190, National Academy of Science (1996).

Holt, J.R., et al., "Functional expression of exogenous proteins in mammalian sensory hair cells infected with adenoviral vectors," *J. Neurophysiol. 81*: 1881-1888, American Physiological Society (1999).

Hoppe, U.C., et al., "Adenovirus-Mediated Inducible Gene Expression in Vivo by a Hybrid Ecdysone Receptor," *Mol. Ther. 1*:159-164, Nature Publishing Group (Feb. 2000).

Horwitz, K.B., et al., "Nuclear receptor coactivators and corepressors," *Mol. Endocrinol. 10*:1167-1177, Endocrine Society (1996).

Imhof, M.O., et al., "Cloning of a *Chironomus tentans* cDNA encoding a protein (cEcRH) homologous to the *Drosophila melanogaster* ecdysteroid receptor (dEcR)," *Insect. Biochem. Mol. Biol. 23*:115-124, Pergamon Press (1993).

Kakizawa, T., et al., "Ligand-dependent heterodimerization of thyroid hormone receptor and retinoid X Receptor," *J. Biol. Chem. 272*:23799-23804, American Society for Biochemistry and Molecular Biology (1997).

Kim, J.S., et al., "Design of TATA box-binding protein/zinc finger fusions for targeted regulation of gene expression," *Proc Natl Acad Sci USA 94*:3616-3620, National Academy of Sciences (1997).

Kirken, R.A., et al., "Two discrete regions of interleukin-2 (IL2) receptor beta independently mediate IL2 activations of a PD98059/rapamycin/wortmannin-insensitive Stat5a/b serine kinase," *J. Biol. Chem. 272*:15459-15465, American Society for Biochemistry and Molecular Biology (1997).

Koelle, M.R., et al., "The *Drosophila* EcR gene encodes and ecdysone receptor, a new member of the steroid receptor superfamily," *Cell 67*:59-77, Cell Press (1991).

Kothapalli, R., et al., "Cloning and Developmental Expression of the Ecdysone Receptor Gene From the Spruce Budworm, *Choristoneura fumiferana," Dev. Genet. 17*:319-330, Wiley-Liss (1995).

Leid, M., et al., "Purification, cloning, and RXR identity of the HeLa cell factor with which RAR to TR heterodimerizes to bind target sequences efficiently," *Cell 68*:377-395, Cell Press (1992).

Leonhardt, S.A., et al., "Agonist and antagonists induce homodimerization and mixed ligand heterodimerization of human progesterone receptors in vivo by a mammalian two-hybrid assay," *Mol. Endocrinol. 12*:1914-1930, Endocrine Society (1998).

Licitra, E.J., et al., "A three-hybrid system for detecting small ligand-protein receptor interactions," *Proc. Natl. Acad. Sci. U.S.A. 93*:12817-12821, National Academy of Science (1996).

Martinez, A., et al., "Creation of ecdysone receptor chimeras in plants for controlled regulation of gene expression," *Mol. Gen. Genet. 261*:546-552, Springer-Verlag (1999).

Martinez, A., et al., "Transcriptional activation of the closed *Heliothis virescens* (Lepidoptera) ecdysone receptor (HvEcR) by muristeroneA," *Insect. Biochem. Mol. Biol. 29*:915-930, Pergamon Press (1999).

Metzger, D., et al., "The human estrogen receptor functions in yeast," *Nature 334*:31-36, Nature Publishing Group (1988).

Moradpour, D., et al., "Independent regulation of two separate gene activities in a continuous human cell line," *Biol. Chem. 379*:1189-1191, Walter De Gruyter (1998).

Morrison, D.A., et al., "Isolation of transformation-deficient *Streptococcus pneumoniae* mutants defective in control of competence, using insertion-duplication mutagenesis with erythromycin resistance determinant of pAM beta 1," *J. Bacteriol 159*:870-876, American Society for Microbiology (1984).

Mouillet, J.F., et al., "Cloning of two putative ecdysteroid receptor isoforms from Tenebrio molitor and their developmental expression in the epidermis during metamorphosis," *Eur. J. Biochem. 248*:856-863, Blackwell Science (1997).

Nakagawa, Y., et al., "Quantitative structure-activity studies of insect growth regulators: XIX: Effects of substituents on the aromatic moiety of dibenzoylhydrazines on larvicidal activity against the beet armyworm *Spodoptera exigua," Pest Manag. Sci. 58*:131-138, Wiley (Feb. 2002).

Neuberger, M.S., "Recombinant antibodies possessing novel effector functions," *Nature 312*:604-608, Nature Publishing Group (1984).

No, D., et al., "Ecdysone-inducible gene expression in mammalian cells and transgenic mice," *Proc. Natl. Acad. Sci. U.S.A. 93*:3346-3351, National Academy of Science (1996).

O'Brien, R.M., et al., "Structural and functional analysis of the human phosphoenolpyruvate carboxykinase gene promoter," *Biochim. Biophys. Acta 1264*:284-288, Elsevier Pub. Co. (1995).

Peet, D.J., et al., "Engineering novel specificities for ligand-activated transcription in the nuclear hormone receptor RXR," *Chem. Biol. 5*:13-21, Current Biology Ltd. (1998).

Perera, S.C., et al., "An Analysis of Ecdysone Receptor Domains Required for Heterodimerization With Ultraspiracle," *Archives of Insect Biochemistry and Physiology 41*: 61-70, Wiley-Liss, Inc. (1999).

Perera, S.C., et al., "Studies on two ecdysone receptor isoforms of the spruce budworm, *Choristoneura fumiferana," Mol. Cell. Endocrinol. 152*:73-84, North Holland Publishing (1999).

Pierce, A.C., et al., "Computational binding Studies of Orthogonal Cyclosporin-Cyclophilin Pairs," *Angew. Chem. Int. Ed. Engl. 36*:1466-1469, Wiley-VCH (1997).

Riddiford, L.M., et al., "Ecdysone receptors and their biological actions," *Vitam. Horm. 60*:1-73, Academic Press (Jan. 2000).

Saleh, D.S., et al., "Cloning and characterization of an ecdysone receptor cDNA from *Locusta migratoria," Mol. Cell. Endocrinol. 143*:91-99, Elsevier Science (1998).

Shea, C., et al., "An rxr/usp homolog from the parasitic nematode, *Dirofilaria immitis," Gene 324*:171-182, Elsevier/North-Holland (Nov. 2003).

Shimizu, B-i. et al., "Molting hormonal and larvicidal activities of aliphatic acyl analogs of dibenzoylhydrazine insecticides," *Steroids 62*:638-642, Elsevier Science Inc. (1997).

Spencer, D.M., et al., "Controlling signal transduction with synthetic ligands," *Science 262*:1019-1024, Association for the Advancement of Science (1993).

Srini, C., et al., "An analysis of ecdysone receptor domains required for heterodimerization with ultraspiracle," *Arch. Insect Biochem. Physiol. 41*:61-70, Wiley-Liss (1999).

(56) References Cited

OTHER PUBLICATIONS

Suhr, S.T., et al., "High level transactivation by a modified Bombyx ecdysone receptor in mammalian cells without exogenous retinoid X Receptor," *Proc. Natl. Acad. Sci. U.S.A. 95*:7999-8004, National Academy of Sciences (1998).
Swervers, L., et al., "The silkmoth homolog of the *Drosophila* ecdysone receptor (B1 isoform): cloning and analysis of expression during follicular cell differentiation," *Insect. Biochem. Mol. Biol. 25*:857-866, Elsevier (1995).
Talbot, W.S., et al., "*Drosophila* Tissues with Different Metamorphic Responses to Ecdysone Express Different Ecdysone Receptor Isoforms," *Cell 73*:1323-1337, Cell Press (1993).
Trisyono, A., et al., "Effect of the nonsteroidal ecdysone agonists, methoxyfenozide and tebufenozide, on the European Corn Borer (*Lepidoptera: Pyralidae*)," *J. Economic Entomology 90*:1486-1492, Entomological Society of America (1997).
Verras, M., et al., "Cloning and characterization of CcEcR. An ecdysone receptor homolog from the Mediterranean fruit fly ceratitis capitata," *Eur. J. Biochem. 265*:798-808, Blackwell Science (1999).
Wilson, J.M., et al., "Hepatocyte-directed gene transfer in vivo leads to transient improvement of hypercholesterolemia in low density lipoprotein receptor-deficient rabbits," *J Biol Chem 267*:963-967, American Society for Biochemistry and Molecular Biology (1992).
Wing, K.D., "RH 5849, a nonsteroidal ecdysone agonist: effects on a *Drosophila* cell line," Science 241:467-469, Association for the Advancement of Science (1988).
Wurm, F.M., et al., "Inducible overproduction of the mouse c-myc protein in mammalian cells," *Proc. Natl. Acad. Sci. U.S.A. 83*:5414-5418, National Academy of Science (1986).
Yao, T.P., et al., "*Drosophila* ultraspiracle modulates ecdysone receptor function via heterodimer formation," *Cell 71*:63-72, Cell Press (1992).
Yao, T.P., et al., "Functional ecdysone receptor is the product of EcR and Ultraspiracle genes," *Nature 366*:476-479, Nature Publishing Group (1993).
Zhang, X., et al., "Study on synthesis and bioactivity of new diacylhydrazine IGR JS118," Abstract, *Nongyao 42*:18-20, Editorial Office of Agrochemicals (2003).
UniProtKB/Swiss-Protein Database, Accession No. P49880, "Ecdysone receptor," 2 pages (1996).
UniProtKB/Swiss-Protein Database, Accession No. P49883, "Ecdysone receptor," 2 pages (1996).
Examiner's SCORE Search Results for U.S. Appl. No. 11/118,855, inventors Palli, et al., filed Apr. 29, 2005, 17 pages (conducted on Aug. 14, 2007).
Examiner's SCORE Search Results for U.S. Appl. No. 11/118,855, inventors Palli, et al., filed Apr. 29, 2005, 27 pages (conducted on Aug. 14, 2007).
Office Action mailed Jun. 13, 2005 in U.S. Appl. No. 09/965,703, inventors Palli, et al., filed Sep. 26, 2001.
Office Action mailed Nov. 24, 2004 in U.S. Appl. No. 09/965,703, inventors Palli, et al., filed Sep. 26, 2001.
Office Action mailed May 14, 2004 in U.S. Appl. No. 09/965,703, inventors Palli, et al., filed Sep. 26, 2001.
Office Action mailed Sep. 19, 2007 in U.S. Appl. No. 10/468,193, inventors Palli, et al., filed Dec. 17, 2003.
Office Action delivered electronically Mar. 13, 2008 in U.S. Appl. No. 10/468,199, inventors Kapitskaya, et al., filed Dec. 17, 2003.
Office Action mailed Oct. 26, 2006 in U.S. Appl. No. 10/468,199, inventors Kapitskaya, et al., filed Dec. 17, 2003.
Office Action mailed Jun. 11, 2007 in U.S. Appl. No. 10/468,199, inventors Kapitskaya, et al., filed Dec. 17, 2003.
Office Action mailed Sep. 7, 2007 in U.S. Appl. No. 11/118,855, inventors Palli, et al., filed Apr. 29, 2005.
Office Action delivered electronically Aug. 21, 2008 in U.S. Appl. No. 11/677,968, inventors Palli, et al., filed Feb. 22, 2007.
Office Action mailed Jul. 12, 2005 in U.S. Appl. No. 09/965,697, inventors Dhadialla, et al., filed Sep. 27, 2001.
Office Action mailed Apr. 18, 2006 in U.S. Appl. No. 09/965,697, inventors Dhadialla, et al., filed Sep. 27, 2001.
Office Action mailed Nov. 13, 2006 in U.S. Appl. No. 09/965,697, inventors Dhadialla, et al., filed Sep. 27, 2001.
Office Action mailed Aug. 9, 2007 in U.S. Appl. No. 09/965,697, inventors Dhadialla, et al., filed Sep. 27, 2001.
Office Action mailed May 28, 2008 in U.S. Appl. No. 09/965,697, inventors Dhadialla, et al., filed Sep. 27, 2001.
U.S. Appl. No. 10/468,200, inventors Palli, et al., filed Aug. 15, 2003.
U.S. Appl. No. 10/468,192, inventors Palli, et al., filed Aug. 15, 2003.
Blumberg, B., et al., "Multiple retinoid-responsive receptors in a single cell: Families of retinoid "X" receptors and retinoic acid receptors in the *Xenopous* egg," *Proc. Natl. Acad. Sci. USA 89*:2321-2325, National Academy of Sciences, United States (1992).
Clayton, G.M., et al., "The structure of the ultraspiracle ligand-binding domain reveals a nuclear receptor locked in an inactive conformation," *Proc. Natl. Acad. Sci. 98*:1549-1554, National Academy of Sciences, United States (2001).
EMBL Nucleotide Sequence Database, Accession No. AJ251542, "Tenebrio molitor mRNA for USP protein," 7 pages (Feb. 15, 2000).
Laudet, V., et al., "A Unified Nomenclature System for the Nuclear Receptor Superfamily," *Cell 97*:161-163, Cell Press, United States (1999).
Mangelsdorf, D.J., et al., "Nuclear receptor that identifies a novel retinoic acid response pathway," *Nature 345*:224-229, Nature Publishing Group, England (1990).
Marklew, S., et al., "Isolation of a novel RXR from Xenopus that most closely resembles mammalian RXRβ and is expressed throughout early development," *Biochim Biophys Acta 1218*:267-272, Elsevier Science B.V., Netherlands (1994).
Palmer, M.J., et al., "Characterization of EcR and RXR Homologous in the Ixodid Tick, *Amblyomma americanum* (L.)," *Am. Zool. 39*:747-757, American Society of Zoologists, United States (1999).
UniProtKB/Swiss-Protein Database, Accession No. O02035, "Ecdysone receptor," 6 pages (1997).
UniProtKB/Swiss-Protein Database, Accession No. O76246, "Ecdysteroid receptor," 6 pages (1998).
Office action mailed Jun. 30, 2009 in U.S. Appl. No. 11/118,855, inventors Palli et al., filed Apr. 29, 2005.
Office Action mailed Aug. 22, 2006 in U.S. Appl. No. 10/239,134, inventors Palli et al., filed Sep. 19, 2002.
Office Action mailed Feb. 20, 2009 in U.S. Appl. No. 11/677,968, inventors Palli et al., filed Feb. 22, 2007.
Office Action mailed Jun. 29, 2009 in U.S. Appl. No. 11/841,648, inventors Kapitskaya et al., filed Aug. 24, 2007.
Office Action mailed Feb. 24, 2009 in U.S. Appl. No. 11/841,495, inventors Palli et al., filed Aug. 20, 2007.
Office Action mailed Apr. 2, 2009 in U.S. Appl. No. 11/841,529, inventors Palli et al., filed Aug. 20, 2007.
Office Action mailed Oct. 21, 2009 in U.S. Appl. No. 11/841,597, inventors Kapitskaya et al., filed Aug. 20, 2007.
Office Action mailed Dec. 9, 2008 in U.S. Appl. No. 09/965,697, inventors Dhadialla, et al., filed Sep. 27, 2001.
Office Action mailed Jun. 23, 2009 in U.S. Appl. No. 09/965,697, inventors Dhadialla et al., filed Sep. 27, 2001.
Office Action mailed Feb. 25, 2009 in U.S. Appl. No. 11/841,325, inventors Dhadialla et al., filed Aug. 20, 2007.
Office Action mailed May 22, 2009 in U.S. Appl. No. 11/837,834, inventors Palli et al., filed Aug. 13, 2007.
Office Action mailed May 12, 2010 in U.S. Appl. No. 11/841,464, inventors Palli et al., filed Aug. 20, 2007.
Notice of Allowance mailed May 24, 2010 in U.S. Appl. No. 11/677,968, inventors Palli et al., filed Feb. 22, 2007.
Office Action mailed Sep. 14, 2010 in U.S. Appl. No. 11/841,644, inventors Palli et al., filed Aug. 20, 2007.
Office Action mailed Nov. 10, 2010 in U.S. Appl. No. 11/841,597, inventors Kapitskaya et al., filed Aug. 20, 2007.
Office Action mailed May 25, 2010 in U.S. Appl. No. 09/965,697, inventors Dhadialla et al., filed Sep. 27, 2001.
Kumar, M.B., "A single point mutation in ecdysone receptor leads to increased ligand specificity: Implications for gene switch applications," *Proc. Natl. Acad. Sci. 99*: 14710-14715, National Academy of Sciences, United States (2002).

(56) References Cited

OTHER PUBLICATIONS

Palli, S.R. et al., "Improved ecdysone receptor-based inducible gene regulation system," *Eur. J. Biochem. 270*: 1308-1315, Wiley Interscience (2003).
Tran, H.T. et al., "Reconstruction of Ligand-Dependent Transactivation of *Choristoneura fumiferana* Ecdysone Receptor in Yeast," *Molecular Endocrinology 15*: 1140-1153, The Endocrine Society (2001).
U.S. Appl. No. 12/818,034, filed Jun. 17, 2010, inventors Palli et al.
U.S. Appl. No. 12/859,940, filed Aug. 20, 2010, inventors Palli et al.
U.S. Appl. No. 12/707,599, filed Feb. 17, 2010, inventors Dhadialla et al.
Notice of Allowance mailed Feb. 4, 2010 in U.S. Appl. No. 11/118,855, inventors Palli et al., filed Apr. 29, 2005.
Office Action mailed Feb. 18, 2010 in U.S. Appl. No. 10/468,193, inventors Palli et al., filed Dec. 17, 2003.
Office action mailed Feb. 22, 2010 in U.S. Appl. No. 11/837,834, inventors Palli et al., filed Aug. 13, 2007.
Notice of Allowance mailed Mar. 19, 2010 in U.S. Appl. No. 11/841,495, inventors Palli et al., filed Aug. 20, 2007.
Office Action mailed Apr. 1, 2010 in U.S. Appl. No. 11/841,529, inventors Palli et al., filed Aug. 20, 2007.
Office action mailed Nov. 3, 2011 in U.S. Appl. No. 11/841,597, inventors Kapitskaya et al., filed Aug. 20, 2007.
Office action mailed Oct. 18, 2011 in U.S. Appl. No. 12/818,034, inventors Palli et al., filed Feb. 17, 2010.
Notice of Allowance mailed Feb. 6, 2012 in U.S. Appl. No. 12/818,034, inventors Palli et al., filed Feb. 17, 2010.
Office action mailed Jul. 20, 2011 in U.S. Appl. No. 12/707,599, inventors Dhadialla et al., filed Feb. 17, 2010.
Office action mailed Apr. 20, 2010 in U.S. Appl. No. 11/841,597, inventors Kapitskaya et al., filed Aug. 20, 2007.
Office Action mailed Feb. 14, 2012 in U.S. Appl. No. 11/841,644, inventors Palli et al., filed Aug. 20, 2007.
Office Action mailed Jun. 21, 2011 in U.S. Appl. No. 10/468,193, inventors Palli et al., filed Dec. 17, 2003.
Office Action mailed May 10, 2012 in U.S. Appl. No. 10/468,193, inventors Palli et al., filed Dec. 17, 2003.
Office Action mailed Jul. 27, 2012 in U.S. Appl. No. 12/859,940, inventors Palli et al., filed Aug. 20, 2010.
Bilger, M., et al., "A Conditional Tetracycline-Regulated Increase in Gamma Amino Butyric Acid Production Near Luteinizing Hormone-Releasing Hormone Nerve Terminals Disrupts Estrous Cyclicity in the Rat," *Endocrinology 142*(5):2102-2114, The Endocrine Society, United States (2001).
Campbell, K.H.S., et al., "Sheep cloned by nuclear transfer from a cultured cell line," *Nature 380*:64-66, Nature Publishing Group, England (1996).
Carver, A.S., et al., "Transgenic Livestock as Bioreactors: Stable Expression of Human Alpha-l-Antitrypsin by a Flock of Sheep," *Bio/Technology 11*:1263-1270, Nature Publishing Company, United States (1993).
Chiou, T.-J. and Bush, D.R., "Molecular Cloning, Immunochemical Localization to the Vacuole, and Expression in Transgenic Yeast and Tobacco of a Putative Sugar Transporter from Sugar Beet," *Plant Physiol. 110*: 511-520, American Society of Plant Physiologists, United States (1996).
Du, S.J., et al., "Growth Enhancement in Transgenic Atlantic Salmon by the Use of an 'All Fish' Chimeric Growth Hormone Gene Construct," *Bio/Technology 10*:176-181, Nature Publishing Company, United States (1992).
Durvasula, R.V., et al., "Prevention of insect-borne disease: An approach using transgenic symbiotic bacteria," *PNAS USA 94*: 3274-3278, The National Academy of Sciences of the USA, United States (1997).
Love, J., et al., "Transgenic Birds by DNA Microinjection," *Bio/Technology 12*:60-63 Nature Publishing Company, United States (1994).
McCreath, K.J., et al., "Production of gene-targeted sheep by nuclear transfer from cultured somatic cells," *Nature 405*:1066-1069, *Nature 408*:120, and Nature Ref. N0614E KIND (ERR), 6 Pages, Macmillan Magazines Ltd, England (2000).
Pursel, V.G., et al., "Transfer of an Ovine Metallothionein-Ovine Growth Hormone Fusion Gene into Swine," *J Anim. Sci. 75*:2208-2214, American Society of Animal Science, United States (1997).
Schnieke, A.E., et al., "Human Factor IX Transgenic Sheep Produced by Transfer of Nuclei from Transfected Fetal Fibroblasts," *Science 278*:2130-2133, American Association for the Advancement of Science, United States (1997).
Wall, R.J., et al., "Transgenic Dairy Cattle: Genetic Engineering on a Large Scale," *J. Dairy Sci. 80*:2213-2224, American Dairy Science Association, United States (1997).
Wilmut, I., et al., "Viable offspring derived from fetal and adult mammalian cells," *Nature 385*:810-813 and *Nature 386*:200, 5 Pages, Nature Publishing Group, England (1997).
Wolf, E., et al., "Transgenic technology in farm animals—progress and perspectives," *Experimental Physiology 85*(6):615-625, The Physiological Society, England (2000).
Zuo, J., et al., An estrogen receptor-based transactivator XVE mediates highly inducible gene expression in transgenic plants, *The Plant Journal 24*(2):265-273, Blackwell Science Ltd, England (2000).
Gama Sosa, M.A., et al., "Animal transgenesis: an overview," *Brain Structure Function 214*:91-109, Springer (2010).
Griffiths, I., et al., "Current Concepts of PLP and Its Role in the Nervous System," *Microscopy Research and Technique 41*: 344-358, Wiley-Liss, Inc. (1998).
Melo, E.O., et al., "Animal transgenesis: state of the art and appliations," *J. Appl. Genet.48*: 47-61, Springer (2007).
Qi, N.R., et al., "A New Transgneic Rat Model of Hepatic Steatosis an the Metabolic Syndrome," *Hypertension 45*: 1004-1011, American Heart Association, Inc. (2005).
Ristevski, S., Making Better Transgenic Models, *Molecular Biotechnology 29*: 153-163, Humana Press, Inc. (2005).
Smith, K.R., "Gene transfer in higher animals: theoretical considerations and key concepts," *J. Biotechnology 99*: 1-22, Elsevier Science B.V., The Netherlands (2002).
Office Action mailed Sep. 5, 2012 in U.S. Appl. No. 13/289,127, inventors Palli et al., filed Nov. 4, 2011.
Office Action mailed Apr. 16, 2013 in U.S. Appl. No. 13/289,127, inventors Palli et al., filed Nov. 4, 2011.
U.S. Appl. No. 13/615,348, inventors Palli et al., filed Sep. 13, 2012.
U.S. Appl. No. 13/618,693, inventors Palli et al., filed Sep. 13, 2012.
U.S. Appl. No. 13/618,742, inventors Kapitskaya et al., filed Sep. 14, 2012.
U.S. Appl. No. 13/431,636, inventors Dhadialla et al., filed Mar. 27, 2012.
U.S. Appl. No. 13/613,597, inventors Dhadialla et al., filed Sep. 13, 2012.
Teboul, M. et al., "OR-1, a member of the nuclear receptor superfamily that interacts with the 9-*cis*-retinoic acid receptor," *Proc. Natl. Acad. Sci. USA 92*; 2096-2100, National Academy of Sciences, Washington, D.C., U.S.A. (1995).
Notice of Allowance mailed Apr. 27, 2011 in U.S. Appl. No. 11/841,631, filed Aug. 20, 2007, inventors Palli et al.
Office Action mailed Mar. 30, 2011, in U.S. Appl. No. 12/818,034, filed Jun. 17, 2010, inventors Palli et al.
Office Action mailed Feb. 15, 2011 in U.S. Appl. No. 09/965,697, inventors Dhadialla, et al., filed Sep. 27, 2001.
Office Action mailed Sep. 14, 2010, in U.S. Appl. No. 11/837,834, filed Aug. 13, 2007, inventors Palli et al.
Notice of Allowance mailed Dec. 27, 2010 in U.S. Appl. No. 11/118,855, inventors Palli et al., filed Apr. 29, 2005.
Notice of Allowance mailed Apr. 27, 2011 in U.S. Appl. No. 11/841,631, inventors Palli et al., filed Aug. 20, 2007.
Office action mailed Dec. 30, 2010 in U.S. Appl. No. 12/707,599, inventors Dhadialla et al., filed Feb. 17, 2010.
Office Action mailed Sep. 28, 2010 in U.S. Appl. No. 11/841,631, inventors Palli et al., filed Aug. 20, 2007.

* cited by examiner

```
HsRXRbEF APEEMPVDRILEAELAVEQKSDQGVEGPGGTGGSGSSPNDPVTNICQAADKQLFTLVEWA 60
MmRXRbEF APEEMPVDRILEAELAVEQKSDQGVEGPGATGGGGSSPNDPVTNICQAADKQLFTLVEWA 60
HsRXRaEF ANEDMPVERILEAELAVEPKTETYVEAN--MGLNPSSPNDPVTNICQAADKQLFTLVEWA 58
MmRXRaEF ANEDMPVEKILEAELAVEPKTETYVEAN--MGLNPSSPNDPVTNICQAADKQLFTLVEWA 58
HsRXRgEF GHEDMPVERILEAELAVEPKTESYGDMN-----MENSTNDPVTNICHAADKQLFTLVEWA 55
MmRXRgEF SHEDMPVERILEAELAVEPKTESYGDMN-----VENSTNDPVTNICHAADKQLFTLVEWA 55
                  H1                                H3

                                                          B6
HsRXRbEF KRIPHFSSLPLDDQVILLRAGWNELLIASFSHRSIDVRDGILLATGLHVHRNSAHSAGVG 120
MmRXRbEF KRIPHFSSLPLDDQVILLRAGWNELLIASFSHRSIDVRDGILLATGLHVHRNSAHSAGVG 120
HsRXRaEF KRIPHFSELPLDDQVILLRAGWNELLIASFSHRSIAVKDGILLATGLHVHRNSAHSAGVG 118
MmRXRaEF KRIPHFSELPLDDQVILLRAGWNELLIASFSHRSIAVKDGILLATGLHVHRNSAHSAGVG 118
HsRXRgEF KRIPHFSDLTLEDQVILLRAGWNELLIASFSHRSVSVQDGILLATGLHVHRSSAHSAGVG 115
MmRXRgEF KRIPHFSDLTLEDQVILLRAGWNELLIASFSHRSVSVQDGILLATGLHVHRSSAHSRGVG 115
                  H4           H5          S1       S2    H6

                   B8A1                    B9
HsRXRbEF AIFDRVLTELVSKMRDMRMDKTELGCLRAIILFNPDAKGLSNPSEVEVLREKVYASLETY 180
MmRXRbEF AIFDRVLTELVSKMRDMRMDKTELGCLRAIIMFNPDAKGLSNPGEVEILREKVYASLETY 180
HsRXRaEF AIFDRVLTELVSKMRDMQMDKTELGCLRAIVLFNPDSKGLSNPAEVEALREKVYASLEAY 178
MmRXRaEF AIFDRVLTELVSKMRDMQMDKTELGCLRAIVLFNPDSKGLSNPAEVEALREKVYASLEAY 178
HsRXRgEF SIFDRVLTELVSKMKDMQMDKSELGCLRAIVLFNPDAKGLSNPSEVETLREKVYATLEAY 175
MmRXRgEF SIFDRVLTELVSKMKDMQMDKSELGCLRAIVLFNPDAKGLSNPSEVETLREKVYATLEAY 175
             H7                 H8                     H9

              B10                    B11
HsRXRbEF CKQKYPEQQGRFAKLLLRLPALRSIGLKCLEHLFFFKLIGDTPIDTFLMEMLEAPHQLA 239
MmRXRbEF CKQKYPEQQGRFAKLLLRLPALRSIGLKCLEHLFFFKLIGDTPIDTFLMEMLEAPHQLA 239
HsRXRaEF CKHKYPEQPGRFAKLLLRLPALRSIGLKCLEHLFFFKLIGDTPIDTFLMEMLEAPHQMT 237
MmRXRaEF CKHKYPEQPGRFAKLLLRLPALRSIGLKCLEHLFFFKLIGDTPIDTFLMEMLEAPHQAT 237
HsRXRgEF TKQKYPEQPGRFAKLLLRLPALRSIGLKCLEHLFFFKLIGDTPIDTFLMEMLETPLQIT 234
MmRXRgEF TKQKYPEQPGRFAKLLLRLPALRSIGLKCLEHLFFFKLIGDTPIDSFLMEMLETPLQIT 234
                        H10           H11             H12     F
```

Figure 4A

```
LmRXREF   HTDMPVERILEAEKRVECKAENQ----------------------------------VEY 26
AmRXREF   HSDMPIERILEAEKRVECKMEQQ----------------------------------GNY 26
TmRXREF   -AEMPLDRIIEAEKRIECTPAGGSGG------------------------------VGEQ 29
CpRXREF   -SDMPIASIREAELSVDPIDEQPLDQGVRLQVPLAPPDSEKCSFTLPFHPVSEVSCANPL 59
AmaRXR1EF PPEMPLERILEAELRVES-QTGTLSES-----------------------------AQQ- 29
AmaRXR2EF SPDMPLERILEAEMRVEQPAPSVLAQT-----------------------------AASG 31
              H1

LmRXREF   E----------------LVEWAKHIPHFTSLPLEDQVLLLRAGWNELLIAAFSHRSVDVK 70
AmRXREF   ENAVSHICNATNKQLFQLVAWAKHIPHFTSLPLEDQVLLLRAGWNELLIASFSHRSIDVK 86
TmRXREF   HDGVNNICQATNKQLFQLVQWAKLIPHFTSLPMSDQVLLLRAGWNELLIAAFSHRSIQAQ 89
CpRXREF   QDVVSNICQAADRHLVQLVEWAKHIPHFTDLPIEDQVVLLKAGWNELLIASFSHRSMGVE 119
AmaRXR1EF QDPVSSICQAADRQLHQLVQWAKHIPHFEELPLEDRMVLLKAGWNELLIAAFSHRSVDVR 89
AmaRXR2EF RDPVNSMCQAAP-PLHELVQWARRIPHFEELPIEDRTALLKAGWNELLIAAFSHRSVAVR 90
                   H3                          H4          H5

                          B6                             B8 A1         B9
LmRXREF   DGIVLATGLTVHRNSAHQAGVGTIFDRVLTELVAKMREMKMDKTELGCLRSVILFNPEVR 130
AmRXREF   DGIVLATGITVHRNSAQQAGVGTIFDRVLSELVSKMREMKMDRTELGCLRSIILFNPEVR 146
TmRXREF   DAIVLATGLTVNKTSAHAVGVGNIYDRVLSELVNKMKEMKMDKTELGCLRAIILYNPTCR 149
CpRXREF   DGIVLATGLVIHRSSAHQAGVGAIFDRVLSELVAKMKEMKIDKTELGCLRSIVLFNPDAK 179
AmaRXR1EF DGIVLATGLVVQRHSAHGAGVGAIFDRVLTELVAKMREMKMDRTELGCLLAVVLFNPEAK 149
AmaRXR2EF DGIVLATGLVVQRHSAHGAGVGDIFDRVLAELVAKMRDMKMDKTELGCLRAVVLFNPDAK 150
            S1       S2   H6           H7                H8

                                          B10                    B11
LmRXREF   GLKSAQEVELLREKVYAALEEYTRTTHPDEPGRFAKLLLRLPSLRSIGLKCLEHLFFFRL 190
AmRXREF   GLKSIQEVTLLREKIYGALEGYCRVAWPDDAGRFAKLLLRLPAIRSIGLKCLEYLFFFKM 206
TmRXREF   GIKSVQEVEMLREKIYGVLEEYTRTTHPNEPGRFAKLLLRLPALRSIGLKCSEHLFFFKL 209
CpRXREF   GLNCVNDVEILREKVYAALEEYTRTTYPDEPGRFAKLLLRLPALRSIGLKCLEYLFLFKL 239
AmaRXR1EF GLRTCPSGGPEGESV-SALEEHCRQQYPDQPGRFAKLLLRLPALRSIGLKCLEHLFFFKL 208
AmaRXR2EF GLRNATRVEALREKVYAALEEHCRRHHPDQPGRFGKLLLRLPALRSIGLKCLEHLFFFKL 210
                     H9                                H10          H11

LmRXREF   IGDVPIDTFLMEMLESPSDS-------   210
AmRXREF   IGDVPIDDFLVEMLESRSDP-------   226
TmRXREF   IGDVPIDTFLMEMLESPADA------    229
CpRXREF   IGDTPLDSYLMKMLVDNPNTSVTPPTS   266
AmaRXR1EF IGDTPIDNFLLSMLEAPSDP-------   228
AmaRXR2EF IGDTPIDSFLLNMLEAPADP-------   230
                 H12   F
```

Figure 4B

SEQUENCE LISTING

```
<160> NUMBER OF SEQ ID NOS: 75

<210> SEQ ID NO 1
<211> LENGTH: 735
<212> TYPE: DNA
<213> ORGANISM: Choristoneura fumiferana

<400> SEQUENCE: 1

taccaggacg ggtacgagca gccttctgat gaagatttga agaggattac gcagacgtgg      60

cagcaagcgg acgatgaaaa cgaagagtct gacactccct tccgccagat cacagagatg     120

actatcctca cggtccaact tatcgtggag ttcgcgaagg gattgccagg gttcgccaag     180

atctcgcagc ctgatcaaat tacgctgctt aaggcttgct caagtgaggt aatgatgctc     240

cgagtcgcgc gacgatacga tgcggcctca gacagtgttc tgttcgcgaa caaccaagcg     300

tacactcgcg acaactaccg caaggctggc atggcctacg tcatcgagga tctactgcac     360

ttctgccggt gcatgtactc tatggcgttg gacaacatcc attacgcgct gctcacggct     420
```

```
gtcgtcatct tttctgaccg gccagggttg gagcagccgc aactggtgga agaaatccag    480

cggtactacc tgaatacgct ccgcatctat atcctgaacc agctgagcgg gtcggcgcgt    540

tcgtccgtca tatacggcaa gatcctctca atcctctctg agctacgcac gctcggcatg    600

caaaactcca acatgtgcat ctccctcaag ctcaagaaca gaaagctgcc gcctttcctc    660

gaggagatct gggatgtggc ggacatgtcg cacacccaac cgccgcctat cctcgagtcc    720

cccacgaatc tctag                                                     735
```

<210> SEQ ID NO 2
<211> LENGTH: 1338
<212> TYPE: DNA
<213> ORGANISM: Drosophila melanogaster

<400> SEQUENCE: 2

```
tatgagcagc catctgaaga ggatctcagg cgtataatga gtcaacccga tgagaacgag     60

agccaaacgg acgtcagctt tcggcatata accgagataa ccatactcac ggtccagttg    120

attgttgagt ttgctaaagg tctaccagcg tttacaaaga taccccagga ggaccagatc    180

acgttactaa aggcctgctc gtcggaggtg atgatgctgc gtatggcacg acgctatgac    240

cacagctcgg actcaatatt cttcgcgaat aatagatcat atacgcggga ttcttacaaa    300

atggccggaa tggctgataa cattgaagac ctgctgcatt tctgccgcca aatgttctcg    360

atgaaggtgg acaacgtcga atacgcgctt ctcactgcca ttgtgatctt ctcggaccgg    420

ccgggcctgg agaaggccca actagtcgaa gcgatccaga gctactacat cgacacgcta    480

cgcatttata tactcaaccg ccactgcggc gactcaatga gcctcgtctt ctacgcaaag    540

ctgctctcga tcctcaccga gctgcgtacg ctgggcaacc agaacgccga gatgtgtttc    600

tcactaaagc tcaaaaaccg caaactgccc aagttcctcg aggagatctg ggacgttcat    660

gccatcccgc catcggtcca gtcgcacctt cagattaccc aggaggagaa cgagcgtctc    720

gagcgggctg agcgtatgcg ggcatcggtt gggggcgcca ttaccgccgg cattgattgc    780

gactctgcct ccacttcggc ggcggcagcc gcggcccagc atcagcctca gcctcagccc    840

cagccccaac cctcctccct gacccagaac gattcccagc accagacaca gccgcagcta    900

caacctcagc taccacctca gctgcaaggt caactgcaac cccagctcca accacagctt    960

cagacgcaac tccagccaca gattcaacca cagccacagc tccttcccgt ctccgctccc   1020

gtgcccgcct ccgtaaccgc acctggttcc ttgtccgcgg tcagtacgag cagcgaatac   1080

atgggcggaa gtgcggccat aggacccatc acgccggcaa ccaccagcag tatcacggct   1140

gccgttaccg ctagctccac cacatcagcg gtaccgatgg gcaacggagt tggagtcggt   1200

gttggggtgg gcggcaacgt cagcatgtat gcgaacgccc agacggcgat ggccttgatg   1260

ggtgtagccc tgcattcgca ccaagagcag cttatcgggg gagtggcggt taagtcggag   1320

cactcgacga ctgcatag                                                 1338
```

<210> SEQ ID NO 3
<211> LENGTH: 960
<212> TYPE: DNA
<213> ORGANISM: Choristoneura fumiferana

<400> SEQUENCE: 3

```
cctgagtgcg tagtacccga gactcagtgc gccatgaagc ggaaagagaa gaaagcacag     60

aaggagaagg acaaactgcc tgtcagcacg acgacggtgg acgaccacat gccgcccatt    120

atgcagtgtg aacctccacc tcctgaagca gcaaggattc acgaagtggt cccaaggttt    180
```

```
ctctccgaca agctgttgga gacaaaccgg cagaaaaaca tcccccagtt gacagccaac    240

cagcagttcc ttatcgccag gctcatctgg taccaggacg ggtacgagca gccttctgat    300

gaagatttga agaggattac gcagacgtgg cagcaagcgg acgatgaaaa cgaagagtct    360

gacactccct tccgccagat cacagagatg actatcctca cggtccaact tatcgtggag    420

ttcgcgaagg gattgccagg gttcgccaag atctcgcagc ctgatcaaat tacgctgctt    480

aaggcttgct caagtgaggt aatgatgctc cgagtcgcgc gacgatacga tgcggcctca    540

gacagtgttc tgttcgcgaa caaccaagcg tacactcgcg acaactaccg caaggctggc    600

atggcctacg tcatcgagga tctactgcac ttctgccggt gcatgtactc tatggcgttg    660

gacaacatcc attacgcgct gctcacggct gtcgtcatct tttctgaccg gccagggttg    720

gagcagccgc aactggtgga agaaatccag cggtactacc tgaatacgct ccgcatctat    780

atcctgaacc agctgagcgg gtcggcgcgt tcgtccgtca tatacggcaa gatcctctca    840

atcctctctg agctacgcac gctcggcatg caaaactcca acatgtgcat ctccctcaag    900

ctcaagaaca gaaagctgcc gcctttcctc gaggagatct gggatgtggc ggacatgtcg    960
```

```
<210> SEQ ID NO 4
<211> LENGTH: 969
<212> TYPE: DNA
<213> ORGANISM: Drosophila melanogaster

<400> SEQUENCE: 4

cggccggaat gcgtcgtccc ggagaaccaa tgtgcgatga agcggcgcga aaagaaggcc     60

cagaaggaga aggacaaaat gaccacttcg ccgagctctc agcatggcgg caatggcagc    120

ttggcctctg gtggcggcca agactttgtt aagaaggaga ttcttgacct tatgacatgc    180

gagccgcccc agcatgccac tattccgcta ctacctgatg aaatattggc caagtgtcaa    240

gcgcgcaata taccttcctt aacgtacaat cagttggccg ttatatacaa gttaatttgg    300

taccaggatg gctatgagca gccatctgaa gaggatctca ggcgtataat gagtcaaccc    360

gatgagaacg agagccaaac ggacgtcagc tttcggcata taaccgagat aaccatactc    420

acggtccagt tgattgttga gtttgctaaa ggtctaccag cgtttacaaa gatacccccag   480

gaggaccaga tcacgttact aaaggcctgc tcgtcggagg tgatgatgct gcgtatggca    540

cgacgctatg accacagctc ggactcaata ttcttcgcga ataatagatc atatacgcgg    600

gattcttaca aaatggccgg aatggctgat aacattgaag acctgctgca tttctgccgc    660

caaatgttct cgatgaaggt ggacaacgtc gaatacgcgc ttctcactgc cattgtgatc    720

ttctcggacc ggccgggcct ggagaaggcc caactagtcg aagcgatcca gagctactac    780

atcgacacgc tacgcattta tatactcaac cgccactgcg gcgactcaat gagcctcgtc    840

ttctacgcaa agctgctctc gatcctcacc gagctgcgta cgctgggcaa ccagaacgcc    900

gagatgtgtt tctcactaaa gctcaaaaac cgcaaactgc ccaagttcct cgaggagatc    960

tgggacgtt                                                             969
```

```
<210> SEQ ID NO 5
<211> LENGTH: 244
<212> TYPE: PRT
<213> ORGANISM: Choristoneura fumiferana

<400> SEQUENCE: 5

Tyr Gln Asp Gly Tyr Glu Gln Pro Ser Asp Glu Asp Leu Lys Arg Ile
1               5                   10                  15
```

-continued

Thr Gln Thr Trp Gln Gln Ala Asp Asp Glu Asn Glu Glu Ser Asp Thr
20 25 30

Pro Phe Arg Gln Ile Thr Glu Met Thr Ile Leu Thr Val Gln Leu Ile
35 40 45

Val Glu Phe Ala Lys Gly Leu Pro Gly Phe Ala Lys Ile Ser Gln Pro
50 55 60

Asp Gln Ile Thr Leu Leu Lys Ala Cys Ser Ser Glu Val Met Met Leu
65 70 75 80

Arg Val Ala Arg Arg Tyr Asp Ala Ala Ser Asp Ser Val Leu Phe Ala
85 90 95

Asn Asn Gln Ala Tyr Thr Arg Asp Asn Tyr Arg Lys Ala Gly Met Ala
100 105 110

Tyr Val Ile Glu Asp Leu Leu His Phe Cys Arg Cys Met Tyr Ser Met
115 120 125

Ala Leu Asp Asn Ile His Tyr Ala Leu Leu Thr Ala Val Val Ile Phe
130 135 140

Ser Asp Arg Pro Gly Leu Glu Gln Pro Gln Leu Val Glu Glu Ile Gln
145 150 155 160

Arg Tyr Tyr Leu Asn Thr Leu Arg Ile Tyr Ile Leu Asn Gln Leu Ser
165 170 175

Gly Ser Ala Arg Ser Ser Val Ile Tyr Gly Lys Ile Leu Ser Ile Leu
180 185 190

Ser Glu Leu Arg Thr Leu Gly Met Gln Asn Ser Asn Met Cys Ile Ser
195 200 205

Leu Lys Leu Lys Asn Arg Lys Leu Pro Pro Phe Leu Glu Glu Ile Trp
210 215 220

Asp Val Ala Asp Met Ser His Thr Gln Pro Pro Pro Ile Leu Glu Ser
225 230 235 240

Pro Thr Asn Leu

<210> SEQ ID NO 6
<211> LENGTH: 445
<212> TYPE: PRT
<213> ORGANISM: Drosophila melanogaster

<400> SEQUENCE: 6

Tyr Glu Gln Pro Ser Glu Glu Asp Leu Arg Arg Ile Met Ser Gln Pro
1 5 10 15

Asp Glu Asn Glu Ser Gln Thr Asp Val Ser Phe Arg His Ile Thr Glu
20 25 30

Ile Thr Ile Leu Thr Val Gln Leu Ile Val Glu Phe Ala Lys Gly Leu
35 40 45

Pro Ala Phe Thr Lys Ile Pro Gln Glu Asp Gln Ile Thr Leu Leu Lys
50 55 60

Ala Cys Ser Ser Glu Val Met Met Leu Arg Met Ala Arg Arg Tyr Asp
65 70 75 80

His Ser Ser Asp Ser Ile Phe Phe Ala Asn Asn Arg Ser Tyr Thr Arg
85 90 95

Asp Ser Tyr Lys Met Ala Gly Met Ala Asp Asn Ile Glu Asp Leu Leu
100 105 110

His Phe Cys Arg Gln Met Phe Ser Met Lys Val Asp Asn Val Glu Tyr
115 120 125

Ala Leu Leu Thr Ala Ile Val Ile Phe Ser Asp Arg Pro Gly Leu Glu
130 135 140

Lys Ala Gln Leu Val Glu Ala Ile Gln Ser Tyr Tyr Ile Asp Thr Leu

-continued

```
145                 150                 155                 160

Arg Ile Tyr Ile Leu Asn Arg His Cys Gly Asp Ser Met Ser Leu Val
                165                 170                 175

Phe Tyr Ala Lys Leu Leu Ser Ile Leu Thr Glu Leu Arg Thr Leu Gly
            180                 185                 190

Asn Gln Asn Ala Glu Met Cys Phe Ser Leu Lys Leu Lys Asn Arg Lys
        195                 200                 205

Leu Pro Lys Phe Leu Glu Glu Ile Trp Asp Val His Ala Ile Pro Pro
    210                 215                 220

Ser Val Gln Ser His Leu Gln Ile Thr Gln Glu Glu Asn Glu Arg Leu
225                 230                 235                 240

Glu Arg Ala Glu Arg Met Arg Ala Ser Val Gly Gly Ala Ile Thr Ala
                245                 250                 255

Gly Ile Asp Cys Asp Ser Ala Ser Thr Ser Ala Ala Ala Ala Ala Ala
            260                 265                 270

Gln His Gln Pro Gln Pro Gln Pro Gln Pro Gln Pro Ser Ser Leu Thr
        275                 280                 285

Gln Asn Asp Ser Gln His Gln Thr Gln Pro Gln Leu Gln Pro Gln Leu
    290                 295                 300

Pro Pro Gln Leu Gln Gly Gln Leu Gln Pro Gln Leu Gln Pro Gln Leu
305                 310                 315                 320

Gln Thr Gln Leu Gln Pro Gln Ile Gln Pro Gln Pro Gln Leu Leu Pro
                325                 330                 335

Val Ser Ala Pro Val Pro Ala Ser Val Thr Ala Pro Gly Ser Leu Ser
            340                 345                 350

Ala Val Ser Thr Ser Ser Glu Tyr Met Gly Gly Ser Ala Ala Ile Gly
        355                 360                 365

Pro Ile Thr Pro Ala Thr Thr Ser Ser Ile Thr Ala Ala Val Thr Ala
    370                 375                 380

Ser Ser Thr Thr Ser Ala Val Pro Met Gly Asn Gly Val Gly Val Gly
385                 390                 395                 400

Val Gly Val Gly Gly Asn Val Ser Met Tyr Ala Asn Ala Gln Thr Ala
                405                 410                 415

Met Ala Leu Met Gly Val Ala Leu His Ser His Gln Glu Gln Leu Ile
            420                 425                 430

Gly Gly Val Ala Val Lys Ser Glu His Ser Thr Thr Ala
        435                 440                 445


<210> SEQ ID NO 7
<211> LENGTH: 320
<212> TYPE: PRT
<213> ORGANISM: Choristoneura fumiferana

<400> SEQUENCE: 7

Pro Glu Cys Val Val Pro Glu Thr Gln Cys Ala Met Lys Arg Lys Glu
1               5                   10                  15

Lys Lys Ala Gln Lys Glu Lys Asp Lys Leu Pro Val Ser Thr Thr Thr
            20                  25                  30

Val Asp Asp His Met Pro Pro Ile Met Gln Cys Glu Pro Pro Pro Pro
        35                  40                  45

Glu Ala Ala Arg Ile His Glu Val Val Pro Arg Phe Leu Ser Asp Lys
    50                  55                  60

Leu Leu Glu Thr Asn Arg Gln Lys Asn Ile Pro Gln Leu Thr Ala Asn
65                  70                  75                  80

Gln Gln Phe Leu Ile Ala Arg Leu Ile Trp Tyr Gln Asp Gly Tyr Glu
```

```
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285

Gly Met Gln Asn Ser Asn Met Cys Ile Ser Leu Lys Leu Lys Asn Arg
    290                 295                 300

Lys Leu Pro Pro Phe Leu Glu Glu Ile Trp Asp Val Ala Asp Met Ser
305                 310                 315                 320


<210> SEQ ID NO 8
<211> LENGTH: 323
<212> TYPE: PRT
<213> ORGANISM: Drosophila melanogaster

<400> SEQUENCE: 8

Arg Pro Glu Cys Val Val Pro Glu Asn Gln Cys Ala Met Lys Arg Arg
1               5                   10                  15

Glu Lys Lys Ala Gln Lys Glu Lys Asp Lys Met Thr Thr Ser Pro Ser
            20                  25                  30

Ser Gln His Gly Gly Asn Gly Ser Leu Ala Ser Gly Gly Gly Gln Asp
        35                  40                  45

Phe Val Lys Lys Glu Ile Leu Asp Leu Met Thr Cys Glu Pro Pro Gln
    50                  55                  60

His Ala Thr Ile Pro Leu Leu Pro Asp Glu Ile Leu Ala Lys Cys Gln
65                  70                  75                  80

Ala Arg Asn Ile Pro Ser Leu Thr Tyr Asn Gln Leu Ala Val Ile Tyr
                85                  90                  95

Lys Leu Ile Trp Tyr Gln Asp Gly Tyr Glu Gln Pro Ser Glu Glu Asp
            100                 105                 110

Leu Arg Arg Ile Met Ser Gln Pro Asp Glu Asn Glu Ser Gln Thr Asp
        115                 120                 125

Val Ser Phe Arg His Ile Thr Glu Ile Thr Ile Leu Thr Val Gln Leu
    130                 135                 140

Ile Val Glu Phe Ala Lys Gly Leu Pro Ala Phe Thr Lys Ile Pro Gln
```

```
145                 150                 155                 160

Glu Asp Gln Ile Thr Leu Leu Lys Ala Cys Ser Ser Glu Val Met Met
                165                 170                 175

Leu Arg Met Ala Arg Arg Tyr Asp His Ser Ser Asp Ser Ile Phe Phe
            180                 185                 190

Ala Asn Asn Arg Ser Tyr Thr Arg Asp Ser Tyr Lys Met Ala Gly Met
        195                 200                 205

Ala Asp Asn Ile Glu Asp Leu Leu His Phe Cys Arg Gln Met Phe Ser
    210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
            260                 265                 270

Cys Gly Asp Ser Met Ser Leu Val Phe Tyr Ala Lys Leu Leu Ser Ile
        275                 280                 285

Leu Thr Glu Leu Arg Thr Leu Gly Asn Gln Asn Ala Glu Met Cys Phe
    290                 295                 300

Ser Leu Lys Leu Lys Asn Arg Lys Leu Pro Lys Phe Leu Glu Glu Ile
305                 310                 315                 320

Trp Asp Val


<210> SEQ ID NO 9
<211> LENGTH: 714
<212> TYPE: DNA
<213> ORGANISM: Mus musculus

<400> SEQUENCE: 9

gccaacgagg acatgcctgt agagaagatt ctggaagccg agcttgctgt cgagcccaag     60

actgagacat acgtggaggc aaacatgggg ctgaacccca gctcaccaaa tgaccctgtt    120

accaacatct gtcaagcagc agacaagcag ctcttcactc ttgtggagtg ggccaagagg    180

atcccacact tttctgagct gcccctagac gaccaggtca tcctgctacg ggcaggctgg    240

aacgagctgc tgatcgcctc cttctcccac cgctccatag ctgtgaaaga tgggattctc    300

ctggccaccg gcctgcacgt acaccggaac agcgctcaca gtgctggggt gggcgccatc    360

tttgacaggg tgctaacaga gctggtgtct aagatgcgtg acatgcagat ggacaagacg    420

gagctgggct gcctgcgagc cattgtcctg ttcaaccctg actctaaggg gctctcaaac    480

cctgctgagg tggaggcgtt gagggagaag gtgtatgcgt cactagaagc gtactgcaaa    540

cacaagtacc ctgagcagcc gggcaggttt gccaagctgc tgctccgcct gcctgcactg    600

cgttccatcg ggctcaagtg cctggagcac ctgttcttct tcaagctcat cggggacacg    660

cccatcgaca ccttcctcat ggagatgctg gaggcaccac atcaagccac ctag          714


<210> SEQ ID NO 10
<211> LENGTH: 720
<212> TYPE: DNA
<213> ORGANISM: Mus musculus

<400> SEQUENCE: 10

gcccctgagg agatgcctgt ggacaggatc ctggaggcag agcttgctgt ggagcagaag     60

agtgaccaag gcgttgaggg tcctggggcc accgggggtg gtggcagcag cccaaatgac    120

ccagtgacta acatctgcca ggcagctgac aaacagctgt tcacactcgt tgagtgggca    180
```

-continued

```
aagaggatcc cgcacttctc ctccctacct ctggacgatc aggtcatact gctgcgggca    240

ggctggaacg agctcctcat tgcgtccttc tcccatcggt ccattgatgt ccgagatggc    300

atcctcctgg ccacgggtct tcatgtgcac agaaactcag cccattccgc aggcgtggga    360

gccatctttg atcgggtgct gacagagcta gtgtccaaaa tgcgtgacat gaggatggac    420

aagacagagc ttggctgcct gcgggcaatc atcatgttta atccagacgc caagggcctc    480

tccaaccctg gagaggtgga gatccttcgg gagaaggtgt acgcctcact ggagacctat    540

tgcaagcaga agtaccctga gcagcagggc cggtttgcca agctgctgtt acgtcttcct    600

gccctccgct ccatcggcct caagtgtctg gagcacctgt tcttcttcaa gctcattggc    660

gacaccccca ttgacacctt cctcatggag atgcttgagg ctccccacca gctagcctga    720


<210> SEQ ID NO 11
<211> LENGTH: 705
<212> TYPE: DNA
<213> ORGANISM: Mus musculus

<400> SEQUENCE: 11

agccacgaag acatgcccgt ggagaggatt ctagaagccg aacttgctgt ggaaccaaag     60

acagaatcct acggtgacat gaacgtggag aactcaacaa atgaccctgt taccaacata    120

tgccatgctg cagataagca acttttcacc ctcgttgagt gggccaaacg catcccccac    180

ttctcagatc tcaccttgga ggaccaggtc attctactcc gggcagggtg gaatgaactg    240

ctcattgcct ccttctccca ccgctcggtt tccgtccagg atggcatcct gctggccacg    300

ggcctccacg tgcacaggag cagcgctcac agccggggag tcggctccat cttcgacaga    360

gtccttacag agttggtgtc caagatgaaa gacatgcaga tggataagtc agagctgggg    420

tgcctacggg ccatcgtgct gtttaaccca gatgccaagg gtttatccaa cccctctgag    480

gtggagactc ttcgagagaa ggtttatgcc accctggagg cctataccaa gcagaagtat    540

ccggaacagc caggcaggtt tgccaagctt ctgctgcgtc tccctgctct gcgctccatc    600

ggcttgaaat gcctggaaca cctcttcttc ttcaagctca ttggagacac tcccatcgac    660

agcttcctca tggagatgtt ggagacccca ctgcagatca cctga                    705


<210> SEQ ID NO 12
<211> LENGTH: 850
<212> TYPE: DNA
<213> ORGANISM: Homo sapiens

<400> SEQUENCE: 12

gccaacgagg acatgccggt ggagaggatc ctggaggctg agctggccgt ggagcccaag     60

accgagacct acgtggaggc aaacatgggg ctgaacccca gctcgccgaa cgaccctgtc    120

accaacattt gccaagcagc cgacaaacag cttttcaccc tggtggagtg ggccaagcgg    180

atcccacact tctcagagct gcccctggac gaccaggtca tcctgctgcg ggcaggctgg    240

aatgagctgc tcatcgcctc cttctcccac cgctccatcg ccgtgaagga cgggatcctc    300

ctggccaccg ggctgcacgt ccaccggaac agcgcccaca gcgcaggggt gggcgccatc    360

tttgacaggg tgctgacgga gcttgtgtcc aagatgcggg acatgcagat ggacaagacg    420

gagctgggct gcctgcgcgc catcgtcctc tttaaccctg actccaaggg gctctcgaac    480

ccggccgagg tggaggcgct gagggagaag gtctatgcgt ccttggaggc ctactgcaag    540

cacaagtacc cagagcagcc gggaaggttc gctaagctct tgctccgcct gccggctctg    600

cgctccatcg ggctcaaatg cctggaacat ctcttcttct tcaagctcat cggggacaca    660
```

cccattgaca ccttccttat ggagatgctg gaggcgccgc accaaatgac ttaggcctgc 720
gggcccatcc tttgtgccca cccgttctgg ccaccctgcc tggacgccag ctgttcttct 780
cagcctgagc cctgtccctg cccttctctg cctggcctgt ttggactttg gggcacagcc 840
tgtcactgct 850

<210> SEQ ID NO 13
<211> LENGTH: 720
<212> TYPE: DNA
<213> ORGANISM: Homo sapiens

<400> SEQUENCE: 13
gcccccgagg agatgcctgt ggacaggatc ctggaggcag agcttgctgt ggaacagaag 60
agtgaccagg gcgttgaggg tcctggggga accgggggta gcggcagcag cccaaatgac 120
cctgtgacta acatctgtca ggcagctgac aaacagctat tcacgcttgt tgagtgggcg 180
aagaggatcc cacacttttc ctccttgcct ctggatgatc aggtcatatt gctgcgggca 240
ggctggaatg aactcctcat tgcctccttt tcacaccgat ccattgatgt tcgagatggc 300
atcctccttg ccacaggtct tcacgtgcac cgcaactcag cccattcagc aggagtagga 360
gccatctttg atcgggtgct gacagagcta gtgtccaaaa tgcgtgacat gaggatggac 420
aagacagagc ttggctgcct gagggcaatc attctgttta atccagatgc caagggcctc 480
tccaacccta gtgaggtgga ggtcctgcgg gagaaagtgt atgcatcact ggagacctac 540
tgcaaacaga agtaccctga gcagcaggga cggtttgcca agctgctgct acgtcttcct 600
gccctccggt ccattggcct taagtgtcta gagcatctgt ttttcttcaa gctcattggt 660
gacaccccca tcgacacctt cctcatggag atgcttgagg ctccccatca actggcctga 720

<210> SEQ ID NO 14
<211> LENGTH: 705
<212> TYPE: DNA
<213> ORGANISM: Homo sapiens

<400> SEQUENCE: 14
ggtcatgaag acatgcctgt ggagaggatt ctagaagctg aacttgctgt tgaaccaaag 60
acagaatcct atggtgacat gaatatggag aactcgacaa atgaccctgt taccaacata 120
tgtcatgctg ctgacaagca gcttttcacc ctcgttgaat gggccaagcg tattccccac 180
ttctctgacc tcaccttgga ggaccaggtc attttgcttc gggcagggtg gaatgaattg 240
ctgattgcct ctttctccca ccgctcagtt tccgtgcagg atggcatcct tctggccacg 300
ggtttacatg tccaccggag cagtgcccac agtgctgggg tcggctccat ctttgacaga 360
gttctaactg agctggtttc caaaatgaaa gacatgcaga tggacaagtc ggaactggga 420
tgcctgcgag ccattgtact ctttaaccca gatgccaagg gcctgtccaa cccctctgag 480
gtggagactc tgcgagagaa ggtttatgcc acccttgagg cctacaccaa gcagaagtat 540
ccggaacagc caggcaggtt tgccaagctg ctgctgcgcc tcccagctct gcgttccatt 600
ggcttgaaat gcctggagca cctcttcttc ttcaagctca tcggggacac ccccattgac 660
accttcctca tggagatgtt ggagaccccg ctgcagatca cctga 705

<210> SEQ ID NO 15
<211> LENGTH: 237
<212> TYPE: PRT
<213> ORGANISM: Mus musculus

<400> SEQUENCE: 15

```
Ala Asn Glu Asp Met Pro Val Glu Lys Ile Leu Glu Ala Glu Leu Ala
1               5                   10                  15

Val Glu Pro Lys Thr Glu Thr Tyr Val Glu Ala Asn Met Gly Leu Asn
            20                  25                  30

Pro Ser Ser Pro Asn Asp Pro Val Thr Asn Ile Cys Gln Ala Ala Asp
        35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Phe Lys Leu Ile Gly Asp Thr Pro Ile Asp Thr
    210                 215                 220

Phe Leu Met Glu Met Leu Glu Ala Pro His Gln Ala Thr
225                 230                 235
```

<210> SEQ ID NO 16
<211> LENGTH: 239
<212> TYPE: PRT
<213> ORGANISM: Mus musculus

<400> SEQUENCE: 16

```
Ala Pro Glu Glu Met Pro Val Asp Arg Ile Leu Glu Ala Glu Leu Ala
1               5                   10                  15

Val Glu Gln Lys Ser Asp Gln Gly Val Glu Gly Pro Gly Ala Thr Gly
            20                  25                  30

Gly Gly Gly Ser Ser Pro Asn Asp Pro Val Thr Asn Ile Cys Gln Ala
        35                  40                  45

Ala Asp Lys Gln Leu Phe Thr Leu Val Glu Trp Ala Lys Arg Ile Pro
    50                  55                  60

His Phe Ser Ser Leu Pro Leu Asp Asp Gln Val Ile Leu Leu Arg Ala
65                  70                  75                  80

Gly Trp Asn Glu Leu Leu Ile Ala Ser Phe Ser His Arg Ser Ile Asp
                85                  90                  95

Val Arg Asp Gly Ile Leu Leu Ala Thr Gly Leu His Val His Arg Asn
            100                 105                 110

Ser Ala His Ser Ala Gly Val Gly Ala Ile Phe Asp Arg Val Leu Thr
        115                 120                 125

Glu Leu Val Ser Lys Met Arg Asp Met Arg Met Asp Lys Thr Glu Leu
    130                 135                 140
```

```
Gly Cys Leu Arg Ala Ile Ile Met Phe Asn Pro Asp Ala Lys Gly Leu
145                 150                 155                 160

Ser Asn Pro Gly Glu Val Glu Ile Leu Arg Glu Lys Val Tyr Ala Ser
                165                 170                 175

Leu Glu Thr Tyr Cys Lys Gln Lys Tyr Pro Glu Gln Gln Gly Arg Phe
            180                 185                 190

Ala Lys Leu Leu Leu Arg Leu Pro Ala Leu Arg Ser Ile Gly Leu Lys
        195                 200                 205

Cys Leu Glu His Leu Phe Phe Phe Lys Leu Ile Gly Asp Thr Pro Ile
    210                 215                 220

Asp Thr Phe Leu Met Glu Met Leu Glu Ala Pro His Gln Leu Ala
225                 230                 235


<210> SEQ ID NO 17
<211> LENGTH: 234
<212> TYPE: PRT
<213> ORGANISM: Mus musculus

<400> SEQUENCE: 17

Ser His Glu Asp Met Pro Val Glu Arg Ile Leu Glu Ala Glu Leu Ala
1               5                   10                  15

Val Glu Pro Lys Thr Glu Ser Tyr Gly Asp Met Asn Val Glu Asn Ser
            20                  25                  30

Thr Asn Asp Pro Val Thr Asn Ile Cys His Ala Ala Asp Lys Gln Leu
        35                  40                  45

Phe Thr Leu Val Glu Trp Ala Lys Arg Ile Pro His Phe Ser Asp Leu
    50                  55                  60

Thr Leu Glu Asp Gln Val Ile Leu Leu Arg Ala Gly Trp Asn Glu Leu
65                  70                  75                  80

Leu Ile Ala Ser Phe Ser His Arg Ser Val Ser Val Gln Asp Gly Ile
                85                  90                  95

Leu Leu Ala Thr Gly Leu His Val His Arg Ser Ser Ala His Ser Arg
            100                 105                 110

Gly Val Gly Ser Ile Phe Asp Arg Val Leu Thr Glu Leu Val Ser Lys
        115                 120                 125

Met Lys Asp Met Gln Met Asp Lys Ser Glu Leu Gly Cys Leu Arg Ala
    130                 135                 140

Ile Val Leu Phe Asn Pro Asp Ala Lys Gly Leu Ser Asn Pro Ser Glu
145                 150                 155                 160

Val Glu Thr Leu Arg Glu Lys Val Tyr Ala Thr Leu Glu Ala Tyr Thr
                165                 170                 175

Lys Gln Lys Tyr Pro Glu Gln Pro Gly Arg Phe Ala Lys Leu Leu Leu
            180                 185                 190

Arg Leu Pro Ala Leu Arg Ser Ile Gly Leu Lys Cys Leu Glu His Leu
        195                 200                 205

Phe Phe Phe Lys Leu Ile Gly Asp Thr Pro Ile Asp Ser Phe Leu Met
    210                 215                 220

Glu Met Leu Glu Thr Pro Leu Gln Ile Thr
225                 230


<210> SEQ ID NO 18
<211> LENGTH: 237
<212> TYPE: PRT
<213> ORGANISM: Homo sapiens

<400> SEQUENCE: 18

Ala Asn Glu Asp Met Pro Val Glu Arg Ile Leu Glu Ala Glu Leu Ala
```

```
1               5                   10                  15

Val Glu Pro Lys Thr Glu Thr Tyr Val Glu Ala Asn Met Gly Leu Asn
            20                  25                  30

Pro Ser Ser Pro Asn Asp Pro Val Thr Asn Ile Cys Gln Ala Ala Asp
        35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Phe Lys Leu Ile Gly Asp Thr Pro Ile Asp Thr
    210                 215                 220

Phe Leu Met Glu Met Leu Glu Ala Pro His Gln Met Thr
225                 230                 235


<210> SEQ ID NO 19
<211> LENGTH: 239
<212> TYPE: PRT
<213> ORGANISM: Homo sapiens

<400> SEQUENCE: 19

Ala Pro Glu Glu Met Pro Val Asp Arg Ile Leu Glu Ala Glu Leu Ala
1               5                   10                  15

Val Glu Gln Lys Ser Asp Gln Gly Val Glu Gly Pro Gly Gly Thr Gly
            20                  25                  30

Gly Ser Gly Ser Ser Pro Asn Asp Pro Val Thr Asn Ile Cys Gln Ala
        35                  40                  45

Ala Asp Lys Gln Leu Phe Thr Leu Val Glu Trp Ala Lys Arg Ile Pro
    50                  55                  60

His Phe Ser Ser Leu Pro Leu Asp Asp Gln Val Ile Leu Leu Arg Ala
65                  70                  75                  80

Gly Trp Asn Glu Leu Leu Ile Ala Ser Phe Ser His Arg Ser Ile Asp
                85                  90                  95

Val Arg Asp Gly Ile Leu Leu Ala Thr Gly Leu His Val His Arg Asn
            100                 105                 110

Ser Ala His Ser Ala Gly Val Gly Ala Ile Phe Asp Arg Val Leu Thr
        115                 120                 125

Glu Leu Val Ser Lys Met Arg Asp Met Arg Met Asp Lys Thr Glu Leu
    130                 135                 140

Gly Cys Leu Arg Ala Ile Ile Leu Phe Asn Pro Asp Ala Lys Gly Leu
```

```
145                 150                 155                 160

Ser Asn Pro Ser Glu Val Glu Val Leu Arg Glu Lys Val Tyr Ala Ser
                165                 170                 175

Leu Glu Thr Tyr Cys Lys Gln Lys Tyr Pro Glu Gln Gln Gly Arg Phe
            180                 185                 190

Ala Lys Leu Leu Leu Arg Leu Pro Ala Leu Arg Ser Ile Gly Leu Lys
        195                 200                 205

Cys Leu Glu His Leu Phe Phe Phe Lys Leu Ile Gly Asp Thr Pro Ile
    210                 215                 220

Asp Thr Phe Leu Met Glu Met Leu Glu Ala Pro His Gln Leu Ala
225                 230                 235


<210> SEQ ID NO 20
<211> LENGTH: 234
<212> TYPE: PRT
<213> ORGANISM: Homo sapiens

<400> SEQUENCE: 20

Gly His Glu Asp Met Pro Val Glu Arg Ile Leu Glu Ala Glu Leu Ala
1               5                   10                  15

Val Glu Pro Lys Thr Glu Ser Tyr Gly Asp Met Asn Met Glu Asn Ser
            20                  25                  30

Thr Asn Asp Pro Val Thr Asn Ile Cys His Ala Ala Asp Lys Gln Leu
        35                  40                  45

Phe Thr Leu Val Glu Trp Ala Lys Arg Ile Pro His Phe Ser Asp Leu
    50                  55                  60

Thr Leu Glu Asp Gln Val Ile Leu Leu Arg Ala Gly Trp Asn Glu Leu
65                  70                  75                  80

Leu Ile Ala Ser Phe Ser His Arg Ser Val Ser Val Gln Asp Gly Ile
                85                  90                  95

Leu Leu Ala Thr Gly Leu His Val His Arg Ser Ser Ala His Ser Ala
            100                 105                 110

Gly Val Gly Ser Ile Phe Asp Arg Val Leu Thr Glu Leu Val Ser Lys
        115                 120                 125

Met Lys Asp Met Gln Met Asp Lys Ser Glu Leu Gly Cys Leu Arg Ala
    130                 135                 140

Ile Val Leu Phe Asn Pro Asp Ala Lys Gly Leu Ser Asn Pro Ser Glu
145                 150                 155                 160

Val Glu Thr Leu Arg Glu Lys Val Tyr Ala Thr Leu Glu Ala Tyr Thr
                165                 170                 175

Lys Gln Lys Tyr Pro Glu Gln Pro Gly Arg Phe Ala Lys Leu Leu Leu
            180                 185                 190

Arg Leu Pro Ala Leu Arg Ser Ile Gly Leu Lys Cys Leu Glu His Leu
        195                 200                 205

Phe Phe Phe Lys Leu Ile Gly Asp Thr Pro Ile Asp Thr Phe Leu Met
    210                 215                 220

Glu Met Leu Glu Thr Pro Leu Gln Ile Thr
225                 230


<210> SEQ ID NO 21
<211> LENGTH: 635
<212> TYPE: DNA
<213> ORGANISM: Locusta migratoria

<400> SEQUENCE: 21

tgcatacaga catgcctgtt gaacgcatac ttgaagctga aaaacgagtg gagtgcaaag     60
```

```
cagaaaacca agtggaatat gagctggtgg agtgggctaa acacatcccg cacttcacat    120

ccctacctct ggaggaccag gttctcctcc tcagagcagg ttggaatgaa ctgctaattg    180

cagcattttc acatcgatct gtagatgtta aagatggcat agtacttgcc actggtctca    240

cagtgcatcg aaattctgcc catcaagctg gagtcggcac aatatttgac agagttttga    300

cagaactggt agcaaagatg agagaaatga aaatggataa aactgaactt ggctgcttgc    360

gatctgttat tcttttcaat ccagaggtga ggggtttgaa atccgcccag gaagttgaac    420

ttctacgtga aaaagtatat gccgctttgg aagaatatac tagaacaaca catcccgatg    480

aaccaggaag atttgcaaaa cttttgcttc gtctgccttc tttacgttcc ataggcctta    540

agtgtttgga gcatttgttt ttctttcgcc ttattggaga tgttccaatt gatacgttcc    600

tgatggagat gcttgaatca ccttctgatt cataa                               635


<210> SEQ ID NO 22
<211> LENGTH: 687
<212> TYPE: DNA
<213> ORGANISM: Amblyomma americanum

<400> SEQUENCE: 22

cctcctgaga tgcctctgga gcgcatactg gaggcagagc tgcgggttga gtcacagacg     60

gggaccctct cggaaagcgc acagcagcag gatccagtga gcagcatctg ccaagctgca    120

gaccgacagc tgcaccagct agttcaatgg gccaagcaca ttccacattt tgaagagctt    180

ccccttgagg accgcatggt gttgctcaag gctggctgga acgagctgct cattgctgct    240

ttctcccacc gttctgttga cgtgcgtgat ggcattgtgc tcgctacagg tcttgtggtg    300

cagcggcata gtgctcatgg ggctggcgtt ggggccatat ttgatagggt tctcactgaa    360

ctggtagcaa agatgcgtga gatgaagatg gaccgcactg agcttggatg cctgcttgct    420

gtggtacttt ttaatcctga ggccaagggg ctgcggacct gcccaagtgg aggccctgag    480

ggagaaagtg tatctgcctt ggaagagcac tgccggcagc agtacccaga ccagcctggg    540

cgctttgcca agctgctgct gcggttgcca gctctgcgca gtattggcct caagtgcctc    600

gaacatctct ttttcttcaa gctcatcggg gacacgccca tcgacaactt tcttctttcc    660

atgctggagg ccccctctga cccctaa                                        687


<210> SEQ ID NO 23
<211> LENGTH: 693
<212> TYPE: DNA
<213> ORGANISM: Amblyomma americanum

<400> SEQUENCE: 23

tctccggaca tgccactcga acgcattctc gaagccgaga tgcgcgtcga gcagccggca     60

ccgtccgttt tggcgcagac ggccgcatcg ggccgcgacc ccgtcaacag catgtgccag    120

gctgccccgc cacttcacga gctcgtacag tgggcccggc gaattccgca cttcgaagag    180

cttcccatcg aggatcgcac cgcgctgctc aaagccggct ggaacgaact gcttattgcc    240

gccttttcgc accgttctgt ggcggtgcgc gacggcatcg ttctggccac cgggctggtg    300

gtgcagcggc acagcgcaca cggcgcaggc gttggcgaca tcttcgaccg cgtactagcc    360

gagctggtgg ccaagatgcg cgacatgaag atggacaaaa cggagctcgg ctgcctgcgc    420

gccgtggtgc tcttcaatcc agacgccaag ggtctccgaa acgccaccag agtagaggcg    480

ctccgcgaga aggtgtatgc ggcgctggag gagcactgcc gtcggcacca cccggaccaa    540

ccgggtcgct tcggcaagct gctgctgcgg ctgcctgcct tgcgcagcat cgggctcaaa    600
```

-continued

```
tgcctcgagc atctgttctt cttcaagctc atcggagaca ctcccataga cagcttcctg    660

ctcaacatgc tggaggcacc ggcagacccc tag                                 693


<210> SEQ ID NO 24
<211> LENGTH: 801
<212> TYPE: DNA
<213> ORGANISM: Celuca pugilator

<400> SEQUENCE: 24

tcagacatgc caattgccag catacgggag gcagagctca gcgtggatcc catagatgag     60

cagccgctgg accaaggggt gaggcttcag gttccactcg cacctcctga tagtgaaaag    120

tgtagcttta ctttaccttt tcatcccgtc agtgaagtat cctgtgctaa ccctctgcag    180

gatgtggtga gcaacatatg ccaggcagct gacagacatc tggtgcagct ggtggagtgg    240

gccaagcaca tcccacactt cacagacctt cccatagagg accaagtggt attactcaaa    300

gccgggtgga acgagttgct tattgcctca ttctcacacc gtagcatggg cgtggaggat    360

ggcatcgtgc tggccacagg gctcgtgatc cacagaagta gtgctcacca ggctggagtg    420

ggtgccatat ttgatcgtgt cctctctgag ctggtggcca agatgaagga gatgaagatt    480

gacaagacag agctgggctg ccttcgctcc atcgtcctgt tcaacccaga tgccaaagga    540

ctaaactgcg tcaatgatgt ggagatcttg cgtgagaagg tgtatgctgc cctggaggag    600

tacacacgaa ccacttaccc tgatgaacct ggacgctttg ccaagttgct tctgcgactt    660

cctgcactca ggtctatagg cctgaagtgt cttgagtacc tcttcctgtt taagctgatt    720

ggagacactc ccctggacag ctacttgatg aagatgctcg tagacaaccc aaatacaagc    780

gtcactcccc ccaccagcta g                                              801


<210> SEQ ID NO 25
<211> LENGTH: 690
<212> TYPE: DNA
<213> ORGANISM: Tenebrio molitor

<400> SEQUENCE: 25

gccgagatgc ccctcgacag gataatcgag gcggagaaac ggatagaatg cacacccgct     60

ggtggctctg gtggtgtcgg agagcaacac gacggggtga acaacatctg tcaagccact    120

aacaagcagc tgttccaact ggtgcaatgg gctaagctca tacctcactt tacctcgttg    180

ccgatgtcgg accaggtgct tttattgagg gcaggatgga atgaattgct catcgccgca    240

ttctcgcaca gatctataca ggcgcaggat gccatcgttc tagccacggg gttgacagtt    300

aacaaaacgt cggcgcacgc cgtgggcgtg ggcaacatct acgaccgcgt cctctccgag    360

ctggtgaaca agatgaaaga gatgaagatg gacaagacgg agctgggctg cttgagagcc    420

atcatcctct acaaccccac gtgtcgcggc atcaagtccg tgcaggaagt ggagatgctg    480

cgtgagaaaa tttacggcgt gctggaagag tacaccagga ccacccaccc gaacgagccc    540

ggcaggttcg ccaaactgct tctgcgcctc ccggccctca ggtccatcgg gttgaaatgt    600

tccgaacacc tctttttctt caagctgatc ggtgatgttc caatagacac gttcctgatg    660

gagatgctgg agtctccggc ggacgcttag                                     690


<210> SEQ ID NO 26
<211> LENGTH: 681
<212> TYPE: DNA
<213> ORGANISM: Apis mellifera

<400> SEQUENCE: 26
```

-continued

```
cattcggaca tgccgatcga gcgtatcctg gaggccgaga agagagtcga atgtaagatg     60

gagcaacagg gaaattacga gaatgcagtg tcgcacattt gcaacgccac gaacaaacag    120

ctgttccagc tggtagcatg ggcgaaacac atcccgcatt ttacctcgtt gccactggag    180

gatcaggtac ttctgctcag ggccggttgg aacgagttgc tgatagcctc cttttcccac    240

cgttccatcg acgtgaagga cggtatcgtg ctggcgacgg ggatcaccgt gcatcggaac    300

tcggcgcagc aggccggcgt gggcacgata ttcgaccgtg tcctctcgga gcttgtctcg    360

aaaatgcgtg aaatgaagat ggacaggaca gagcttggct gtctcagatc tataatactc    420

ttcaatcccg aggttcgagg actgaaatcc atccaggaag tgaccctgct ccgtgagaag    480

atctacggcg ccctggaggg ttattgccgc gtagcttggc ccgacgacgc tggaagattc    540

gcgaaattac ttctacgcct gcccgccatc cgctcgatcg gattaaagtg cctcgagtac    600

ctgttcttct tcaaaatgat cggtgacgta ccgatcgacg attttctcgt ggagatgtta    660

gaatcgcgat cagatcctta g                                               681
```

<210> SEQ ID NO 27
<211> LENGTH: 210
<212> TYPE: PRT
<213> ORGANISM: Locusta migratoria

<400> SEQUENCE: 27

```
His Thr Asp Met Pro Val Glu Arg Ile Leu Glu Ala Glu Lys Arg Val
1               5                   10                  15

Glu Cys Lys Ala Glu Asn Gln Val Glu Tyr Glu Leu Val Glu Trp Ala
            20                  25                  30

Lys His Ile Pro His Phe Thr Ser Leu Pro Leu Glu Asp Gln Val Leu
        35                  40                  45

Leu Leu Arg Ala Gly Trp Asn Glu Leu Leu Ile Ala Ala Phe Ser His
    50                  55                  60

Arg Ser Val Asp Val Lys Asp Gly Ile Val Leu Ala Thr Gly Leu Thr
65                  70                  75                  80

Val His Arg Asn Ser Ala His Gln Ala Gly Val Gly Thr Ile Phe Asp
                85                  90                  95

Arg Val Leu Thr Glu Leu Val Ala Lys Met Arg Glu Met Lys Met Asp
            100                 105                 110

Lys Thr Glu Leu Gly Cys Leu Arg Ser Val Ile Leu Phe Asn Pro Glu
        115                 120                 125

Val Arg Gly Leu Lys Ser Ala Gln Glu Val Glu Leu Leu Arg Glu Lys
    130                 135                 140

Val Tyr Ala Ala Leu Glu Glu Tyr Thr Arg Thr Thr His Pro Asp Glu
145                 150                 155                 160

Pro Gly Arg Phe Ala Lys Leu Leu Leu Arg Leu Pro Ser Leu Arg Ser
                165                 170                 175

Ile Gly Leu Lys Cys Leu Glu His Leu Phe Phe Phe Arg Leu Ile Gly
            180                 185                 190

Asp Val Pro Ile Asp Thr Phe Leu Met Glu Met Leu Glu Ser Pro Ser
        195                 200                 205

Asp Ser
    210
```

<210> SEQ ID NO 28
<211> LENGTH: 228
<212> TYPE: PRT
<213> ORGANISM: Amblyomma americanum

<400> SEQUENCE: 28

```
Pro Pro Glu Met Pro Leu Glu Arg Ile Leu Glu Ala Glu Leu Arg Val
1               5                   10                  15

Glu Ser Gln Thr Gly Thr Leu Ser Glu Ser Ala Gln Gln Gln Asp Pro
            20                  25                  30

Val Ser Ser Ile Cys Gln Ala Ala Asp Arg Gln Leu His Gln Leu Val
        35                  40                  45

Gln Trp Ala Lys His Ile Pro His Phe Glu Glu Leu Pro Leu Glu Asp
    50                  55                  60

Arg Met Val Leu Leu Lys Ala Gly Trp Asn Glu Leu Leu Ile Ala Ala
65                  70                  75                  80

Phe Ser His Arg Ser Val Asp Val Arg Asp Gly Ile Val Leu Ala Thr
                85                  90                  95

Gly Leu Val Val Gln Arg His Ser Ala His Gly Ala Gly Val Gly Ala
            100                 105                 110

Ile Phe Asp Arg Val Leu Thr Glu Leu Val Ala Lys Met Arg Glu Met
        115                 120                 125

Lys Met Asp Arg Thr Glu Leu Gly Cys Leu Leu Ala Val Val Leu Phe
    130                 135                 140

Asn Pro Glu Ala Lys Gly Leu Arg Thr Cys Pro Ser Gly Gly Pro Glu
145                 150                 155                 160

Gly Glu Ser Val Ser Ala Leu Glu Glu His Cys Arg Gln Gln Tyr Pro
                165                 170                 175

Asp Gln Pro Gly Arg Phe Ala Lys Leu Leu Leu Arg Leu Pro Ala Leu
            180                 185                 190

Arg Ser Ile Gly Leu Lys Cys Leu Glu His Leu Phe Phe Phe Lys Leu
        195                 200                 205

Ile Gly Asp Thr Pro Ile Asp Asn Phe Leu Leu Ser Met Leu Glu Ala
    210                 215                 220

Pro Ser Asp Pro
225
```

<210> SEQ ID NO 29
<211> LENGTH: 230
<212> TYPE: PRT
<213> ORGANISM: Amblyomma americanum

<400> SEQUENCE: 29

```
Ser Pro Asp Met Pro Leu Glu Arg Ile Leu Glu Ala Glu Met Arg Val
1               5                   10                  15

Glu Gln Pro Ala Pro Ser Val Leu Ala Gln Thr Ala Ala Ser Gly Arg
            20                  25                  30

Asp Pro Val Asn Ser Met Cys Gln Ala Ala Pro Pro Leu His Glu Leu
        35                  40                  45

Val Gln Trp Ala Arg Arg Ile Pro His Phe Glu Glu Leu Pro Ile Glu
    50                  55                  60

Asp Arg Thr Ala Leu Leu Lys Ala Gly Trp Asn Glu Leu Leu Ile Ala
65                  70                  75                  80

Ala Phe Ser His Arg Ser Val Ala Val Arg Asp Gly Ile Val Leu Ala
                85                  90                  95

Thr Gly Leu Val Val Gln Arg His Ser Ala His Gly Ala Gly Val Gly
            100                 105                 110

Asp Ile Phe Asp Arg Val Leu Ala Glu Leu Val Ala Lys Met Arg Asp
        115                 120                 125

Met Lys Met Asp Lys Thr Glu Leu Gly Cys Leu Arg Ala Val Val Leu
```

-continued

```
    130                 135                 140

Phe Asn Pro Asp Ala Lys Gly Leu Arg Asn Ala Thr Arg Val Glu Ala
145                 150                 155                 160

Leu Arg Glu Lys Val Tyr Ala Ala Leu Glu Glu His Cys Arg Arg His
                165                 170                 175

His Pro Asp Gln Pro Gly Arg Phe Gly Lys Leu Leu Leu Arg Leu Pro
            180                 185                 190

Ala Leu Arg Ser Ile Gly Leu Lys Cys Leu Glu His Leu Phe Phe Phe
        195                 200                 205

Lys Leu Ile Gly Asp Thr Pro Ile Asp Ser Phe Leu Leu Asn Met Leu
    210                 215                 220

Glu Ala Pro Ala Asp Pro
225                 230


<210> SEQ ID NO 30
<211> LENGTH: 266
<212> TYPE: PRT
<213> ORGANISM: Celuca pugilator

<400> SEQUENCE: 30

Ser Asp Met Pro Ile Ala Ser Ile Arg Glu Ala Glu Leu Ser Val Asp
1               5                   10                  15

Pro Ile Asp Glu Gln Pro Leu Asp Gln Gly Val Arg Leu Gln Val Pro
            20                  25                  30

Leu Ala Pro Pro Asp Ser Glu Lys Cys Ser Phe Thr Leu Pro Phe His
        35                  40                  45

Pro Val Ser Glu Val Ser Cys Ala Asn Pro Leu Gln Asp Val Val Ser
    50                  55                  60

Asn Ile Cys Gln Ala Ala Asp Arg His Leu Val Gln Leu Val Glu Trp
65                  70                  75                  80

Ala Lys His Ile Pro His Phe Thr Asp Leu Pro Ile Glu Asp Gln Val
                85                  90                  95

Val Leu Leu Lys Ala Gly Trp Asn Glu Leu Leu Ile Ala Ser Phe Ser
            100                 105                 110

His Arg Ser Met Gly Val Glu Asp Gly Ile Val Leu Ala Thr Gly Leu
        115                 120                 125

Val Ile His Arg Ser Ser Ala His Gln Ala Gly Val Gly Ala Ile Phe
    130                 135                 140

Asp Arg Val Leu Ser Glu Leu Val Ala Lys Met Lys Glu Met Lys Ile
145                 150                 155                 160

Asp Lys Thr Glu Leu Gly Cys Leu Arg Ser Ile Val Leu Phe Asn Pro
                165                 170                 175

Asp Ala Lys Gly Leu Asn Cys Val Asn Asp Val Glu Ile Leu Arg Glu
            180                 185                 190

Lys Val Tyr Ala Ala Leu Glu Glu Tyr Thr Arg Thr Thr Tyr Pro Asp
        195                 200                 205

Glu Pro Gly Arg Phe Ala Lys Leu Leu Leu Arg Leu Pro Ala Leu Arg
    210                 215                 220

Ser Ile Gly Leu Lys Cys Leu Glu Tyr Leu Phe Leu Phe Lys Leu Ile
225                 230                 235                 240

Gly Asp Thr Pro Leu Asp Ser Tyr Leu Met Lys Met Leu Val Asp Asn
                245                 250                 255

Pro Asn Thr Ser Val Thr Pro Pro Thr Ser
            260                 265
```

```
<210> SEQ ID NO 31
<211> LENGTH: 229
<212> TYPE: PRT
<213> ORGANISM: Tenebrio molitor

<400> SEQUENCE: 31

Ala Glu Met Pro Leu Asp Arg Ile Ile Glu Ala Glu Lys Arg Ile Glu
1               5                   10                  15

Cys Thr Pro Ala Gly Gly Ser Gly Gly Val Gly Glu Gln His Asp Gly
            20                  25                  30

Val Asn Asn Ile Cys Gln Ala Thr Asn Lys Gln Leu Phe Gln Leu Val
        35                  40                  45

Gln Trp Ala Lys Leu Ile Pro His Phe Thr Ser Leu Pro Met Ser Asp
    50                  55                  60

Gln Val Leu Leu Leu Arg Ala Gly Trp Asn Glu Leu Leu Ile Ala Ala
65                  70                  75                  80

Phe Ser His Arg Ser Ile Gln Ala Gln Asp Ala Ile Val Leu Ala Thr
                85                  90                  95

Gly Leu Thr Val Asn Lys Thr Ser Ala His Ala Val Gly Val Gly Asn
            100                 105                 110

Ile Tyr Asp Arg Val Leu Ser Glu Leu Val Asn Lys Met Lys Glu Met
        115                 120                 125

Lys Met Asp Lys Thr Glu Leu Gly Cys Leu Arg Ala Ile Ile Leu Tyr
    130                 135                 140

Asn Pro Thr Cys Arg Gly Ile Lys Ser Val Gln Glu Val Glu Met Leu
145                 150                 155                 160

Arg Glu Lys Ile Tyr Gly Val Leu Glu Glu Tyr Thr Arg Thr Thr His
                165                 170                 175

Pro Asn Glu Pro Gly Arg Phe Ala Lys Leu Leu Leu Arg Leu Pro Ala
            180                 185                 190

Leu Arg Ser Ile Gly Leu Lys Cys Ser Glu His Leu Phe Phe Phe Lys
        195                 200                 205

Leu Ile Gly Asp Val Pro Ile Asp Thr Phe Leu Met Glu Met Leu Glu
    210                 215                 220

Ser Pro Ala Asp Ala
225

<210> SEQ ID NO 32
<211> LENGTH: 226
<212> TYPE: PRT
<213> ORGANISM: Apis mellifera

<400> SEQUENCE: 32

His Ser Asp Met Pro Ile Glu Arg Ile Leu Glu Ala Glu Lys Arg Val
1               5                   10                  15

Glu Cys Lys Met Glu Gln Gln Gly Asn Tyr Glu Asn Ala Val Ser His
            20                  25                  30

Ile Cys Asn Ala Thr Asn Lys Gln Leu Phe Gln Leu Val Ala Trp Ala
        35                  40                  45

Lys His Ile Pro His Phe Thr Ser Leu Pro Leu Glu Asp Gln Val Leu
    50                  55                  60

Leu Leu Arg Ala Gly Trp Asn Glu Leu Leu Ile Ala Ser Phe Ser His
65                  70                  75                  80

Arg Ser Ile Asp Val Lys Asp Gly Ile Val Leu Ala Thr Gly Ile Thr
                85                  90                  95

Val His Arg Asn Ser Ala Gln Gln Ala Gly Val Gly Thr Ile Phe Asp
            100                 105                 110
```

-continued

```
Arg Val Leu Ser Glu Leu Val Ser Lys Met Arg Glu Met Lys Met Asp
        115                 120                 125

Arg Thr Glu Leu Gly Cys Leu Arg Ser Ile Ile Leu Phe Asn Pro Glu
    130                 135                 140

Val Arg Gly Leu Lys Ser Ile Gln Glu Val Thr Leu Leu Arg Glu Lys
145                 150                 155                 160

Ile Tyr Gly Ala Leu Glu Gly Tyr Cys Arg Val Ala Trp Pro Asp Asp
                165                 170                 175

Ala Gly Arg Phe Ala Lys Leu Leu Leu Arg Leu Pro Ala Ile Arg Ser
            180                 185                 190

Ile Gly Leu Lys Cys Leu Glu Tyr Leu Phe Phe Phe Lys Met Ile Gly
        195                 200                 205

Asp Val Pro Ile Asp Asp Phe Leu Val Glu Met Leu Glu Ser Arg Ser
    210                 215                 220

Asp Pro
225


<210> SEQ ID NO 33
<211> LENGTH: 516
<212> TYPE: DNA
<213> ORGANISM: Locusta migratoria

<400> SEQUENCE: 33

atccctacct ctggaggacc aggttctcct cctcagagca ggttggaatg aactgctaat     60

tgcagcattt tcacatcgat ctgtagatgt taaagatggc atagtacttg ccactggtct    120

cacagtgcat cgaaattctg cccatcaagc tggagtcggc acaatatttg acagagtttt    180

gacagaactg gtagcaaaga tgagagaaat gaaaatggat aaaactgaac ttggctgctt    240

gcgatctgtt attcttttca atccagaggt gaggggtttg aaatccgccc aggaagttga    300

acttctacgt gaaaaagtat atgccgcttt ggaagaatat actagaacaa cacatcccga    360

tgaaccagga agatttgcaa aactttgct tcgtctgcct tctttacgtt ccataggcct    420

taagtgtttg gagcatttgt tttctttcgc cttattggag atgttccaat tgatacgttc    480

ctgatggaga tgcttgaatc accttctgat tcataa                               516


<210> SEQ ID NO 34
<211> LENGTH: 528
<212> TYPE: DNA
<213> ORGANISM: Amblyomma americanum

<400> SEQUENCE: 34

attccacatt ttgaagagct tccccttgag gaccgcatgg tgttgctcaa ggctggctgg     60

aacgagctgc tcattgctgc tttctcccac cgttctgttg acgtgcgtga tggcattgtg    120

ctcgctacag gtcttgtggt gcagcggcat agtgctcatg ggctggcgt tggggccata    180

tttgataggg ttctcactga actggtagca aagatgcgtg agatgaagat ggaccgcact    240

gagcttggat gcctgcttgc tgtggtactt tttaatcctg aggccaaggg gctgcggacc    300

tgcccaagtg gaggccctga gggagaaagt gtatctgcct tggaagagca ctgccggcag    360

cagtacccag accagcctgg gcgctttgcc aagctgctgc tgcggttgcc agctctgcgc    420

agtattggcc tcaagtgcct cgaacatctc tttttcttca agctcatcgg ggacacgccc    480

atcgacaact ttcttctttc catgctggag gccccctctg accctaa                   528


<210> SEQ ID NO 35
<211> LENGTH: 531
```

-continued

<212> TYPE: DNA
<213> ORGANISM: Amblyomma americanum

<400> SEQUENCE: 35
attccgcact tcgaagagct tcccatcgag gatcgcaccg cgctgctcaa agccggctgg 60
aacgaactgc ttattgccgc cttttcgcac cgttctgtgg cggtgcgcga cggcatcgtt 120
ctggccaccg ggctggtggt gcagcggcac agcgcacacg gcgcaggcgt tggcgacatc 180
ttcgaccgcg tactagccga gctggtggcc aagatgcgcg acatgaagat ggacaaaacg 240
gagctcggct gcctgcgcgc cgtggtgctc ttcaatccag acgccaaggg tctccgaaac 300
gccaccagag tagaggcgct ccgcgagaag gtgtatgcgg cgctggagga gcactgccgt 360
cggcaccacc cggaccaacc gggtcgcttc ggcaagctgc tgctgcggct gcctgccttg 420
cgcagcatcg ggctcaaatg cctcgagcat ctgttcttct tcaagctcat cggagacact 480
cccatagaca gcttcctgct caacatgctg gaggcaccgg cagaccccta g 531

<210> SEQ ID NO 36
<211> LENGTH: 552
<212> TYPE: DNA
<213> ORGANISM: Celuca pugilator

<400> SEQUENCE: 36
atcccacact tcacagacct tcccatagag gaccaagtgg tattactcaa agccgggtgg 60
aacgagttgc ttattgcctc attctcacac cgtagcatgg gcgtggagga tggcatcgtg 120
ctggccacag ggctcgtgat ccacagaagt agtgctcacc aggctggagt gggtgccata 180
tttgatcgtg tcctctctga gctggtggcc aagatgaagg agatgaagat tgacaagaca 240
gagctgggct gccttcgctc catcgtcctg ttcaacccag atgccaaagg actaaactgc 300
gtcaatgatg tggagatctt gcgtgagaag gtgtatgctg ccctggagga gtacacacga 360
accacttacc ctgatgaacc tggacgcttt gccaagttgc ttctgcgact tcctgcactc 420
aggtctatag gcctgaagtg tcttgagtac ctcttcctgt ttaagctgat tggagacact 480
cccctggaca gctacttgat gaagatgctc gtagacaacc caaatacaag cgtcactccc 540
cccaccagct ag 552

<210> SEQ ID NO 37
<211> LENGTH: 531
<212> TYPE: DNA
<213> ORGANISM: Tenebrio molitor

<400> SEQUENCE: 37
atacctcact ttacctcgtt gccgatgtcg gaccaggtgc ttttattgag ggcaggatgg 60
aatgaattgc tcatcgccgc attctcgcac agatctatac aggcgcagga tgccatcgtt 120
ctagccacgg ggttgacagt taacaaaacg tcggcgcacg ccgtgggcgt gggcaacatc 180
tacgaccgcg tcctctccga gctggtgaac aagatgaaag agatgaagat ggacaagacg 240
gagctgggct gcttgagagc catcatcctc tacaacccca cgtgtcgcgg catcaagtcc 300
gtgcaggaag tggagatgct gcgtgagaaa atttacggcg tgctggaaga gtacaccagg 360
accacccacc cgaacgagcc cggcaggttc gccaaactgc ttctgcgcct cccggccctc 420
aggtccatcg ggttgaaatg ttccgaacac ctctttttct tcaagctgat cggtgatgtt 480
ccaatagaca cgttcctgat ggagatgctg gagtctccgg cggacgctta g 531

<210> SEQ ID NO 38
<211> LENGTH: 531

<212> TYPE: DNA
<213> ORGANISM: Apis mellifera

<400> SEQUENCE: 38
atcccgcatt ttacctcgtt gccactggag gatcaggtac ttctgctcag ggccggttgg 60
aacgagttgc tgatagcctc cttttcccac cgttccatcg acgtgaagga cggtatcgtg 120
ctggcgacgg ggatcaccgt gcatcggaac tcggcgcagc aggccggcgt gggcacgata 180
ttcgaccgtg tcctctcgga gcttgtctcg aaaatgcgtg aaatgaagat ggacaggaca 240
gagcttggct gtctcagatc tataatactc ttcaatcccg aggttcgagg actgaaatcc 300
atccaggaag tgaccctgct ccgtgagaag atctacggcg ccctggaggg ttattgccgc 360
gtagcttggc ccgacgacgc tggaagattc gcgaaattac ttctacgcct gcccgccatc 420
cgctcgatcg gattaaagtg cctcgagtac ctgttcttct tcaaaatgat cggtgacgta 480
ccgatcgacg attttctcgt ggagatgtta gaatcgcgat cagatcctta g 531

<210> SEQ ID NO 39
<211> LENGTH: 176
<212> TYPE: PRT
<213> ORGANISM: Locusta migratoria

<400> SEQUENCE: 39

Ile Pro His Phe Thr Ser Leu Pro Leu Glu Asp Gln Val Leu Leu Leu
1 5 10 15

Arg Ala Gly Trp Asn Glu Leu Leu Ile Ala Ala Phe Ser His Arg Ser
20 25 30

Val Asp Val Lys Asp Gly Ile Val Leu Ala Thr Gly Leu Thr Val His
35 40 45

Arg Asn Ser Ala His Gln Ala Gly Val Gly Thr Ile Phe Asp Arg Val
50 55 60

Leu Thr Glu Leu Val Ala Lys Met Arg Glu Met Lys Met Asp Lys Thr
65 70 75 80

Glu Leu Gly Cys Leu Arg Ser Val Ile Leu Phe Asn Pro Glu Val Arg
85 90 95

Gly Leu Lys Ser Ala Gln Glu Val Glu Leu Leu Arg Glu Lys Val Tyr
100 105 110

Ala Ala Leu Glu Glu Tyr Thr Arg Thr Thr His Pro Asp Glu Pro Gly
115 120 125

Arg Phe Ala Lys Leu Leu Leu Arg Leu Pro Ser Leu Arg Ser Ile Gly
130 135 140

Leu Lys Cys Leu Glu His Leu Phe Phe Phe Arg Leu Ile Gly Asp Val
145 150 155 160

Pro Ile Asp Thr Phe Leu Met Glu Met Leu Glu Ser Pro Ser Asp Ser
165 170 175

<210> SEQ ID NO 40
<211> LENGTH: 175
<212> TYPE: PRT
<213> ORGANISM: Amblyomma americanum

<400> SEQUENCE: 40

Ile Pro His Phe Glu Glu Leu Pro Leu Glu Asp Arg Met Val Leu Leu
1 5 10 15

Lys Ala Gly Trp Asn Glu Leu Leu Ile Ala Ala Phe Ser His Arg Ser
20 25 30

Val Asp Val Arg Asp Gly Ile Val Leu Ala Thr Gly Leu Val Val Gln
35 40 45

```
Arg His Ser Ala His Gly Ala Gly Val Gly Ala Ile Phe Asp Arg Val
    50                  55                  60

Leu Thr Glu Leu Val Ala Lys Met Arg Glu Met Lys Met Asp Arg Thr
65                  70                  75                  80

Glu Leu Gly Cys Leu Leu Ala Val Val Leu Phe Asn Pro Glu Ala Lys
                85                  90                  95

Gly Leu Arg Thr Cys Pro Ser Gly Gly Pro Glu Gly Glu Ser Val Ser
            100                 105                 110

Ala Leu Glu Glu His Cys Arg Gln Gln Tyr Pro Asp Gln Pro Gly Arg
        115                 120                 125

Phe Ala Lys Leu Leu Leu Arg Leu Pro Ala Leu Arg Ser Ile Gly Leu
    130                 135                 140

Lys Cys Leu Glu His Leu Phe Phe Phe Lys Leu Ile Gly Asp Thr Pro
145                 150                 155                 160

Ile Asp Asn Phe Leu Leu Ser Met Leu Glu Ala Pro Ser Asp Pro
                165                 170                 175


<210> SEQ ID NO 41
<211> LENGTH: 176
<212> TYPE: PRT
<213> ORGANISM: Amblyomma americanum

<400> SEQUENCE: 41

Ile Pro His Phe Glu Glu Leu Pro Ile Glu Asp Arg Thr Ala Leu Leu
1               5                   10                  15

Lys Ala Gly Trp Asn Glu Leu Leu Ile Ala Ala Phe Ser His Arg Ser
            20                  25                  30

Val Ala Val Arg Asp Gly Ile Val Leu Ala Thr Gly Leu Val Val Gln
        35                  40                  45

Arg His Ser Ala His Gly Ala Gly Val Gly Asp Ile Phe Asp Arg Val
    50                  55                  60

Leu Ala Glu Leu Val Ala Lys Met Arg Asp Met Lys Met Asp Lys Thr
65                  70                  75                  80

Glu Leu Gly Cys Leu Arg Ala Val Val Leu Phe Asn Pro Asp Ala Lys
                85                  90                  95

Gly Leu Arg Asn Ala Thr Arg Val Glu Ala Leu Arg Glu Lys Val Tyr
            100                 105                 110

Ala Ala Leu Glu Glu His Cys Arg Arg His His Pro Asp Gln Pro Gly
        115                 120                 125

Arg Phe Gly Lys Leu Leu Leu Arg Leu Pro Ala Leu Arg Ser Ile Gly
    130                 135                 140

Leu Lys Cys Leu Glu His Leu Phe Phe Phe Lys Leu Ile Gly Asp Thr
145                 150                 155                 160

Pro Ile Asp Ser Phe Leu Leu Asn Met Leu Glu Ala Pro Ala Asp Pro
                165                 170                 175


<210> SEQ ID NO 42
<211> LENGTH: 183
<212> TYPE: PRT
<213> ORGANISM: Celuca pugilator

<400> SEQUENCE: 42

Ile Pro His Phe Thr Asp Leu Pro Ile Glu Asp Gln Val Val Leu Leu
1               5                   10                  15

Lys Ala Gly Trp Asn Glu Leu Leu Ile Ala Ser Phe Ser His Arg Ser
            20                  25                  30
```

```
Met Gly Val Glu Asp Gly Ile Val Leu Ala Thr Gly Leu Val Ile His
        35                  40                  45

Arg Ser Ser Ala His Gln Ala Gly Val Gly Ala Ile Phe Asp Arg Val
    50                  55                  60

Leu Ser Glu Leu Val Ala Lys Met Lys Glu Met Lys Ile Asp Lys Thr
65                  70                  75                  80

Glu Leu Gly Cys Leu Arg Ser Ile Val Leu Phe Asn Pro Asp Ala Lys
                85                  90                  95

Gly Leu Asn Cys Val Asn Asp Val Glu Ile Leu Arg Glu Lys Val Tyr
            100                 105                 110

Ala Ala Leu Glu Glu Tyr Thr Arg Thr Thr Tyr Pro Asp Glu Pro Gly
        115                 120                 125

Arg Phe Ala Lys Leu Leu Leu Arg Leu Pro Ala Leu Arg Ser Ile Gly
    130                 135                 140

Leu Lys Cys Leu Glu Tyr Leu Phe Leu Phe Lys Leu Ile Gly Asp Thr
145                 150                 155                 160

Pro Leu Asp Ser Tyr Leu Met Lys Met Leu Val Asp Asn Pro Asn Thr
                165                 170                 175

Ser Val Thr Pro Pro Thr Ser
            180


<210> SEQ ID NO 43
<211> LENGTH: 176
<212> TYPE: PRT
<213> ORGANISM: Tenebrio molitor

<400> SEQUENCE: 43

Ile Pro His Phe Thr Ser Leu Pro Met Ser Asp Gln Val Leu Leu Leu
1               5                   10                  15

Arg Ala Gly Trp Asn Glu Leu Leu Ile Ala Ala Phe Ser His Arg Ser
            20                  25                  30

Ile Gln Ala Gln Asp Ala Ile Val Leu Ala Thr Gly Leu Thr Val Asn
        35                  40                  45

Lys Thr Ser Ala His Ala Val Gly Val Gly Asn Ile Tyr Asp Arg Val
    50                  55                  60

Leu Ser Glu Leu Val Asn Lys Met Lys Glu Met Lys Met Asp Lys Thr
65                  70                  75                  80

Glu Leu Gly Cys Leu Arg Ala Ile Ile Leu Tyr Asn Pro Thr Cys Arg
                85                  90                  95

Gly Ile Lys Ser Val Gln Glu Val Glu Met Leu Arg Glu Lys Ile Tyr
            100                 105                 110

Gly Val Leu Glu Glu Tyr Thr Arg Thr Thr His Pro Asn Glu Pro Gly
        115                 120                 125

Arg Phe Ala Lys Leu Leu Leu Arg Leu Pro Ala Leu Arg Ser Ile Gly
    130                 135                 140

Leu Lys Cys Ser Glu His Leu Phe Phe Phe Lys Leu Ile Gly Asp Val
145                 150                 155                 160

Pro Ile Asp Thr Phe Leu Met Glu Met Leu Glu Ser Pro Ala Asp Ala
                165                 170                 175


<210> SEQ ID NO 44
<211> LENGTH: 176
<212> TYPE: PRT
<213> ORGANISM: Apis mellifera

<400> SEQUENCE: 44

Ile Pro His Phe Thr Ser Leu Pro Leu Glu Asp Gln Val Leu Leu Leu
```

-continued

```
1               5                   10                  15

Arg Ala Gly Trp Asn Glu Leu Leu Ile Ala Ser Phe Ser His Arg Ser
            20                  25                  30

Ile Asp Val Lys Asp Gly Ile Val Leu Ala Thr Gly Ile Thr Val His
        35                  40                  45

Arg Asn Ser Ala Gln Gln Ala Gly Val Gly Thr Ile Phe Asp Arg Val
    50                  55                  60

Leu Ser Glu Leu Val Ser Lys Met Arg Glu Met Lys Met Asp Arg Thr
65                  70                  75                  80

Glu Leu Gly Cys Leu Arg Ser Ile Ile Leu Phe Asn Pro Glu Val Arg
                85                  90                  95

Gly Leu Lys Ser Ile Gln Glu Val Thr Leu Leu Arg Glu Lys Ile Tyr
            100                 105                 110

Gly Ala Leu Glu Gly Tyr Cys Arg Val Ala Trp Pro Asp Asp Ala Gly
        115                 120                 125

Arg Phe Ala Lys Leu Leu Leu Arg Leu Pro Ala Ile Arg Ser Ile Gly
    130                 135                 140

Leu Lys Cys Leu Glu Tyr Leu Phe Phe Phe Lys Met Ile Gly Asp Val
145                 150                 155                 160

Pro Ile Asp Asp Phe Leu Val Glu Met Leu Glu Ser Arg Ser Asp Pro
                165                 170                 175


<210> SEQ ID NO 45
<211> LENGTH: 711
<212> TYPE: DNA
<213> ORGANISM: Artificial Sequence
<220> FEATURE:
<223> OTHER INFORMATION: Chimeric RXR ligand binding domain

<400> SEQUENCE: 45

gccaacgagg acatgcctgt agagaagatt ctggaagccg agcttgctgt cgagcccaag      60

actgagacat acgtggaggc aaacatgggg ctgaacccca gctcaccaaa tgaccctgtt     120

accaacatct gtcaagcagc agacaagcag ctcttcactc ttgtggagtg ggccaagagg     180

atcccacact tttctgagct gcccctagac gaccaggtca tcctgctacg ggcaggctgg     240

aacgagctgc tgatcgcctc cttctcccac cgctccatag ctgtgaaaga tgggattctc     300

ctggccaccg gcctgcacgt acaccggaac agcgctcaca gtgctggggt gggcgccatc     360

tttgacaggg tgctaacaga gctggtgtct aagatgcgtg acatgcagat ggacaagact     420

gaacttggct gcttgcgatc tgttattctt ttcaatccag aggtgagggg tttgaaatcc     480

gcccaggaag ttgaacttct acgtgaaaaa gtatatgccg ctttggaaga atatactaga     540

acaacacatc ccgatgaacc aggaagattt gcaaaacttt tgcttcgtct gccttcttta     600

cgttccatag gccttaagtg tttggagcat ttgtttttct ttcgccttat tggagatgtt     660

ccaattgata cgttcctgat ggagatgctt gaatcacctt ctgattcata a              711


<210> SEQ ID NO 46
<211> LENGTH: 236
<212> TYPE: PRT
<213> ORGANISM: Artificial Sequence
<220> FEATURE:
<223> OTHER INFORMATION: Chimeric RXR ligand binding domain

<400> SEQUENCE: 46

Ala Asn Glu Asp Met Pro Val Glu Lys Ile Leu Glu Ala Glu Leu Ala
1               5                   10                  15

Val Glu Pro Lys Thr Glu Thr Tyr Val Glu Ala Asn Met Gly Leu Asn
```

```
            20                  25                  30

Pro Ser Ser Pro Asn Asp Pro Val Thr Asn Ile Cys Gln Ala Ala Asp
        35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ser Val Ile Leu Phe Asn Pro Glu Val Arg Gly Leu Lys Ser
145                 150                 155                 160

Ala Gln Glu Val Glu Leu Leu Arg Glu Lys Val Tyr Ala Ala Leu Glu
                165                 170                 175

Glu Tyr Thr Arg Thr Thr His Pro Asp Glu Pro Gly Arg Phe Ala Lys
            180                 185                 190

Leu Leu Leu Arg Leu Pro Ser Leu Arg Ser Ile Gly Leu Lys Cys Leu
        195                 200                 205

Glu His Leu Phe Phe Phe Arg Leu Ile Gly Asp Val Pro Ile Asp Thr
    210                 215                 220

Phe Leu Met Glu Met Leu Glu Ser Pro Ser Asp Ser
225                 230                 235


<210> SEQ ID NO 47
<211> LENGTH: 441
<212> TYPE: DNA
<213> ORGANISM: Saccharomyces cerevisiae

<400> SEQUENCE: 47

atgaagctac tgtcttctat cgaacaagca tgcgatattt gccgacttaa aaagctcaag      60

tgctccaaag aaaaaccgaa gtgcgccaag tgtctgaaga acaactggga gtgtcgctac     120

tctcccaaaa ccaaaaggtc tccgctgact agggcacatc tgacagaagt ggaatcaagg     180

ctagaaagac tggaacagct atttctactg atttttcctc gagaagacct tgacatgatt     240

ttgaaaatgg attctttaca ggatataaaa gcattgttaa caggattatt tgtacaagat     300

aatgtgaata aagatgccgt cacagataga ttggcttcag tggagactga tatgcctcta     360

acattgagac agcatagaat aagtgcgaca tcatcatcgg aagagagtag taacaaaggt     420

caaagacagt tgactgtatc g                                               441


<210> SEQ ID NO 48
<211> LENGTH: 147
<212> TYPE: PRT
<213> ORGANISM: Saccharomyces cerevisiae

<400> SEQUENCE: 48

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
```

```
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145


<210> SEQ ID NO 49
<211> LENGTH: 606
<212> TYPE: DNA
<213> ORGANISM: Escherichia coli

<400> SEQUENCE: 49

atgaaagcgt taacggccag gcaacaagag gtgtttgatc tcatccgtga tcacatcagc      60

cagacaggta tgccgccgac gcgtgcggaa atcgcgcagc gtttggggtt ccgttcccca     120

aacgcggctg aagaacatct gaaggcgctg gcacgcaaag gcgttattga aattgtttcc     180

ggcgcatcac gcgggattcg tctgttgcag gaagaggaag aagggttgcc gctggtaggt     240

cgtgtggctg ccggtgaacc acttctggcg caacagcata ttgaaggtca ttatcaggtc     300

gatccttcct tattcaagcc gaatgctgat ttcctgctgc gcgtcagcgg gatgtcgatg     360

aaagatatcg gcattatgga tggtgacttg ctggcagtgc ataaaactca ggatgtacgt     420

aacggtcagg tcgttgtcgc acgtattgat gacgaagtta ccgttaagcg cctgaaaaaa     480

cagggcaata aagtcgaact gttgccagaa aatagcgagt ttaaaccaat tgtcgtagat     540

cttcgtcagc agagcttcac cattgaaggg ctggcggttg ggttattcg caacggcgac      600

tggctg                                                                606


<210> SEQ ID NO 50
<211> LENGTH: 202
<212> TYPE: PRT
<213> ORGANISM: Escherichia coli

<400> SEQUENCE: 50

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
```

```
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

```
<210> SEQ ID NO 51
<211> LENGTH: 271
<212> TYPE: DNA
<213> ORGANISM: herpes simplex virus 7

<400> SEQUENCE: 51

atgggcccta aaaagaagcg taaagtcgcc cccccgaccg atgtcagcct gggggacgag      60

ctccacttag acggcgagga cgtggcgatg gcgcatgccg acgcgctaga cgatttcgat     120

ctggacatgt tgggggacgg ggattccccg ggccgggat ttacccccca cgactccgcc     180

ccctacggcg ctctggatat ggccgacttc gagtttgagc agatgtttac cgatgccctt     240

ggaattgacg agtacggtgg ggaattcccg g                                   271
```

```
<210> SEQ ID NO 52
<211> LENGTH: 90
<212> TYPE: PRT
<213> ORGANISM: herpes simplex virus 7

<400> SEQUENCE: 52

Met Gly Pro Lys Lys Lys Arg Lys Val Ala Pro Pro Thr Asp Val Ser
1               5                   10                  15

Leu Gly Asp Glu Leu His Leu Asp Gly Glu Asp Val Ala Met Ala His
            20                  25                  30

Ala Asp Ala Leu Asp Asp Phe Asp Leu Asp Met Leu Gly Asp Gly Asp
        35                  40                  45

Ser Pro Gly Pro Gly Phe Thr Pro His Asp Ser Ala Pro Tyr Gly Ala
    50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90
```

```
<210> SEQ ID NO 53
<211> LENGTH: 307
<212> TYPE: DNA
<213> ORGANISM: Saccharomyces cerevisiae

<400> SEQUENCE: 53

atgggtgctc ctccaaaaaa gaagagaaag gtagctggta tcaataaaga tatcgaggag      60

tgcaatgcca tcattgagca gtttatcgac tacctgcgca ccggacagga gatgccgatg     120

gaaatggcgg atcaggcgat taacgtggtg ccgggcatga cgccgaaaac cattcttcac     180

gccgggccgc cgatccagcc tgactggctg aaatcgaatg gttttcatga aattgaagcg     240
```

gatgttaacg ataccagcct cttgctgagt ggagatgcct cctaccctta tgatgtgcca 300
gattatg 307

<210> SEQ ID NO 54
<211> LENGTH: 102
<212> TYPE: PRT
<213> ORGANISM: Saccharomyces cerevisiae

<400> SEQUENCE: 54

Met Gly Ala Pro Pro Lys Lys Lys Arg Lys Val Ala Gly Ile Asn Lys
1 5 10 15

Asp Ile Glu Glu Cys Asn Ala Ile Ile Glu Gln Phe Ile Asp Tyr Leu
20 25 30

Arg Thr Gly Gln Glu Met Pro Met Glu Met Ala Asp Gln Ala Ile Asn
35 40 45

Val Val Pro Gly Met Thr Pro Lys Thr Ile Leu His Ala Gly Pro Pro
50 55 60

Ile Gln Pro Asp Trp Leu Lys Ser Asn Gly Phe His Glu Ile Glu Ala
65 70 75 80

Asp Val Asn Asp Thr Ser Leu Leu Leu Ser Gly Asp Ala Ser Tyr Pro
85 90 95

Tyr Asp Val Pro Asp Tyr
100

<210> SEQ ID NO 55
<211> LENGTH: 19
<212> TYPE: DNA
<213> ORGANISM: Artificial Sequence
<220> FEATURE:
<223> OTHER INFORMATION: GAL4 response element

<400> SEQUENCE: 55
ggagtactgt cctccgagc 19

<210> SEQ ID NO 56
<211> LENGTH: 36
<212> TYPE: DNA
<213> ORGANISM: Artificial Sequence
<220> FEATURE:
<223> OTHER INFORMATION: 2xLexAop response element

<400> SEQUENCE: 56
ctgctgtata taaaaccagt ggttatatgt acagta 36

<210> SEQ ID NO 57
<211> LENGTH: 334
<212> TYPE: PRT
<213> ORGANISM: Choristoneura fumiferana

<400> SEQUENCE: 57

Pro Glu Cys Val Val Pro Glu Thr Gln Cys Ala Met Lys Arg Lys Glu
1 5 10 15

Lys Lys Ala Gln Lys Glu Lys Asp Lys Leu Pro Val Ser Thr Thr Thr
20 25 30

Val Asp Asp His Met Pro Pro Ile Met Gln Cys Glu Pro Pro Pro Pro
35 40 45

Glu Ala Ala Arg Ile His Glu Val Val Pro Arg Phe Leu Ser Asp Lys
50 55 60

Leu Leu Glu Thr Asn Arg Gln Lys Asn Ile Pro Gln Leu Thr Ala Asn
65 70 75 80

```
Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285

Gly Met Gln Asn Ser Asn Met Cys Ile Ser Leu Lys Leu Lys Asn Arg
    290                 295                 300

Lys Leu Pro Pro Phe Leu Glu Glu Ile Trp Asp Val Ala Asp Met Ser
305                 310                 315                 320

His Thr Gln Pro Pro Pro Ile Leu Glu Ser Pro Thr Asn Leu
                325                 330


<210> SEQ ID NO 58
<211> LENGTH: 549
<212> TYPE: PRT
<213> ORGANISM: Drosophila melanogaster

<400> SEQUENCE: 58

Arg Pro Glu Cys Val Val Pro Glu Asn Gln Cys Ala Met Lys Arg Arg
1               5                   10                  15

Glu Lys Lys Ala Gln Lys Glu Lys Asp Lys Met Thr Thr Ser Pro Ser
            20                  25                  30

Ser Gln His Gly Gly Asn Gly Ser Leu Ala Ser Gly Gly Gly Gln Asp
        35                  40                  45

Phe Val Lys Lys Glu Ile Leu Asp Leu Met Thr Cys Glu Pro Pro Gln
    50                  55                  60

His Ala Thr Ile Pro Leu Leu Pro Asp Glu Ile Leu Ala Lys Cys Gln
65                  70                  75                  80

Ala Arg Asn Ile Pro Ser Leu Thr Tyr Asn Gln Leu Ala Val Ile Tyr
                85                  90                  95

Lys Leu Ile Trp Tyr Gln Asp Gly Tyr Glu Gln Pro Ser Glu Glu Asp
            100                 105                 110

Leu Arg Arg Ile Met Ser Gln Pro Asp Glu Asn Glu Ser Gln Thr Asp
        115                 120                 125
```

```
Val Ser Phe Arg His Ile Thr Glu Ile Thr Ile Leu Thr Val Gln Leu
    130                 135                 140

Ile Val Glu Phe Ala Lys Gly Leu Pro Ala Phe Thr Lys Ile Pro Gln
145                 150                 155                 160

Glu Asp Gln Ile Thr Leu Leu Lys Ala Cys Ser Ser Glu Val Met Met
                165                 170                 175

Leu Arg Met Ala Arg Arg Tyr Asp His Ser Ser Asp Ser Ile Phe Phe
            180                 185                 190

Ala Asn Asn Arg Ser Tyr Thr Arg Asp Ser Tyr Lys Met Ala Gly Met
        195                 200                 205

Ala Asp Asn Ile Glu Asp Leu Leu His Phe Cys Arg Gln Met Phe Ser
    210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
            260                 265                 270

Cys Gly Asp Ser Met Ser Leu Val Phe Tyr Ala Lys Leu Leu Ser Ile
        275                 280                 285

Leu Thr Glu Leu Arg Thr Leu Gly Asn Gln Asn Ala Glu Met Cys Phe
    290                 295                 300

Ser Leu Lys Leu Lys Asn Arg Lys Leu Pro Lys Phe Leu Glu Glu Ile
305                 310                 315                 320

Trp Asp Val His Ala Ile Pro Pro Ser Val Gln Ser His Leu Gln Ile
                325                 330                 335

Thr Gln Glu Glu Asn Glu Arg Leu Glu Arg Ala Glu Arg Met Arg Ala
            340                 345                 350

Ser Val Gly Gly Ala Ile Thr Ala Gly Ile Asp Cys Asp Ser Ala Ser
        355                 360                 365

Thr Ser Ala Ala Ala Ala Ala Ala Gln His Gln Pro Gln Pro Gln Pro
    370                 375                 380

Gln Pro Gln Pro Ser Ser Leu Thr Gln Asn Asp Ser Gln His Gln Thr
385                 390                 395                 400

Gln Pro Gln Leu Gln Pro Gln Leu Pro Pro Gln Leu Gln Gly Gln Leu
                405                 410                 415

Gln Pro Gln Leu Gln Pro Gln Leu Gln Thr Gln Leu Gln Pro Gln Ile
            420                 425                 430

Gln Pro Gln Pro Gln Leu Leu Pro Val Ser Ala Pro Val Pro Ala Ser
        435                 440                 445

Val Thr Ala Pro Gly Ser Leu Ser Ala Val Ser Thr Ser Ser Glu Tyr
    450                 455                 460

Met Gly Gly Ser Ala Ala Ile Gly Pro Ile Thr Pro Ala Thr Thr Ser
465                 470                 475                 480

Ser Ile Thr Ala Ala Val Thr Ala Ser Ser Thr Thr Ser Ala Val Pro
                485                 490                 495

Met Gly Asn Gly Val Gly Val Gly Val Gly Val Gly Gly Asn Val Ser
            500                 505                 510

Met Tyr Ala Asn Ala Gln Thr Ala Met Ala Leu Met Gly Val Ala Leu
        515                 520                 525

His Ser His Gln Glu Gln Leu Ile Gly Gly Val Ala Val Lys Ser Glu
    530                 535                 540

His Ser Thr Thr Ala
545
```

<210> SEQ ID NO 59
<211> LENGTH: 1288
<212> TYPE: DNA
<213> ORGANISM: Choristoneura fumiferana

<400> SEQUENCE: 59

```
aagggccctg cgccccgtca gcaagaggaa ctgtgtctgg tatgcgggga cagagcctcc     60
ggataccact acaatgcgct cacgtgtgaa gggtgtaaag ggttcttcag acggagtgtt    120
accaaaaatg cggtttatat ttgtaaattc ggtcacgctt gcgaaatgga catgtacatg    180
cgacggaaat gccaggagtg ccgcctgaag aagtgcttag ctgtaggcat gaggcctgag    240
tgcgtagtac ccgagactca gtgcgccatg aagcggaaag agaagaaagc acagaaggag    300
aaggacaaac tgcctgtcag cacgacgacg gtggacgacc acatgccgcc cattatgcag    360
tgtgaacctc cacctcctga agcagcaagg attcacgaag tggtcccaag gtttctctcc    420
gacaagctgt tggagacaaa ccggcagaaa aacatccccc agttgacagc caaccagcag    480
ttccttatcg ccaggctcat ctggtaccag gacgggtacg agcagccttc tgatgaagat    540
ttgaagagga ttacgcagac gtggcagcaa gcggacgatg aaaacgaaga gtctgacact    600
cccttccgcc agatcacaga gatgactatc ctcacggtcc aacttatcgt ggagttcgcg    660
aagggattgc cagggttcgc caagatctcg cagcctgatc aaattacgct gcttaaggct    720
tgctcaagtg aggtaatgat gctccgagtc gcgcgacgat acgatgcggc ctcagacagt    780
gttctgttcg cgaacaacca agcgtacact cgcgacaact accgcaaggc tggcatggcc    840
tacgtcatcg aggatctact gcacttctgc cggtgcatgt actctatggc gttggacaac    900
atccattacg cgctgctcac ggctgtcgtc atcttttctg accggccagg gttggagcag    960
ccgcaactgg tggaagaaat ccagcggtac tacctgaata cgctccgcat ctatatcctg   1020
aaccagctga gcgggtcggc gcgttcgtcc gtcatatacg gcaagatcct ctcaatcctc   1080
tctgagctac gcacgctcgg catgcaaaac tccaacatgt gcatctccct caagctcaag   1140
aacagaaagc tgccgccttt cctcgaggag atctgggatg tggcggacat gtcgcacacc   1200
caaccgccgc ctatcctcga gtcccccacg aatctctagc cctgcgcgc acgcatcgcc   1260
gatgccgcgt ccggccgcgc tgctctga                                      1288
```

<210> SEQ ID NO 60
<211> LENGTH: 309
<212> TYPE: DNA
<213> ORGANISM: Simian virus 40

<400> SEQUENCE: 60

```
ggtgtggaaa gtccccaggc tccccagcag gcagaagtat gcaaagcatg catctcaatt     60
agtcagcaac caggtgtgga aagtccccag gctccccagc aggcagaagt atgcaaagca    120
tgcatctcaa ttagtcagca accatagtcc cgcccctaac tccgcccatc ccgcccctaa    180
ctccgcccag ttccgcccat tctccgcccc atggctgact aatttttttt atttatgcag    240
aggccgaggc cgcctcggcc tctgagctat tccagaagta gtgaggaggc ttttttggag    300
gcctaggct                                                            309
```

<210> SEQ ID NO 61
<211> LENGTH: 24
<212> TYPE: DNA
<213> ORGANISM: Artificial Sequence
<220> FEATURE:
<223> OTHER INFORMATION: synthetic E1b minimal promoter

<400> SEQUENCE: 61
tatataatgg atccccgggt accg 24

<210> SEQ ID NO 62
<211> LENGTH: 1653
<212> TYPE: DNA
<213> ORGANISM: Artificial Sequence
<220> FEATURE:
<223> OTHER INFORMATION: luciferase gene

<400> SEQUENCE: 62
atggaagacg ccaaaaacat aaagaaaggc ccggcgccat tctatcctct agaggatgga 60
accgctggag agcaactgca taaggctatg aagagatacg ccctggttcc tggaacaatt 120
gcttttacag atgcacatat cgaggtgaac atcacgtacg cggaatactt cgaaatgtcc 180
gttcggttgg cagaagctat gaaacgatat gggctgaata caaatcacag aatcgtcgta 240
tgcagtgaaa actctcttca attctttatg ccggtgttgg gcgcgttatt tatcggagtt 300
gcagttgcgc ccgcgaacga catttataat gaacgtgaat tgctcaacag tatgaacatt 360
tcgcagccta ccgtagtgtt tgtttccaaa aaggggttgc aaaaaatttt gaacgtgcaa 420
aaaaaattac caataatcca gaaaattatt atcatggatt ctaaaacgga ttaccaggga 480
tttcagtcga tgtacacgtt cgtcacatct catctacctc ccggttttaa tgaatacgat 540
tttgtaccag agtcctttga tcgtgacaaa acaattgcac tgataatgaa ttcctctgga 600
tctactgggt tacctaaggg tgtggccctt ccgcatagaa ctgcctgcgt cagattctcg 660
catgccagag atcctatttt tggcaatcaa atcattccgg atactgcgat tttaagtgtt 720
gttccattcc atcacggttt tggaatgttt actacactcg gatatttgat atgtggattt 780
cgagtcgtct taatgtatag atttgaagaa gagctgtttt tacgatccct tcaggattac 840
aaaattcaaa gtgcgttgct agtaccaacc ctattttcat tcttcgccaa aagcactctg 900
attgacaaat acgatttatc taatttacac gaaattgctt ctgggggcgc acctctttcg 960
aaagaagtcg gggaagcggt tgcaaaacgc ttccatcttc cagggatacg acaaggatat 1020
gggctcactg agactacatc agctattctg attacacccg agggggatga taaaccgggc 1080
gcggtcggta aagttgttcc attttttgaa gcgaaggttg tggatctgga taccgggaaa 1140
acgctgggcg ttaatcagag aggcgaatta tgtgtcagag gacctatgat tatgtccggt 1200
tatgtaaaca atccggaagc gaccaacgcc ttgattgaca aggatggatg gctacattct 1260
ggagacatag cttactggga cgaagacgaa cacttcttca tagttgaccg cttgaagtct 1320
ttaattaaat acaaaggata tcaggtggcc cccgctgaat tggaatcgat attgttacaa 1380
caccccaaca tcttcgacgc gggcgtggca ggtcttcccg acgatgacgc cggtgaactt 1440
cccgccgccg ttgttgtttt ggagcacgga aagacgatga cggaaaaaga gatcgtggat 1500
tacgtcgcca gtcaagtaac aaccgcgaaa aagttgcgcg gaggagttgt gtttgtggac 1560
gaagtaccga aaggtcttac cggaaaactc gacgcaagaa aaatcagaga gatcctcata 1620
aaggccaaga agggcggaaa gtccaaattg taa 1653

<210> SEQ ID NO 63
<211> LENGTH: 18
<212> TYPE: DNA
<213> ORGANISM: Mus musculus

<400> SEQUENCE: 63
ccacatcaag ccacctag 18

<210> SEQ ID NO 64
<211> LENGTH: 18
<212> TYPE: DNA
<213> ORGANISM: Locusta migratoria

<400> SEQUENCE: 64
tcaccttctg attcataa 18

<210> SEQ ID NO 65
<211> LENGTH: 1054
<212> TYPE: DNA
<213> ORGANISM: Choristoneura fumiferana

<400> SEQUENCE: 65
cctgagtgcg tagtacccga gactcagtgc gccatgaagc ggaaagagaa gaaagcacag 60
aaggagaagg acaaactgcc tgtcagcacg acgacggtgg acgaccacat gccgcccatt 120
atgcagtgtg aacctccacc tcctgaagca gcaaggattc acgaagtggt cccaaggttt 180
ctctccgaca agctgttgga gacaaaccgg cagaaaaaca tcccccagtt gacagccaac 240
cagcagttcc ttatcgccag gctcatctgg taccaggacg ggtacgagca gccttctgat 300
gaagatttga agaggattac gcagacgtgg cagcaagcgg acgatgaaaa cgaagagtct 360
gacactccct tccgccagat cacagagatg actatcctca cggtccaact tatcgtggag 420
ttcgcgaagg gattgccagg gttcgccaag atctcgcagc ctgatcaaat tacgctgctt 480
aaggcttgct caagtgaggt aatgatgctc cgagtcgcgc gacgatacga tgcggcctca 540
gacagtgttc tgttcgcgaa caaccaagcg tacactcgcg acaactaccg caaggctggc 600
atggcctacg tcatcgagga tctactgcac ttctgccggt gcatgtactc tatggcgttg 660
gacaacatcc attacgcgct gctcacggct gtcgtcatct ttctgaccg gccagggttg 720 gagcagccgc aactggtgga agaaatccag cggtactacc tgaatacgct ccgcatctat 780
atcctgaacc agctgagcgg gtcggcgcgt tcgtccgtca tatacggcaa gatcctctca 840
atcctctctg agctacgcac gctcggcatg caaaactcca acatgtgcat ctccctcaag 900
ctcaagaaca gaaagctgcc gcctttcctc gaggagatct gggatgtggc ggacatgtcg 960
cacacccaac cgccgcctat cctcgagtcc cccacgaatc tctagcccct gcgcgcacgc 1020
atcgccgatg ccgcgtccgg ccgcgctgct ctga 1054

<210> SEQ ID NO 66
<211> LENGTH: 798
<212> TYPE: DNA
<213> ORGANISM: Choristoneura fumiferana

<400> SEQUENCE: 66
tcggtgcagg taagcgatga gctgtcaatc gagcgcctaa cggagatgga gtctttggtg 60
gcagatccca gcgaggagtt ccagttcctc cgcgtggggc ctgacagcaa cgtgcctcca 120
cgttaccgcg cgcccgtctc ctccctctgc caaataggca acaagcaaat agcggcgttg 180
gtggtatggg cgcgcgacat ccctcatttc gggcagctgg agctggacga tcaagtggta 240
ctcatcaagg cctcctggaa tgagctgcta ctcttcgcca tcgcctggcg ctctatggag 300
tatttggaag atgagaggga gaacggggac ggaacgcgga gcaccactca gccacaactg 360
atgtgtctca tgcctggcat gacgttgcac cgcaactcgg cgcagcaggc gggcgtgggc 420
gccatcttcg accgcgtgct gtccgagctc agtctgaaga tgcgcacctt gcgcatggac 480
caggccgagt acgtcgcgct caaagccatc gtgctgctca accctgatgt gaaaggactg 540
aagaatcggc aagaagttga cgttttgcga gaaaaaatgt tctcttgcct ggacgactac 600
tgccggcggt cgcgaagcaa cgaggaaggc cggtttgcgt ccttgctgct gcggctgcca 660
gctctccgct ccatctcgct caagagcttc gaacacctct acttcttcca cctcgtggcc 720
gaaggctcca tcagcggata catacgagag gcgctccgaa accacgcgcc tccgatcgac 780
gtcaatgcca tgatgtaa 798

<210> SEQ ID NO 67
<211> LENGTH: 1650
<212> TYPE: DNA
<213> ORGANISM: Drosophila melanogaster

<400> SEQUENCE: 67
cggccggaat gcgtcgtccc ggagaaccaa tgtgcgatga agcggcgcga aaagaaggcc 60
cagaaggaga aggacaaaat gaccacttcg ccgagctctc agcatggcgg caatggcagc 120
ttggcctctg gtggcggcca agactttgtt aagaaggaga ttcttgacct tatgacatgc 180
gagccgcccc agcatgccac tattccgcta ctacctgatg aaatattggc caagtgtcaa 240
gcgcgcaata taccttcctt aacgtacaat cagttggccg ttatatacaa gttaatttgg 300
taccaggatg gctatgagca gccatctgaa gaggatctca ggcgtataat gagtcaaccc 360
gatgagaacg agagccaaac ggacgtcagc tttcggcata taaccgagat aaccatactc 420
acggtccagt tgattgttga gtttgctaaa ggtctaccag cgtttacaaa gataccccag 480
gaggaccaga tcacgttact aaaggcctgc tcgtcggagg tgatgatgct gcgtatggca 540
cgacgctatg accacagctc ggactcaata ttcttcgcga ataatagatc atatacgcgg 600
gattcttaca aaatggccgg aatggctgat aacattgaag acctgctgca tttctgccgc 660
caaatgttct cgatgaaggt ggacaacgtc gaatacgcgc ttctcactgc cattgtgatc 720
ttctcggacc ggccgggcct ggagaaggcc caactagtcg aagcgatcca gagctactac 780
atcgacacgc tacgcattta tatactcaac cgccactgcg gcgactcaat gagcctcgtc 840
ttctacgcaa agctgctctc gatcctcacc gagctgcgta cgctgggcaa ccagaacgcc 900
gagatgtgtt tctcactaaa gctcaaaaac cgcaaactgc ccaagttcct cgaggagatc 960
tgggacgttc atgccatccc gccatcggtc cagtcgcacc ttcagattac ccaggaggag 1020
aacgagcgtc tcgagcgggc tgagcgtatg cgggcatcgg ttgggggcgc cattaccgcc 1080
ggcattgatt gcgactctgc ctccacttcg gcggcggcag ccgcggccca gcatcagcct 1140
cagcctcagc cccagcccca accctcctcc ctgacccaga acgattccca gcaccagaca 1200
cagccgcagc tacaacctca gctaccacct cagctgcaag gtcaactgca accccagctc 1260
caaccacagc ttcagacgca actccagcca cagattcaac cacagccaca gctccttccc 1320
gtctccgctc ccgtgcccgc ctccgtaacc gcacctggtt ccttgtccgc ggtcagtacg 1380
agcagcgaat acatgggcgg aagtgcggcc ataggaccca tcacgccggc aaccaccagc 1440
agtatcacgg ctgccgttac cgctagctcc accacatcag cggtaccgat gggcaacgga 1500
gttggagtcg gtgttggggt gggcggcaac gtcagcatgt atgcgaacgc ccagacggcg 1560
atggccttga tgggtgtagc cctgcattcg caccaagagc agcttatcgg gggagtggcg 1620
gttaagtcgg agcactcgac gactgcatag 1650

<210> SEQ ID NO 68
<211> LENGTH: 1586
<212> TYPE: DNA
<213> ORGANISM: Bamecia argentifoli

<400> SEQUENCE: 68
gaattcgcgg ccgctcgcaa acttccgtac ctctcacccc ctcgccagga ccccccgcca 60
accagttcac cgtcatctcc tccaatggat actcatcccc catgtcttcg ggcagctacg 120
acccttatag tcccaccaat ggaagaatag ggaaagaaga gctttcgccg gcgaatagtc 180
tgaacgggta caacgtggat agctgcgatg cgtcgcggaa gaagaaggga ggaacgggtc 240
ggcagcagga ggagctgtgt ctcgtctgcg gggaccgcgc ctccggctac cactacaacg 300
ccctcacctg cgaaggctgc aagggcttct tccgtcggag catcaccaag aatgccgtct 360
accagtgtaa atatggaaat aattgtgaaa ttgacatgta catgaggcga aaatgccaag 420
agtgtcgtct caagaagtgt ctcagcgttg gcatgaggcc agaatgtgta gttcccgaat 480
tccagtgtgc tgtgaagcga aaagagaaaa aagcgcaaaa ggacaaagat aaacctaact 540
caacgacgag ttgttctcca gatggaatca aacaagagat agatcctcaa aggctggata 600
cagattcgca gctattgtct gtaaatggag ttaaacccat tactccagag caagaagagc 660
tcatccatag gctagtttat tttcaaaatg aatatgaaca tccatcccca gaggatatca 720
aaaggatagt taatgctgca ccagaagaag aaaatgtagc tgaagaaagg tttaggcata 780
ttacagaaat tacaattctc actgtacagt taattgtgga attttctaag cgattacctg 840
gttttgacaa actaattcgt gaagatcaaa tagctttatt aaaggcatgt agtagtgaag 900
taatgatgtt tagaatggca aggaggtatg atgctgaaac agattcgata ttgtttgcaa 960
ctaaccagcc gtatacgaga gaatcataca ctgtagctgg catgggtgat actgtggagg 1020
atctgctccg attttgtcga catatgtgtg ccatgaaagt cgataacgca gaatatgctc 1080
ttctcactgc cattgtaatt ttttcagaac gaccatctct aagtgaaggc tggaaggttg 1140
agaagattca agaaatttac atagaagcat taaaagcata tgttgaaaat cgaaggaaac 1200
catatgcaac aaccattttt gctaagttac tatctgtttt aactgaacta cgaacattag 1260
ggaatatgaa ttcagaaaca tgcttctcat tgaagctgaa gaatagaaag gtgccatcct 1320
tcctcgagga gatttgggat gttgtttcat aaacagtctt acctcaattc catgttactt 1380
ttcatatttg atttatctca gcaggtggct cagtacttat cctcacatta ctgagctcac 1440
ggtatgctca tacaattata acttgtaata tcatatcggt gatgacaaat ttgttacaat 1500
attctttgtt accttaacac aatgttgatc tcataatgat gtatgaattt ttctgttttt 1560
gcaaaaaaaa aagcggccgc gaattc 1586

<210> SEQ ID NO 69
<211> LENGTH: 1109
<212> TYPE: DNA
<213> ORGANISM: Nephotetix cincticeps

<400> SEQUENCE: 69
caggaggagc tctgcctgtt gtgcggagac cgagcgtcgg gataccacta caacgctctc 60
acctgcgaag gatgcaaggg cttctttcgg aggagtatca ccaaaaacgc agtgtaccag 120
tccaaatacg gcaccaattg tgaaatagac atgtatatgc ggcgcaagtg ccaggagtgc 180
cgactcaaga agtgcctcag tgtagggatg aggccagaat gtgtagtacc tgagtatcaa 240
tgtgccgtaa aaaggaaaga gaaaaaagct caaaaggaca aagataaacc tgtctcttca 300
accaatggct cgcctgaaat gagaatagac caggacaacc gttgtgtggt gttgcagagt 360
gaagacaaca ggtacaactc gagtacgccc agtttcggag tcaaacccct cagtccagaa 420
caagaggagc tcatccacag gctcgtctac ttccagaacg agtacgaaca ccctgccgag 480
gaggatctca agcggatcga gaacctcccc tgtgacgacg atgacccgtg tgatgttcgc 540
tacaaacaca ttacggagat cacaatactc acagtccagc tcatcgtgga gtttgcgaaa 600
aaactgcctg gtttcgacaa actactgaga gaggaccaga tcgtgttgct caaggcgtgt 660
tcgagcgagg tgatgatgct gcggatggcg cggaggtacg acgtccagac agactcgatc 720
ctgttcgcca acaaccagcc gtacacgcga gagtcgtaca cgatggcagg cgtgggggaa 780
gtcatcgaag atctgctgcg gttcggccga ctcatgtgct ccatgaaggt ggacaatgcc 840
gagtatgctc tgctcacggc catcgtcatc ttctccgagc ggccgaacct ggcggaagga 900
tggaaggttg agaagatcca ggagatctac ctggaggcgc tcaagtccta cgtggacaac 960
cgagtgaaac ctcgcagtcc gaccatcttc gccaaactgc tctccgttct caccgagctg 1020
cgaacactcg gcaaccagaa ctccgagatg tgcttctcgt taaactacgc aaccgcaaac 1080
atgccaccgt tcctcgaaga aatctggga 1109

<210> SEQ ID NO 70
<211> LENGTH: 401
<212> TYPE: PRT
<213> ORGANISM: Choristoneura fumiferana

<400> SEQUENCE: 70

Cys Leu Val Cys Gly Asp Arg Ala Ser Gly Tyr His Tyr Asn Ala Leu
1 5 10 15

Thr Cys Glu Gly Cys Lys Gly Phe Phe Arg Arg Ser Val Thr Lys Asn
20 25 30

Ala Val Tyr Ile Cys Lys Phe Gly His Ala Cys Glu Met Asp Met Tyr
35 40 45

Met Arg Arg Lys Cys Gln Glu Cys Arg Leu Lys Lys Cys Leu Ala Val
50 55 60

Gly Met Arg Pro Glu Cys Val Val Pro Glu Thr Gln Cys Ala Met Lys
65 70 75 80

Arg Lys Glu Lys Lys Ala Gln Lys Glu Lys Asp Lys Leu Pro Val Ser
85 90 95

Thr Thr Thr Val Asp Asp His Met Pro Pro Ile Met Gln Cys Glu Pro
100 105 110

Pro Pro Pro Glu Ala Ala Arg Ile His Glu Val Val Pro Arg Phe Leu
115 120 125

Ser Asp Lys Leu Leu Glu Thr Asn Arg Gln Lys Asn Ile Pro Gln Leu
130 135 140

Thr Ala Asn Gln Gln Phe Leu Ile Ala Arg Leu Ile Trp Tyr Gln Asp
145 150 155 160

Gly Tyr Glu Gln Pro Ser Asp Glu Asp Leu Lys Arg Ile Thr Gln Thr
165 170 175

Trp Gln Gln Ala Asp Asp Glu Asn Glu Glu Ser Asp Thr Pro Phe Arg
180 185 190

Gln Ile Thr Glu Met Thr Ile Leu Thr Val Gln Leu Ile Val Glu Phe
195 200 205

Ala Lys Gly Leu Pro Gly Phe Ala Lys Ile Ser Gln Pro Asp Gln Ile
210 215 220

Thr Leu Leu Lys Ala Cys Ser Ser Glu Val Met Met Leu Arg Val Ala
225 230 235 240

Arg Arg Tyr Asp Ala Ala Ser Asp Ser Val Leu Phe Ala Asn Asn Gln
245 250 255

Ala Tyr Thr Arg Asp Asn Tyr Arg Lys Ala Gly Met Ala Tyr Val Ile

-continued

```
            260                 265                 270

Glu Asp Leu Leu His Phe Cys Arg Cys Met Tyr Ser Met Ala Leu Asp
        275                 280                 285

Asn Ile His Tyr Ala Leu Leu Thr Ala Val Val Ile Phe Ser Asp Arg
    290                 295                 300

Pro Gly Leu Glu Gln Pro Gln Leu Val Glu Glu Ile Gln Arg Tyr Tyr
305                 310                 315                 320

Leu Asn Thr Leu Arg Ile Tyr Ile Leu Asn Gln Leu Ser Gly Ser Ala
                325                 330                 335

Arg Ser Ser Val Ile Tyr Gly Lys Ile Leu Ser Ile Leu Ser Glu Leu
            340                 345                 350

Arg Thr Leu Gly Met Gln Asn Ser Asn Met Cys Ile Ser Leu Lys Leu
        355                 360                 365

Lys Asn Arg Lys Leu Pro Pro Phe Leu Glu Glu Ile Trp Asp Val Ala
    370                 375                 380

Asp Met Ser His Thr Gln Pro Pro Pro Ile Leu Glu Ser Pro Thr Asn
385                 390                 395                 400

Leu


<210> SEQ ID NO 71
<211> LENGTH: 894
<212> TYPE: DNA
<213> ORGANISM: Tenebrio molitor

<400> SEQUENCE: 71

aggccggaat gtgtggtacc ggaagtacag tgtgctgtta agagaaaaga gaagaaagcc      60

caaaaggaaa aagataaacc aaacagcact actaacggct caccagacgt catcaaaatt     120

gaaccagaat tgtcagattc agaaaaaaca ttgactaacg gacgcaatag gatatcacca     180

gagcaagagg agctcatact catacatcga ttggtttatt tccaaaacga atatgaacat     240

ccgtctgaag aagacgttaa acggattatc aatcagccga tagatggtga agatcagtgt     300

gagatacggt ttaggcatac cacggaaatt acgatcctga ctgtgcagct gatcgtggag     360

tttgccaagc ggttaccagg cttcgataag ctcctgcagg aagatcaaat tgctctcttg     420

aaggcatgtt caagcgaagt gatgatgttc aggatggccc gacgttacga cgtccagtcg     480

gattccatcc tcttcgtaaa caaccagcct tatccgaggg acagttacaa tttggccggt     540

atgggggaaa ccatcgaaga tctcttgcat ttttgcagaa ctatgtactc catgaaggtg     600

gataatgccg aatatgcttt actaacagcc atcgttattt tctcagagcg accgtcgttg     660

atagaaggct ggaaggtgga gaagatccaa gaaatctatt tagaggcatt gcgggcgtac     720

gtcgacaacc gaagaagccc aagccggggc acaatattcg cgaaactcct gtcagtacta     780

actgaattgc ggacgttagg caaccaaaat tcagagatgt gcatctcgtt gaaattgaaa     840

aacaaaaagt taccgccgtt cctggacgaa atctgggacg tcgacttaaa agca           894


<210> SEQ ID NO 72
<211> LENGTH: 298
<212> TYPE: PRT
<213> ORGANISM: Tenebrio molitor

<400> SEQUENCE: 72

Arg Pro Glu Cys Val Val Pro Glu Val Gln Cys Ala Val Lys Arg Lys
1               5                   10                  15

Glu Lys Lys Ala Gln Lys Glu Lys Asp Lys Pro Asn Ser Thr Thr Asn
            20                  25                  30
```

-continued

```
Gly Ser Pro Asp Val Ile Lys Ile Glu Pro Glu Leu Ser Asp Ser Glu
        35                  40                  45

Lys Thr Leu Thr Asn Gly Arg Asn Arg Ile Ser Pro Glu Gln Glu Glu
    50                  55                  60

Leu Ile Leu Ile His Arg Leu Val Tyr Phe Gln Asn Glu Tyr Glu His
65                  70                  75                  80

Pro Ser Glu Glu Asp Val Lys Arg Ile Ile Asn Gln Pro Ile Asp Gly
                85                  90                  95

Glu Asp Gln Cys Glu Ile Arg Phe Arg His Thr Thr Glu Ile Thr Ile
            100                 105                 110

Leu Thr Val Gln Leu Ile Val Glu Phe Ala Lys Arg Leu Pro Gly Phe
        115                 120                 125

Asp Lys Leu Leu Gln Glu Asp Gln Ile Ala Leu Leu Lys Ala Cys Ser
    130                 135                 140

Ser Glu Val Met Met Phe Arg Met Ala Arg Arg Tyr Asp Val Gln Ser
145                 150                 155                 160

Asp Ser Ile Leu Phe Val Asn Asn Gln Pro Tyr Pro Arg Asp Ser Tyr
                165                 170                 175

Asn Leu Ala Gly Met Gly Glu Thr Ile Glu Asp Leu Leu His Phe Cys
            180                 185                 190

Arg Thr Met Tyr Ser Met Lys Val Asp Asn Ala Glu Tyr Ala Leu Leu
        195                 200                 205

Thr Ala Ile Val Ile Phe Ser Glu Arg Pro Ser Leu Ile Glu Gly Trp
    210                 215                 220

Lys Val Glu Lys Ile Gln Glu Ile Tyr Leu Glu Ala Leu Arg Ala Tyr
225                 230                 235                 240

Val Asp Asn Arg Arg Ser Pro Ser Arg Gly Thr Ile Phe Ala Lys Leu
                245                 250                 255

Leu Ser Val Leu Thr Glu Leu Arg Thr Leu Gly Asn Gln Asn Ser Glu
            260                 265                 270

Met Cys Ile Ser Leu Lys Leu Lys Asn Lys Lys Leu Pro Pro Phe Leu
        275                 280                 285

Asp Glu Ile Trp Asp Val Asp Leu Lys Ala
    290                 295
```

<210> SEQ ID NO 73
<211> LENGTH: 948
<212> TYPE: DNA
<213> ORGANISM: Amblyomma americanum

<400> SEQUENCE: 73

```
cggccggaat gtgtggtgcc ggagtaccag tgtgccatca agcgggagtc taagaagcac      60

cagaaggacc ggccaaacag cacaacgcgg gaaagtccct cggcgctgat ggcgccatct     120

tctgtgggtg gcgtgagccc caccagccag cccatgggtg gcggaggcag ctccctgggc     180

agcagcaatc acgaggagga taagaagcca gtggtgctca gcccaggagt caagcccctc     240

tcttcatctc aggaggacct catcaacaag ctagtctact accagcagga gtttgagtcg     300

ccttctgagg aagacatgaa gaaaaccacg cccttccccc tgggagacag tgaggaagac     360

aaccagcggc gattccagca cattactgag atcaccatcc tgacagtgca gctcattgtg     420

gagttctcca agcgggtccc tggctttgac acgctggcac gagaagacca gattactttg     480

ctgaaggcct gctccagtga agtgatgatg ctgagaggtg cccggaaata tgatgtgaag     540

acagattcta tagtgtttgc caataaccag ccgtacacga gggacaacta ccgcagtgcc     600

agtgtggggg actctgcaga tgccctgttc cgcttctgcc gcaagatgtg tcagctgaga     660
```

-continued gtagacaacg ctgaatacgc actcctgacg gccattgtaa ttttctctga acggccatca 720
ctggtggacc cgcacaaggt ggagcgcatc caggagtact acattgagac cctgcgcatg 780
tactccgaga accaccggcc cccaggcaag aactactttg cccggctgct gtccatcttg 840
acagagctgc gcaccttggg caacatgaac gccgaaatgt gcttctcgct caaggtgcag 900
aacaagaagc tgccaccgtt cctggctgag atttgggaca tccaagag 948

<210> SEQ ID NO 74
<211> LENGTH: 316
<212> TYPE: PRT
<213> ORGANISM: Amblyomma americanum

<400> SEQUENCE: 74

```
Arg Pro Glu Cys Val Val Pro Glu Tyr Gln Cys Ala Ile Lys Arg Glu
1               5                   10                  15

Ser Lys Lys His Gln Lys Asp Arg Pro Asn Ser Thr Thr Arg Glu Ser
            20                  25                  30

Pro Ser Ala Leu Met Ala Pro Ser Ser Val Gly Gly Val Ser Pro Thr
        35                  40                  45

Ser Gln Pro Met Gly Gly Gly Gly Ser Ser Leu Gly Ser Ser Asn His
    50                  55                  60

Glu Glu Asp Lys Lys Pro Val Val Leu Ser Pro Gly Val Lys Pro Leu
65                  70                  75                  80

Ser Ser Ser Gln Glu Asp Leu Ile Asn Lys Leu Val Tyr Tyr Gln Gln
                85                  90                  95

Glu Phe Glu Ser Pro Ser Glu Glu Asp Met Lys Lys Thr Thr Pro Phe
            100                 105                 110

Pro Leu Gly Asp Ser Glu Glu Asp Asn Gln Arg Arg Phe Gln His Ile
        115                 120                 125

Thr Glu Ile Thr Ile Leu Thr Val Gln Leu Ile Val Glu Phe Ser Lys
    130                 135                 140

Arg Val Pro Gly Phe Asp Thr Leu Ala Arg Glu Asp Gln Ile Thr Leu
145                 150                 155                 160

Leu Lys Ala Cys Ser Ser Glu Val Met Met Leu Arg Gly Ala Arg Lys
                165                 170                 175

Tyr Asp Val Lys Thr Asp Ser Ile Val Phe Ala Asn Asn Gln Pro Tyr
            180                 185                 190

Thr Arg Asp Asn Tyr Arg Ser Ala Ser Val Gly Asp Ser Ala Asp Ala
        195                 200                 205

Leu Phe Arg Phe Cys Arg Lys Met Cys Gln Leu Arg Val Asp Asn Ala
    210                 215                 220

Glu Tyr Ala Leu Leu Thr Ala Ile Val Ile Phe Ser Glu Arg Pro Ser
225                 230                 235                 240

Leu Val Asp Pro His Lys Val Glu Arg Ile Gln Glu Tyr Tyr Ile Glu
                245                 250                 255

Thr Leu Arg Met Tyr Ser Glu Asn His Arg Pro Pro Gly Lys Asn Tyr
            260                 265                 270

Phe Ala Arg Leu Leu Ser Ile Leu Thr Glu Leu Arg Thr Leu Gly Asn
        275                 280                 285

Met Asn Ala Glu Met Cys Phe Ser Leu Lys Val Gln Asn Lys Lys Leu
    290                 295                 300

Pro Pro Phe Leu Ala Glu Ile Trp Asp Ile Gln Glu
305                 310                 315
```

-continued

```
<210> SEQ ID NO 75
<211> LENGTH: 825
<212> TYPE: DNA
<213> ORGANISM: Drosophila melanogaster

<400> SEQUENCE: 75

gtgtccaggg atttctcgat cgagcgcatc atagaggccg agcagcgagc ggagacccaa     60

tgcggcgatc gtgcactgac gttcctgcgc gttggtccct attccacagt ccagccggac    120

tacaagggtg ccgtgtcggc cctgtgccaa gtggtcaaca aacagctctt ccagatggtc    180

gaatacgcgc gcatgatgcc gcactttgcc caggtgccgc tggacgacca ggtgattctg    240

ctgaaagccg cttggatcga gctgctcatt gcgaacgtgg cctggtgcag catcgtttcg    300

ctggatgacg gcggtgccgg cggcgggggc ggtggactag gccacgatgg ctcctttgag    360

cgacgatcac cgggccttca gccccagcag ctgttcctca accagagctt ctcgtaccat    420

cgcaacagtg cgatcaaagc cggtgtgtca gccatcttcg accgcatatt gtcggagctg    480

agtgtaaaga tgaagcggct gaatctcgac cgacgcgagc tgtcctgctt gaaggccatc    540

atactgtaca acccggacat acgcgggatc aagagccggg cggagatcga gatgtgccgc    600

gagaaggtgt acgcttgcct ggacgagcac tgccgcctgg aacatccggg cgacgatgga    660

cgctttgcgc aactgctgct gcgtctgccc gctttgcgat cgatcagcct gaagtgccag    720

gatcacctgt tcctcttccg cattaccagc gaccggccgc tggaggagct ctttctcgag    780

cagctggagg cgccgccgcc acccggcctg gcgatgaaac tggag                    825
```

NON-HUMAN ORGANISM COMPRISING A GENE EXPRESSION MODULATION SYSTEM ENCODING A CHIMERIC RETINOID X RECEPTOR

This is a Continuation of application Ser. No. 10/468,199 filed 17 Dec. 2003 now U.S. Pat. No. 7,531,326, which claims priority to PCT/US02/05706 filed on 20 Feb. 2002, and U.S. Provisional No. 60/294,814 filed on 31 May 2001, and U.S. Provisional No. 60/294,819 filed on 31 May 2001, and U.S. Provisional No. 60/269,799 filed 20 Feb. 2001, the contents of which are incorporated herein by reference in its entirety.

FIELD OF THE INVENTION

This invention relates to the field of biotechnology or genetic engineering. Specifically, this invention relates to the field of gene expression. More specifically, this invention relates to a novel ecdysone receptor/chimeric retinoid X receptor-based inducible gene expression system and methods of modulating the expression of a gene within a host cell using this inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83: 5414-5418; Artheiter et al., 1990, Cell 62: 51-61; Filmus et al., 1992, Nucleic Acids Research 20: 27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change which releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, *Science* 262:1019-24; Belshaw et al., 1996, *Proc Natl Acad Sci USA* 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998, Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530,028). Both analogs have exceptional safety profiles to other organisms.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 5,880,333 discloses a *Drosophila melanogaster* EcR and ultraspiracle (USP) heterodimner system used in plants in which the transactivation domain and the DNA binding domain are positioned on two different hybrid proteins. Unfortunately, this system is not effective for inducing reporter gene expression in animal cells (for comparison, see Example 1.2, below).

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880,333). For most applications that rely on modulating gene expression, these EcR-based systems are undesirable. Therefore, a need exists in the art for improved systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. Improved systems that are simple, compact, and dependent on ligands that are relatively inexpensive, readily available, and of low toxicity to the host would prove useful for regulating biological systems.

Recently, Applicants have shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215.

Applicants previously demonstrated that an ecdysone receptor-based gene expression system in partnership with a dipteran (*Drosophila melanogaster*) or a lepidopteran (*Choristoneura fumiferana*) ultraspiracle protein (USP) is constitutively expressed in mammalian cells, while an ecdysone receptor-based gene expression system in partnership with a vertebrate retinoid X receptor (RXR) is inducible in mammalian cells (pending application PCT/US01/09050). Applicants have recently made the surprising discovery that a non-Dipteran and non-Lepidopteran invertebrate RXR can function similar to vertebrate RXR in an ecdysone receptor-based inducible gene expression system (US application filed concurrently herewith).

Applicants have now shown that a chimeric RXR ligand binding domain, comprising at least two polypeptide fragments, wherein the first polypeptide fragment is from one species of vertebrate/invertebrate RXR and the second polypeptide fragment is from a different species of vertebrate/invertebrate RXR, whereby a vertebrate/invertebrate chimeric RXR ligand binding domain, a vertebrate/vertebrate chimeric RXR ligand binding domain, or an invertebrate/invertebrate chimeric RXR ligand binding domain is produced, can function similar to or better than either the parental vertebrate RXR or the parental invertebrate RXR in an ecdysone receptor-based inducible gene expression system. As described herein, Applicants' novel ecdysone receptor/chimeric retinoid X receptor-based inducible gene expression system provides an inducible gene expression system in bacteria, fungi, yeast, animal, and mammalian cells that is characterized by increased ligand sensitivity and magnitude of transactivation.

SUMMARY OF THE INVENTION

The present invention relates to a novel ecdysone receptor/chimeric retinoid X receptor-based inducible gene expression system, novel chimeric receptor polynucleotides and polypeptides for use in the novel inducible gene expression system, and methods of modulating the expression of a gene within a host cell using this inducible gene expression system. In particular, Applicants' invention relates to a novel gene expression modulation system comprising a polynucleotide encoding a chimeric RXR ligand binding domain (LBD).

Specifically, the present invention relates to a gene expression modulation system comprising: a) a first gene expression cassette that is capable of being expressed in a host cell comprising a polynucleotide that encodes a first hybrid polypeptide comprising: i) a DNA-binding domain that recognizes a response element associated with a gene whose expression is to be modulated; and ii) an ecdysone receptor ligand binding domain; and b) a second gene expression cassette that is capable of being expressed in the host cell comprising a polynucleotide sequence that encodes a second hybrid polypeptide comprising: i) a transactivation domain; and ii) a chimeric retinoid X receptor ligand binding domain.

The present invention also relates to a gene expression modulation system comprising: a) a first gene expression cassette that is capable of being expressed in a host cell comprising a polynucleotide that encodes a first hybrid polypeptide comprising: i) a DNA-binding domain that recognizes a response element associated with a gene whose expression is to be modulated; and ii) a chimeric retinoid X receptor ligand binding domain; and b) a second gene expression cassette that is capable of being expressed in the host cell comprising a polynucleotide sequence that encodes a second hybrid polypeptide comprising: i) a transactivation domain; and ii) an ecdysone receptor ligand binding domain.

The present invention also relates to a gene expression modulation system according to the invention further comprising c) a third gene expression cassette comprising: i) a response element to which the DNA-binding domain of the first hybrid polypeptide binds; ii) a promoter that is activated by the transactivation domain of the second hybrid polypeptide; and iii) a gene whose expression is to be modulated.

The present invention also relates to a gene expression cassette that is capable of being expressed in a host cell, wherein the gene expression cassette comprises a polynucleotide that encodes a hybrid polypeptide comprising either i) a DNA-binding domain that recognizes a response element associated with a gene whose expression is to be modulated, or ii) a transactivation domain; and a chimeric retinoid X receptor ligand binding domain.

The present invention also relates to an isolated polynucleotide that encodes a hybrid polypeptide comprising either i) a DNA-binding domain that recognizes a response element associated with a gene whose expression is to be modulated, or ii) a transactivation domain; and a chimeric vertebrate and invertebrate retinoid X receptor ligand binding domain. The present invention also relates to a isolated hybrid polypeptide encoded by the isolated polynucleotide according to the invention.

The present invention also relates to an isolated polynucleotide encoding a truncated chimeric RXR LBD. In a specific embodiment, the isolated polynucleotide encodes a truncated chimeric RXR LBD, wherein the truncation mutation affects ligand binding activity or ligand sensitivity of the chimeric RXR LBD. In another specific embodiment, the isolated polynucleotide encodes a truncated chimeric RXR polypeptide comprising a truncation mutation that increases ligand sensitivity of a heterodimer comprising the truncated chimeric RXR polypeptide and a dimerization partner. In a specific embodiment, the dimerization partner is an ecdysone receptor polypeptide.

The present invention also relates to an isolated polypeptide encoded by a polynucleotide according to Applicants' invention.

The present invention also relates to an isolated hybrid polypeptide comprising either i) a DNA-binding domain that recognizes a response element associated with a gene whose expression is to be modulated, or ii) a transactivation domain; and a chimeric retinoid X receptor ligand binding domain.

The present invention relates to an isolated truncated chimeric RXR LBD comprising a truncation mutation, wherein the truncated chimeric RXR LBD is encoded by a polynucleotide according to the invention.

Thus, the present invention also relates to an isolated truncated chimeric RXR LBD comprising a truncation mutation that affects ligand binding activity or ligand sensitivity of said truncated chimeric RXR LBD.

The present invention also relates to an isolated truncated chimeric RXR LBD comprising a truncation mutation that increases ligand sensitivity of a heterodimer comprising the truncated chimeric RXR LBD and a dimerization partner. In a specific embodiment, the dimerization partner is an ecdysone receptor polypeptide.

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; b) introducing into the host cell a gene expression cassette comprising i) a response element comprising a domain recognized by the DNA binding domain from the first hybrid polypeptide; ii) a promoter that is activated by the transactivation domain of the second hybrid polypeptide; and iii) a gene whose expression is to be modulated; and c) introducing into the host cell a ligand; whereby upon introduction of the ligand into the host, expression of the gene of b)iii) is modulated.

Applicants' invention also provides a method of modulating the expression of a gene in a host cell comprising a gene expression cassette comprising a response element comprising a domain recognized by the DNA binding domain from the first hybrid polypeptide; a promoter that is activated by the transactivation domain of the second hybrid polypeptide; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Applicants' invention also provides an isolated host cell comprising an inducible gene expression system according to the invention. The present invention also relates to an isolated host cell comprising a gene expression cassette, a polynucleotide, or a polypeptide according to the invention. Accordingly, Applicants' invention also relates to a non-human organism comprising a host cell according to the invention.

BRIEF DESCRIPTION OF THE DRAWINGS

FIG. 4: Amino acid sequence alignments of the EF domains of six vertebrate RXRs (A) and six invertebrate RXRs (B). B6, B8, B9, B10 and B11 denotes βchimera junctions. A1 denotes junction for αchimera. Helices 1-12 are denoted as H1-H12 and β pleated sheets are denoted as S1 and S2. F denotes the F domain junction.

DETAILED DESCRIPTION OF THE INVENTION

Figure 1:
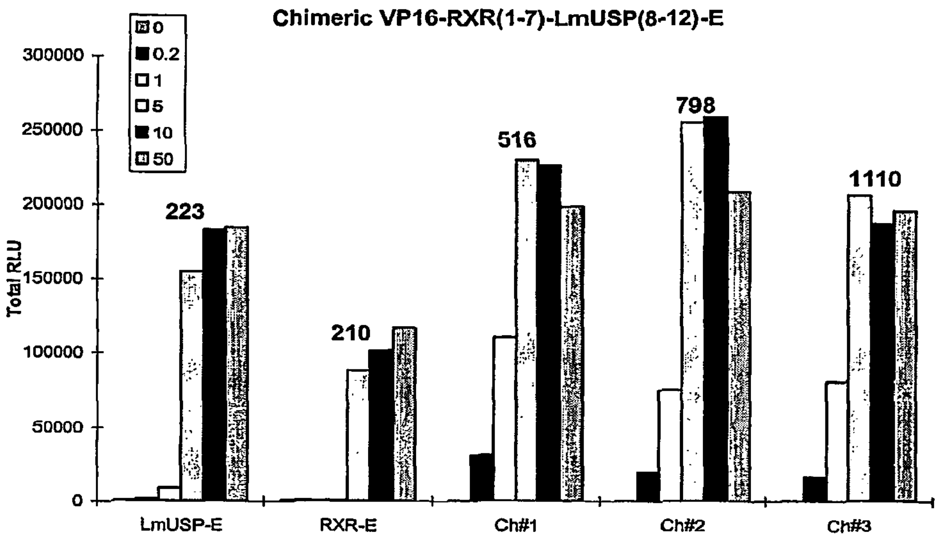
FIG. 1: Expression data of VP16LmUSP-EF, VP16MmRXRα-EF and three independent clones of VP16MmRXRα(1-7)-LmUSP (8-12)-EF in NIH3T3 cells along with GAL4CfEcR-CDEF and pFRLuc in the presence of non-steroid (GSE) ligand.

Applicants have now shown that chimeric RXR ligand binding domains are functional within an EcR-based inducible gene expression modulation system in mammalian cells and that these chimeric RXR LBDs exhibit advantageous ligand sensitivities and transactivation abilities. Thus, Applicants' invention provides a novel ecdysone receptor-based inducible gene expression system comprising a chimeric retinoid X receptor ligand binding domain that is useful for modulating expression of a gene of interest in a host cell. In a particularly desirable embodiment, Applicants' invention provides an inducible gene expression system that has a reduced level of background gene expression and responds to submicromolar concentrations of non-steroidal ligand. Thus, Applicants' novel inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, functional genomics, proteomics, and metabolomics analyses and regulation of traits in transgenic organisms, where control of gene expression levels is desirable. An advantage of Applicants' invention is that it provides a means to regulate gene expression and to tailor expression levels to suit the user's requirements.

DEFINITIONS

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g. 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible.

The term "complementary" is used to describe the relationship between nucleotide bases that are capable of hybridizing to one another. For example, with respect to DNA, adenosine is complementary to thymidine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule. As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning fall length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3←5'5'→3').

The term "tall-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as PBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzmatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g. Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et al., 1987, Proc. Natl. Acad. Sci. U.S.A. 84: 7413; Mackey, et al., 1988, Proc. Natl. Acad. Sci. U.S.A 85: 8027-8031; and Ulmer et al., 1993, Science 259: 1745-1748). The use of cationic lipids may promote encapsulation of negatively charged nucleic acids, and also promote fusion with negatively charged cell membranes (Felgner and Ringold, 1989, Science 337: 387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Cherbas L., et. al., (1991), *Genes Dev.* 5, 120-131); AGGTCAN$_{(n)}$AGGTCA, where N$_{(n)}$ can be one or more spacer nucleotides (see D'Avino P P., et. al., (1995), *Mol. Cell. Endocrinzol,* 113, 1-9); and GGGTTGAATGAATTT (see Antoniewski C., et. al., (1994), Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-promoters; animal and mammalian promoters known in the art include, but are not limited to, the SV40 early (SV40e) promoter region, the promoter contained in the 3' long terminal repeat (LTR) of *Rous sarcoma* virus (RSV), the promoters of the E1A or major late promoter (MLP) genes of adenoviruses (Ad), the cytomegalovirus (CMV) early promoter, the herpes simplex virus (HSV) thymidine kinase (TK) promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

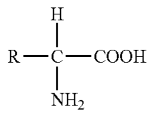

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

Gene Expression Modulation System of the Invention

Applicants have previously shown that separating the transactivation and DNA binding domains by placing them on two different proteins results in greatly reduced background activity in the absence of a ligand and significantly increased activity over background in the presence of a ligand (pending application PCT/US01/09050). This two-hybrid system is a significantly improved inducible gene expression modulation system compared to the two systems disclosed in International Patent Applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

The two-hybrid ecdysone receptor-based gene expression modulation system may be either heterodimeric and homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9: 222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins which are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear, receptor superfamily are also characterized by the presence of four or five domains: A/B, C, D, E, and in some members F (see U.S. Pat. No. 4,981,784 and Evans, *Science* 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. This EcR receptor, like a subset of the steroid receptor family, also possesses less well-defined regions responsible for heterodimerization properties. Because the domains of EcR, USP, and RXR are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. Applicants have previously shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050). This two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a specific embodiment of the two-hybrid system, native DNA binding and transactivation domains of EcR or RXR are eliminated and as a result, these chimeric molecules have less chance of interacting with other steroid hormone receptors present in the cell resulting in reduced side effects.

Applicants have previously shown that an ecdysone receptor in partnership with a dipteran (fruit fly *Drosophila melanzogaster*) or a lepidopteran (spruce bud worm *Choristoneura fumiferana*) ultraspiracle protein (USP) is constitutively expressed in mammalian cells, while an ecdysone receptor in partnership with a vertebrate retinoid X receptor (RXR) is inducible in mammalian cells (pending application PCT/US01/09050). Recently, Applicants made the surprising discovery that the ultraspiracle protein of *Locusta migratoria* ("LmUSP") and the RXR homolog 1 and RXR homolog 2 of the ixodid tick *Amblyomma americanum* ("AmaRXR1" and "AmaRXR2", respectively) and their non-Dipteran, non-Lepidopteran homologs including, but not limited to: fiddler crab *Celuca pugilator* RXR homolog ("CpRXR"), beetle *Tenebrio molitor* RXR homolog ("$T_m$ RXR"), honeybee *Apis mellifera* RXR homolog ("AmRXR"), and an aphid *Myzus persicae* RXR homolog ("MpRXR"), all of which are referred to herein collectively as invertebrate RXRs, can function similar to vertebrate retinoid X receptor (RXR) in an inducible ecdysone receptor-based inducible gene expression system in mammalian cells (US application filed herewith, incorporated by reference herein, in its entirety).

As described herein, Applicants have now discovered that a chimeric RXR ligand binding domain comprising at least two polypeptide fragments, wherein the first polypeptide fragment is from one species of vertebrate/invertebrate RXR and the second polypeptide fragment is from a different species of vertebrate/invertebrate RXR, whereby a vertebrate/invertebrate chimeric RXR ligand binding domain, a vertebrate/vertebrate chimeric RXR ligand binding domain, or an invertebrate/invertebrate chimeric RXR ligand binding domain is produced, can function in an ecdysone receptor-based inducible gene expression system. Surprisingly, Applicants' novel EcR/chimeric RXR-based inducible gene expression system can function similar to or better than both the EcR/vertebrate RXR-based gene expression system (PCT/US01/09050) and the EcR/invertebrate RXR-based gene expression system (US application filed herewith) in terms of ligand sensitivity and magnitude of gene induction. Thus, the present invention provides an improved EcR-based inducible gene expression system for use in bacterial, fungal, yeast, animal, and mammalian cells.

In particular, Applicants describe herein a novel two-hybrid system that comprises a chimeric RXR ligand binding domain. This novel gene expression system demonstrates for the first time that a polypeptide comprising a chimeric RXR ligand binding domain can function as a component of an inducible EcR-based inducible gene expression system in yeast and mammalian cells. As discussed herein, this finding is both unexpected and surprising.

Specifically, Applicants' invention relates to a gene expression modulation system comprising: a) a first gene expression cassette that is capable of being expressed in a host cell, wherein the first gene expression cassette comprises a polynucleotide that encodes a first hybrid polypeptide comprising i) a DNA-binding domain that recognizes a response element associated with a gene whose expression is to be modulated; and ii) an ecdysone receptor ligand binding domain; and b) a second gene expression cassette that is capable of being expressed in the host cell, wherein the second gene expression cassette comprises a polynucleotide sequence that encodes a second hybrid polypeptide comprising i) a transactivation domain; and ii) a chimeric retinoid X receptor ligand binding domain.

The present invention also relates to a gene expression modulation system comprising: a) a first gene expression cassette that is capable of being expressed in a host cell, wherein the first gene expression cassette comprises a polynucleotide that encodes a first hybrid polypeptide comprising i) a DNA-binding domain that recognizes a response element associated with a gene whose expression is to be modulated; and ii) a chimeric retinoid X receptor ligand binding domain; and b) a second gene expression cassette that is capable of being expressed in the host cell, wherein the second gene expression cassette comprises a polynucleotide sequence that encodes a second hybrid polypeptide comprising i) a transactivation domain; and ii) an ecdysone receptor ligand binding domain.

The present invention also relates to a gene expression modulation system according to the present invention further comprising c) a third gene expression cassette comprising: i) a response element to which the DNA-binding domain of the first hybrid polypeptide binds; ii) a promoter that is activated by the transactivation domain of the second hybrid polypeptide; and iii) a gene whose expression is to be modulated.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with an EcR ligand binding domain and a chimeric RXR ligand binding domain, which in turn are bound to the response element linked to a gene, provide the means for external temporal regulation of expression of the gene. The binding mechanism or the order in which the various components of this invention bind to each other, that is, for example, ligand to receptor, first hybrid polypeptide to response element, second hybrid polypeptide to promoter, etc., is not critical. Binding of the ligand to the EcR ligand binding domain and the chimeric RXR ligand binding domain enables expression or suppression of the gene. This mechanism does not exclude the potential for ligand binding to EcR or chimeric RXR, and the resulting formation of active homodimer complexes (e.g. EcR+EcR or chimeric RXR+chimeric RXR). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988), Nature 335: 563-564) or LexA protein from *Escherichia coli* (see Brent and Ptashne (1985), Cell 43: 729-736), or synthetic response elements specific for targeted interactions with proteins designed, modified, and selected for such specific interactions (see, for example, Kim, et al. (1997), *Proc. Natl. Acad. Sci. USA* 94: 3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

Gene Expression Cassettes of the Invention

The novel EcR/chimeric RXR-based inducible gene expression system of the invention comprises gene expression cassettes that are capable of being expressed in a host cell, wherein the gene expression cassettes each comprise a polynucleotide encoding a hybrid polypeptide. Thus, Applicants' invention also provides gene expression cassettes for use in the gene expression system of the invention.

Specifically, the present invention provides a gene expression cassette comprising a polynucleotide encoding a hybrid polypeptide. In particular, the present invention provides a gene expression cassette that is capable of being expressed in a host cell, wherein the gene expression cassette comprises a polynucleotide that encodes a hybrid polypeptide comprising either i) a DNA-binding domain that recognizes a response element, or ii) a transactivation domain; and an ecdysone receptor ligand binding domain or a chimeric retinoid X receptor ligand binding domain.

In a specific embodiment, the gene expression cassette encodes a hybrid polypeptide comprising a DNA-binding domain that recognizes a response element and an EcR ligand binding domain.

In another specific embodiment, the gene expression cassette encodes a hybrid polypeptide comprising a DNA-binding domain that recognizes a response element and a chimeric RXR ligand binding domain.

In another specific embodiment, the gene expression cassette encodes a hybrid polypeptide comprising a transactivation domain and an EcR ligand binding domain.

In another specific embodiment, the gene expression cassette encodes a hybrid polypeptide comprising a transactivation domain and a chimeric RXR ligand binding domain.

In a preferred embodiment, the ligand binding domain (LBD) is an EcR LBD, a chimeric RXR LBD, or a related steroid/thyroid hormone nuclear receptor family member LBD or chimeric LBD, analog, combination, or modification thereof. In a specific embodiment, the LBD is an EcR LBD or a chimeric RXR LBD. In another specific embodiment, the LBD is from a truncated EcR LBD or a truncated chimeric RXR LBD. A truncation mutation may be made by any method used in the art, including but not limited to restriction endonuclease digestion/deletion, PCR-mediated/oligonucleotide-directed deletion, chemical mutagenesis, DNA strand breakage, and the like.

The EcR may be an invertebrate EcR, preferably selected from the class Arthropod. Preferably, the EcR is selected from the group consisting of a Lepidopteran EcR, a Dipteran EcR, an Orthopteran EcR, a Homopteran EcR and a Hemipteran EcR. More preferably, the EcR for use is a spruce budworm *Choristoneura Fumiferana* EcR ("CfEcR"), a beetle *Tenebrio molitor* EcR ("$T_m$ EcR"), a *Manduca sexta* EcR ("MsEcR"), a *Heliothies virescens* EcR ("HvEcR"), a midge *Chironomus tentans* EcR ("CtEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* EcR ("LcEcR"), a blowfly *Lucilia cuprina* EcR ("LucEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Celuca pugilator* EcR ("CpEcR"), an ixodid tick *Amblyomma americanum* EcR ("AmaEcR"), a whitefly *Bamecia argentifoli* EcR ("BaEcR", SEQ ID NO: 68) or a leafhopper *Nephotetix cincticeps* EcR ("NcEcR", SEQ ID NO: 69). In a specific embodiment, the LBD is from spruce budworm (*Choristoneura fumiferana*) EcR ("CfEcR") or fruit fly *Drosophila melanogaster* EcR ("DmEcR").

In a specific embodiment, the EcR LBD comprises full-length EF domains. In a preferred embodiment, the full length EF domains are encoded by a polynucleotide comprising a nucleic acid sequence of SEQ ID NO: 1 or SEQ ID NO: 2.

In a specific embodiment, the LBD is from a truncated EcR LBD. The EcR LBD truncation results in a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, or 240 amino acids. In another specific embodiment, the EcR LBD truncation result in a deletion of at least a partial polypeptide domain. In another specific embodiment, the EcR LBD truncation results in a deletion of at least an entire polypeptide domain. More preferably, the EcR polypeptide truncation results in a deletion of at least an A/B-domain, a C-domain, a D-domain, an F-domain, an A/B/C-domains, an A/B/1/2-C-domains, an A/B/C/D-domains, an A/B/C/D/F-domains, an A/B/F-domains, an A/B/C/F-domains, a partial E-domain, or a partial F-domain. A combination of several partial and/or complete domain deletions may also be performed.

In one embodiment, the ecdysone receptor ligand binding domain is encoded by a polynucleotide comprising a nucleic acid sequence selected from the group consisting of SEQ ID NO: 1 (CfEcR-EF), SEQ ID NO: 2 (DmEcR-EF), SEQ ID NO: 3 (CfEcR-DE), and SEQ ID NO: 4 (DmEcR-DE).

In a preferred embodiment, the ecdysone receptor ligand binding domain is encoded by a polynucleotide comprising a nucleic acid sequence selected from the group consisting of SEQ ID NO: 65 (CfEcR-DEF), SEQ ID NO: 59 (CfEcR-CDEF), SEQ ID NO: 67 (DmEcR-DEF), SEQ ID NO: 71 (TmEcR-DEF) and SEQ ID NO: 73 (AmaEcR-DEF).

In one embodiment, the ecdysone receptor ligand binding domain comprises an amino acid sequence selected from the group consisting of SEQ ID NO: 5 (CfEcR-EF), SEQ ID NO: 6 (DmEcR-EF), SEQ ID NO: 7 (CfEcR-DE), and SEQ ID NO: 8 (DmEcR-DE).

In a preferred embodiment, the ecdysone receptor ligand binding domain comprises an amino acid sequence selected from the group consisting of SEQ ID NO: 57 (CfEcR-DEF), SEQ ID NO: 70 (CfEcR-CDEF), SEQ ID NO: 58 (DmEcR-DEF), SEQ ID NO: 72 (TmEcR-DEF), and SEQ ID NO: 74 (AmaEcR-DEF).

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain according to the invention may comprise at least two different species RXR polypeptide fragments, or when the species is the same, the two or more polypeptide fragments may be from two or more different isoforms of the species RXR polypeptide fragment.

In a specific embodiment, the vertebrate species RXR polypeptide fragment is from a mouse *Mus musculus* RXR ("MmRXR") or a human *Homo sapiens* RXR ("HsRXR"). The RXR polypeptide may be an $RXR_{\alpha}$, $RXR_{\beta}$, or $RXR_{\gamma}$ isoform.

In a preferred embodiment, the vertebrate species RXR polypeptide fragment is from a vertebrate species RXR-EF domain encoded by a polynucleotide comprising a nucleic acid sequence selected from the group consisting of SEQ ID NO: 9, SEQ ID NO: 10, SEQ ID NO: 11, SEQ ID NO: 12, SEQ ID NO: 13, and SEQ ID NO: 14. In another preferred embodiment, the vertebrate species RXR polypeptide fragment is from a vertebrate species RXR-EF domain comprising an amino acid sequence selected from the group consisting of SEQ ID NO: 15, SEQ ID NO: 16, SEQ ID NO: 17, SEQ ID NO: 18, SEQ ID NO: 19, and SEQ ID NO: 20.

In another specific embodiment, the invertebrate species RXR polypeptide fragment is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), and an aphid *Myzus persicae* RXR homolog ("MpRXR").

In a preferred embodiment, the invertebrate species RXR polypeptide fragment is from a invertebrate species RXR-EF domain encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, and SEQ ID NO: 26. In another preferred embodiment, the invertebrate species RXR polypeptide fragment is from a invertebrate species RXR-EF domain comprising an amino acid sequence selected from the group consisting of SEQ ID NO: 27, SEQ ID NO: 28, SEQ ID NO: 29, SEQ ID NO: 30, SEQ ID NO: 31, and SEQ ID NO: 3.

In another specific embodiment, the invertebrate species RXR polypeptide fragment is from a non-Dipteran/non-Lepidopteran invertebrate species RXR homolog.

In a preferred embodiment, the chimeric RXR ligand binding domain comprises at least one vertebrate species RXR polypeptide fragment and one invertebrate species RXR polypeptide fragment.

In another preferred embodiment, the chimeric RXR ligand binding domain comprises at least one vertebrate species RXR polypeptide fragment and one non-Dipteran/non-Lepidopteran invertebrate species RXR homolog polypeptide fragment.

In another preferred embodiment, the chimeric RXR ligand binding domain comprises at least one invertebrate species RXR polypeptide fragment and one non-Dipteran/non-Lepidopteran invertebrate species RXR homolog polypeptide fragment.

In another preferred embodiment, the chimeric RXR ligand binding domain comprises at least one vertebrate species RXR polypeptide fragment and one different vertebrate species RXR polypeptide fragment.

In another preferred embodiment, the chimeric RXR ligand binding domain comprises at least one invertebrate species RXR polypeptide fragment and one different invertebrate species RXR polypeptide fragment.

In another preferred embodiment, the chimeric RXR ligand binding domain comprises at least one non-Dipteran/non-Lepidopteran invertebrate species RXR polypeptide fragment and one different non-Dipteran/non-Lepidopteran invertebrate species RXR polypeptide fragment.

In a specific embodiment, the chimeric RXR LBD comprises an RXR LBD domain comprising at least one polypeptide fragment selected from the group consisting of an EF-domain helix 1, an EF-domain helix 2, an EF-domain helix 3, an EF-domain helix 4, an EF-domain helix 5, an EF-domain helix 6, an EF-domain helix 7, an EF-domain helix 8, and EF-domain helix 9, an EF-domain helix 10, an EF-domain helix 11, an EF-domain helix 12, an F-domain, and an EF-domain β-pleated sheet, wherein the polypeptide fragment is from a different species RXR, i.e., chimeric to the RXR LBD domain, than the RXR LBD domain.

In another specific embodiment, the first polypeptide fragment of the chimeric RXR ligand binding domain comprises helices 1-6, helices 1-7, helices 1-8, helices 1-9, helices 1-10, helices 1-11, or helices 1-12 of a first species RXR according to the invention, and the second polypeptide fragment of the chimeric RXR ligand binding domain comprises helices 7-12, helices 8-12, helices 9-12, helices 10-12, helices 11-12, helix 12, or F domain of a second species RXR according to the invention, respectively.

In a preferred embodiment, the first polypeptide fragment of the chimeric RXR ligand binding domain comprises helices 1-6 of a first species RXR according to the invention, and the second polypeptide fragment of the chimeric RXR ligand binding domain comprises helices 7-12 of a second species RXR according to the invention.

In another preferred embodiment, the first polypeptide fragment of the chimeric RXR ligand binding domain comprises helices 1-7 of a first species RXR according to the invention, and the second polypeptide fragment of the chimeric RXR ligand binding domain comprises helices 8-12 of a second species RXR according to the invention.

In another preferred embodiment, the first polypeptide fragment of the chimeric RXR ligand binding domain comprises helices 1-8 of a first species RXR according to the invention, and the second polypeptide fragment of the chimeric RXR ligand binding domain comprises helices 9-12 of a second species RXR according to the invention.

In another preferred embodiment, the first polypeptide fragment of the chimeric RXR ligand binding domain comprises helices 1-9 of a first species RXR according to the invention, and the second polypeptide fragment of the chimeric RXR ligand binding domain comprises helices 10-12 of a second species RXR according to the invention.

In another preferred embodiment, the first polypeptide fragment of the chimeric RXR ligand binding domain comprises helices 1-10 of a first species RXR according to the invention, and the second polypeptide fragment of the chimeric RXR ligand binding domain comprises helices 11-12 of a second species RXR according to the invention.

In another preferred embodiment, the first polypeptide fragment of the chimeric RXR ligand binding domain comprises helices 1-11 of a first species RXR according to the invention, and the second polypeptide fragment of the chimeric RXR ligand binding domain comprises helix 12 of a second species RXR according to the invention.

In another preferred embodiment, the first polypeptide fragment of the chimeric RXR ligand binding domain comprises helices 1-12 of a first species RXR according to the invention, and the second polypeptide fragment of the chimeric RXR ligand binding domain comprises an F domain of a second species RXR according to the invention.

In another specific embodiment, the LBD is from a truncated chimeric RXR ligand binding domain. The chimeric RXR LBD truncation results in a deletion of at least 1, 2, 3, 4, 5, 6, 8, 10, 13, 14, 15, 16, 17, 18, 19, 20, 21, 22, 25, 26, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, or 240 amino acids. Preferably, the chimeric RXR LBD truncation results in a deletion of at least a partial polypeptide domain. More preferably, the chimeric RXR LBD truncation results in a deletion of at least an entire polypeptide domain. In a preferred embodiment, the chimeric RXR LBD truncation results in a deletion of at least a partial E-domain, a complete E-domain, a partial F-domain, a complete F-domain, an EF-domain helix 1, an EF-domain helix 2, an EF-domain helix 3, an EF-domain helix 4, an EF-domain helix 5, an EF-domain helix 6, an EF-domain helix 7, an EF-domain helix 8, and EF-domain helix 9, an EF-domain helix 10, an EF-domain helix 11, an EF-domain helix 12, or an EF-domain β-pleated sheet. A combination of several partial and/or complete domain deletions may also be performed.

In a preferred embodiment, the truncated chimeric RXR ligand binding domain is encoded by a polynucleotide comprising a nucleic acid sequence of SEQ ID NO: 33, SEQ ID NO: 34, SEQ ID NO: 35, SEQ ID NO: 36, SEQ ID NO: 37, or SEQ ID NO: 38. In another preferred embodiment, the truncated chimeric RXR ligand binding domain comprises a nucleic acid sequence of SEQ ID NO: 39, SEQ ID NO: 40, SEQ ID NO: 41, SEQ ID NO: 42, SEQ ID NO: 43, or SEQ ID NO: 44.

In a preferred embodiment, the chimeric RXR ligand binding domain is encoded by a polynucleotide comprising a nucleic acid sequence selected from the group consisting of a) SEQ ID NO: 45, b) nucleotides 1-348 of SEQ ID NO: 13 and nucleotides 268-630 of SEQ ID NO: 21, c) nucleotides 1-408 of SEQ ID NO: 13 and nucleotides 337-630 of SEQ ID NO: 21, d) nucleotides 1-465 of SEQ ID NO: 13 and nucleotides 403-630 of SEQ ID NO: 21, e) nucleotides 1-555 of SEQ ID NO: 13 and nucleotides 490-630 of SEQ ID NO: 21, f) nucleotides 1-624 of SEQ ID NO: 13 and nucleotides 547-630 of SEQ ID NO: 21, g) nucleotides 1-645 of SEQ ID NO: 13 and nucleotides 601-630 of SEQ ID NO: 21, and h) nucleotides 1-717 of SEQ ID NO: 13 and nucleotides 613-630 of SEQ ID NO: 21.

In another preferred embodiment, the chimeric RXR ligand binding domain comprises an amino acid sequence selected from the group consisting of a) SEQ ID NO: 46, b) amino acids 1-116 of SEQ ID NO: 19 and amino acids 90-210 of SEQ ID NO: 27, c) amino acids 1-136 of SEQ ID NO: 19 and amino acids 113-210 of SEQ ID NO: 27, d) amino acids 1-155 of SEQ ID NO: 19 and amino acids 135-210 of SEQ ID NO: 27 e) amino acids 1-185 of SEQ ID NO: 19 and amino acids 164-210 of SEQ ID NO: 27, f) amino acids 1-208 of SEQ ID NO: 19 and amino acids 183-210 of SEQ ID NO: 27, g) amino acids 1-215 of SEQ ID NO: 19 and amino acids 201-210 of SEQ ID NO: 27, and h) amino acids 1-239 of SEQ ID NO: 19 and amino acids 205-210 of SEQ ID NO: 27.

For purposes of this invention, EcR, vertebrate RXR, invertebrate RXR, and chimeric RXR also include synthetic and hybrid EcR, vertebrate RXR, invertebrate RXR, and chimeric RXR, and their homologs.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a steroid/thyroid hormone nuclear receptor superfamily member DBD, a bacterial LacZ DBD, or a yeast put DBD. More preferably, the DBD is a GALA DBD [SEQ ID NO: 47 (polynucleotide) or SEQ ID NO: 48 (polypeptide)] or a LexA DBD [(SEQ ID NO: 49 (polynucleotide) or SEQ ID NO: 50 (polypeptide)].

The transactivation domain (abbreviated "AD" or "TA") may be any steroid/thyroid hormone nuclear receptor AD, synthetic or chimeric AD, polyglutamine AD, basic or acidic amino acid AD, a VP16 AD, a GAL4 AD, an NF-κB AD, a BP64 AD, a B42 acidic activation domain (B42AD), or an analog, combination, or modification thereof. In a specific embodiment, the AD is a synthetic or chimeric AD, or is obtained from a VP16, GAL4, NF-κB, or B42 acidic activation domain AD. Preferably, the AD is a VP16 AD [SEQ ID NO: 51 (polynucleotide) or SEQ ID NO: 52 (polypeptide)] or a B42 AD [SEQ ID NO: 53 (polynucleotide) or SEQ ID NO: 54 (polypeptide)].

In a preferred embodiment, the gene expression cassette encodes a hybrid polypeptide comprising a DNA-binding domain encoded by a polynucleotide comprising a nucleic acid sequence selected from the group consisting of a GAL4 DBD (SEQ ID NO: 47) and a LexA DBD (SEQ ID NO: 49), and an EcR ligand binding domain encoded by a polynucleotide comprising a nucleic acid sequence selected from the group consisting of SEQ ID NO: 65 (CfEcR-DEF), SEQ ID NO: 59 (CfEcR-CDEF), SEQ ID NO: 67 (DmEcR-DEF), SEQ ID NO: 71 (TmEcR-DEF) and SEQ ID NO: 73 (AmaEcR-DEF).

In another preferred embodiment, the gene expression cassette encodes a hybrid polypeptide comprising a DNA-binding domain comprising an amino acid sequence selected from the group consisting of a GALA DBD (SEQ ID NO: 48) and a LexA DBD (SEQ ID NO: 50), and an EcR ligand binding domain comprising an amino acid sequence selected from the group consisting of SEQ ID NO: 57 (CfEcR-DEF), SEQ ID NO: 70 (CfEcR-CDEF), SEQ ID NO: 58 (DmEcR-DEF), SEQ ID NO: 72 (TmEcR-DEF), and SEQ ID NO: 74 (AmaEcR-DEF).

In another preferred embodiment, the gene expression cassette encodes a hybrid polypeptide comprising a DNA-binding domain encoded by a polynucleotide comprising a nucleic acid sequence selected from the group consisting of a GAL4 DBD (SEQ ID NO: 47) and a LexA DBD (SEQ ID NO: 49), and a chimeric RXR ligand binding domain encoded by a polynucleotide comprising a nucleic acid sequence selected from the group consisting of a) SEQ ID NO: 45, b) nucleotides 1-348 of SEQ ID NO: 13 and nucleotides 268-630 of SEQ ID NO: 21, c) nucleotides 1-408 of SEQ ID NO: 13 and nucleotides 337-630 of SEQ ID NO: 21, d) nucleotides 1-465 of SEQ ID NO: 13 and nucleotides 403-630 of SEQ ID NO: 21, e) nucleotides 1-555 of SEQ ID NO: 13 and nucleotides 490-630 of SEQ ID NO: 21, f) nucleotides 1-624 of SEQ ID NO: 13 and nucleotides 547-630 of SEQ ID NO: 21, g) nucleotides 1-645 of SEQ ID NO: 13 and nucleotides 601-630 of SEQ ID NO: 21, and h) nucleotides 1-717 of SEQ ID NO: 13 and nucleotides 613-630 of SEQ ID NO: 21.

In another preferred embodiment, the gene expression cassette encodes a hybrid polypeptide comprising a DNA-binding domain comprising an amino acid sequence selected from the group consisting of a GAL4 DBD (SEQ ID NO: 48) and a LexA DBD (SEQ ID NO: 50), and a chimeric RXR ligand binding domain comprising an amino acid sequence selected from the group consisting of a) SEQ ID NO: 46, b) amino acids 1-116 of SEQ ID NO: 19 and amino acids 90-210 of SEQ ID NO: 27, c) amino acids 1-136 of SEQ ID NO: 19 and amino acids 113-210 of SEQ ID NO: 27, d) amino acids 1-155 of SEQ ID NO: 19 and amino acids 135-210 of SEQ ID NO: 27, e) amino acids 1-185 of SEQ ID. NO: 19 and amino acids 164-210 of SEQ ID NO: 27 f) amino acids 1-208 of SEQ ID NO: 19 and amino acids 183-210 of SEQ ID NO: 27, g) amino acids 1-215 of SEQ ID NO: 19 and amino acids 201-210 of SEQ ID NO: 27. and h) amino acids 1-239 of SEQ ID NO: 19 and amino acids 205-210 of SEQ ID NO: 27.

In another preferred embodiment, the gene expression cassette encodes a hybrid polypeptide comprising a transactivation domain encoded by a polynucleotide comprising a nucleic acid sequence of SEQ ID NO: 51 or SEQ ID NO: 53, and an EcR ligand binding domain encoded by a polynucleotide comprising a nucleic acid sequence selected from the group consisting of SEQ ID NO: 65 (CfEcR-DEF), SEQ ID NO: 59 (CfEcR-CDEF), SEQ ID NO: 67 (DmEcR-DEF), SEQ ID NO: 71 (TmEcR-DEF) and SEQ ID NO: 73 (AmaEcR-DEF).

In another preferred embodiment, the gene expression cassette encodes a hybrid polypeptide comprising a transactivation domain comprising an amino acid sequence of SEQ ID NO: 52 or SEQ ID NO: 54, and an EcR ligand binding domain comprising an amino acid sequence selected from the group consisting of SEQ ID NO: 57 (CfEcR-DEF), SEQ ID NO: 70 (CfEcR-CDEF), SEQ ID NO: 58 (DmEcR-DEF), SEQ ID NO: 72 (TmEcR-DEF), and SEQ ID NO: 74 (AmaEcR-DEF).

In another preferred embodiment, the gene expression cassette encodes a hybrid polypeptide comprising a transactivation domain encoded by a polynucleotide comprising a nucleic acid sequence of SEQ ID NO: 51 or SEQ ID NO: 53 and a chimeric RXR ligand binding domain encoded by a polynucleotide comprising a nucleic acid sequence selected from the group consisting of a) SEQ ID NO: 45, b) nucleotides 1-348 of SEQ ID NO: 13 and nucleotides 268-630 of SEQ ID NO: 21, c) nucleotides 1-408 of SEQ ID NO: 13 and nucleotides 337-630 of SEQ ID NO: 21, d) nucleotides 1-465 of SEQ ID NO: 13 and nucleotides 403-630 of SEQ ID NO: 21, e) nucleotides 1-555 of SEQ ID NO: 13 and nucleotides 490-630 of SEQ ID NO: 21, f) nucleotides 1-624 of SEQ ID NO: 13 and nucleotides 547-630 of SEQ ID NO: 21, g) nucleotides 1-645 of SEQ ID NO: 13 and nucleotides 601-630 of SEQ ID NO: 21, and h) nucleotides 1-717 of SEQ ID NO: 13 and nucleotides 613-630 of SEQ ID NO: 21.

In another preferred embodiment, the gene expression cassette encodes a hybrid polypeptide comprising a transactivation domain comprising an amino acid sequence of SEQ ID NO: 52 or SEQ ID NO: 54 and a chimeric RXR ligand binding domain comprising an amino acid sequence selected from the group consisting of a) SEQ ID NO: 46, b) amino acids 1-116 of SEQ ID NO: 19 and amino acids 90-210 of SEQ ID NO: 27, c) amino acids 1-136 of SEQ ID NO: 19 and amino acids 113-210 of SEQ ID NO: 27, d) amino acids 1-155 of SEQ ID NO: 19 and amino acids 135-210 of SEQ ID NO: 27, e) amino acids 1-185 of SEQ ID NO: 19 and amino acids 164-210 of SEQ ID NO: 27, f) amino acids 1-208 of SEQ ID NO: 19 and amino acids 183-210 of SEQ ID NO: 27, g) amino acids 1-215 of SEQ ID NO: 19 and amino acids 201-210 of SEQ ID NO: 27, and h) amino acids 1-239 of SEQ ID NO: 19 and amino acids 205-210 of SEQ ID NO: 27.

The response element ("RE") may be any response element with a known DNA binding domain, or an analog, combination, or modification thereof. A single RE may be employed or multiple REs, either multiple copies of the same RE or two or more different REs, may be used in the present invention. In a specific embodiment, the RE is an RE from GAL4 ("GAL4RE"), LexA, a steroid/thyroid hormone nuclear receptor RE, or a synthetic RE that recognizes a synthetic DNA binding domain. Preferably, the RE is a GAL4RE comprising a polynucleotide sequence of SEQ ID NO: 55 or a LexARE (operon "op") comprising a polynucleotide sequence of SEQ ID NO: 56 (2XLexAop). Preferably, the first hybrid protein is substantially free of a transactivation domain and the second hybrid protein is substantially free of a DNA binding domain. For purposes of this invention, "substantially free" means that the protein in question does not contain a sufficient sequence of the domain in question to provide activation or binding activity.

Thus, the present invention also relates to a gene expression cassette comprising: i) a response element comprising a domain to which a polypeptide comprising a DNA binding domain binds; ii) a promoter that is activated by a polypeptide comprising a transactivation domain; and iii) a gene whose expression is to be modulated.

Genes of interest for use in Applicants' gene expression cassettes may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for use in Applicants' gene expression cassettes include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Polynucleotides of the Invention

The novel ecdysone receptor/chimeric retinoid X receptor-based inducible gene expression system of the invention comprises a gene expression cassette comprising a polynucleotide that encodes a hybrid polypeptide comprising a) a DNA binding domain or a transactivation domain, and b) an EcR ligand binding domain or a chimeric RXR ligand binding domain. These gene expression cassettes, the polynucleotides they comprise, and the hybrid polypeptides they encode are useful as components of an EcR-based gene expression system to modulate the expression of a gene within a host cell.

Thus, the present invention provides an isolated polynucleotide that encodes a hybrid polypeptide comprising a) a DNA binding domain or a transactivation domain according to the invention, and b) an EcR ligand binding domain or a chimeric RXR ligand binding domain according to the invention.

The present invention also relates to an isolated polynucleotide that encodes a chimeric RXR ligand binding domain according to the invention.

The present invention also relates to an isolated polynucleotide that encodes a truncated EcR LBD or a truncated chimeric RXR LBD comprising a truncation mutation according to the invention. Specifically, the present invention relates to an isolated polynucleotide encoding a truncated EcR or chimeric RXR ligand binding domain comprising a truncation mutation that affects ligand binding activity or ligand sensitivity that is useful in modulating gene expression in a host cell.

In a specific embodiment, the isolated polynucleotide encoding an EcR LBD comprises a polynucleotide sequence selected from the group consisting of SEQ ID NO: 65 (CfEcR-DEF), SEQ ID NO: 59 (CfEcR-CDEF), SEQ ID NO: 67 (DmEcR-DEF), SEQ ID NO: 71 (TmEcR-DEF) and SEQ ID NO: 73 (AmaEcR-DEF).

In another specific embodiment, the isolated polynucleotide encodes an EcR LBD comprising an amino acid sequence selected from the group consisting of SEQ ID NO: 57 (CfEcR-DEF), SEQ ID NO: 70 (CfEcR-CDEF), SEQ ID NO: 58 (DmEcR-DEF), SEQ ID NO: 72 (TmEcR-DEF), and SEQ ID NO: 74 (AmaEcR-DEF).

In another specific embodiment, the isolated polynucleotide encoding a chimeric RXR LBD comprises a polynucleotide sequence selected from the group consisting of a) SEQ ID NO: 45, b) nucleotides 1-348 of SEQ ID NO: 13 and nucleotides 268-630 of SEQ ID NO: 21, c) nucleotides 1-408 of SEQ ID NO: 13 and nucleotides 337-630 of SEQ ID NO: 21, d) nucleotides 1-465 of SEQ ID NO: 13 and nucleotides 403-630 of SEQ ID NO: 21, e) nucleotides 1-555 of SEQ ID NO: 13 and nucleotides 490-630 of SEQ ID NO: 21, f) nucleotides 1-624 of SEQ ID NO: 13 and nucleotides 547-630 of SEQ ID NO: 21, g) nucleotides 1-645 of SEQ ID NO: 13 and nucleotides 601-630 of SEQ ID NO: 21, and h) nucleotides 1-717 of SEQ ID NO: 13 and nucleotides 613-630 of SEQ ID NO: 21.

In another specific embodiment, the isolated polynucleotide encodes a chimeric RXR LBD comprising an amino acid sequence consisting of a) SEQ ID NO: 46, b) amino acids 1-116 of SEQ ID NO: 19 and amino acids 90-210 of SEQ ID NO: 27, c) amino acids 1-136 of SEQ ID NO: 19 and amino acids 113-210 of SEQ ID NO: 27 d) amino acids 1-155 of SEQ ID NO: 19 and amino acids 135-210 of SEQ ID NO: 27 e) amino acids 1-185 of SEQ ID NO: 19 and amino acids 164-210 of SEQ ID NO: 27, f) amino acids 1-208 of SEQ ID NO: 19 and amino acids 183-210 of SEQ ID NO: 27 g) amino acids 1-215 of SEQ ID NO: 19 and amino acids 201-210 of SEQ ID NO: 27, and h) amino acids 1-239 of SEQ ID NO: 19 and amino acids 205-210 of SEQ ID NO: 27.

In particular, the present invention relates to an isolated polynucleotide encoding a truncated chimeric RXR LBD comprising a truncation mutation, wherein the mutation reduces ligand binding activity or ligand sensitivity of the truncated chimeric RXR LBD. In a specific embodiment, the present invention relates to an isolated polynucleotide encoding a truncated chimeric RXR LBD comprising a truncation mutation that reduces steroid binding activity or steroid sensitivity of the truncated chimeric RXR LBD.

In another specific embodiment, the present invention relates to an isolated polynucleotide encoding a truncated chimeric RXR LBD comprising a truncation mutation that reduces non-steroid binding activity or non-steroid sensitivity of the truncated chimeric RXR LBD.

The present invention also relates to an isolated polynucleotide encoding a truncated chimeric RXR LBD comprising a truncation mutation, wherein the mutation enhances ligand binding activity or ligand sensitivity of the truncated chimeric RXR LBD. In a specific embodiment, the present invention relates to an isolated polynucleotide encoding a truncated chimeric RXR LBD comprising a truncation mutation that enhances steroid binding activity or steroid sensitivity of the truncated chimeric RXR LBD.

In another specific embodiment, the present invention relates to an isolated polynucleotide encoding a truncated chimeric RXR LBD comprising a truncation mutation that enhances non-steroid binding activity or non-steroid sensitivity of the truncated chimeric RXR LBD.

The present invention also relates to an isolated polynucleotide encoding a truncated chimeric retinoid X receptor LBD comprising a truncation mutation that increases ligand sensitivity of a heterodimer comprising the truncated chimeric retinoid X receptor LBD and a dimerization partner. In a specific embodiment, the dimerization partner is an ecdysone receptor polypeptide. Preferably, the dimerization partner is a truncated EcR polypeptide. More preferably, the dimerization partner is an EcR polypeptide in which domains A/B have been deleted. Even more preferably, the dimerization partner is an EcR polypeptide comprising an amino acid sequence of SEQ ID NO: 57 (CfEcR-DEF), SEQ ID NO: 58 (DmEcR-DEF), SEQ ID NO: 70 (CfEcR-CDEF), SEQ ID NO: 72 (TmEcR-DEF) or SEQ ID NO: 74 (AmaEcR-DEF).

Polypeptides of the Invention

The novel ecdysone receptor/chimeric retinoid X receptor-based inducible gene expression system of the invention comprises a gene expression cassette comprising a polynucleotide that encodes a hybrid polypeptide comprising a) a DNA binding domain or a transactivation domain, and b) an EcR ligand binding domain or a chimeric RXR ligand binding domain. These gene expression cassettes, the polynucleotides they comprise, and the hybrid polypeptides they encode are useful as components of an EcR/chimeric RXR-based gene expression system to modulate the expression of a gene within a host cell.

Thus, the present invention also relates to a hybrid polypeptide comprising a) a DNA binding domain or a transactivation domain according to the invention, and b) an EcR ligand binding domain or a chimeric RXR ligand binding domain according to the invention.

The present invention also relates to an isolated polypeptide comprising a chimeric RXR ligand binding domain according to the invention.

The present invention also relates to an isolated truncated EcR LBD or an isolated truncated chimeric RXR LBD comprising a truncation mutation according to the invention. Specifically, the present invention relates to an isolated truncated EcR LBD or an isolated truncated chimeric RXR LBD comprising a truncation mutation that affects ligand binding activity or ligand sensitivity.

In a specific embodiment, the isolated EcR LBD polypeptide is encoded by a polynucleotide comprising a polynucleotide sequence selected from the group consisting of SEQ ID NO: 65 (CfEcR-DEF), SEQ ID NO: 59 (CfEcR-CDEF), SEQ ID NO: 67 (DmEcR-DEF), SEQ ID NO: 71 (TmEcR-DEF) and SEQ ID NO: 73 (AmaEcR-DEF).

In another specific embodiment, the isolated EcR LBD polypeptide comprises an amino acid sequence selected from the group consisting of SEQ ID NO: 57 (CfEcR-DEF), SEQ ID NO: 70 (CfEcR-CDEF), SEQ ID NO: 58 (DmEcR-DEF), SEQ ID NO: 72 (TmEcR-DEF), and SEQ ID NO: 74 (AmaEcR-DEF).

In another specific embodiment, the isolated truncated chimeric RXR LBD is encoded by a polynucleotide comprising a polynucleotide sequence selected from the group consisting of a) SEQ ID NO: 45, b) nucleotides 1-348 of SEQ ID NO: 13 and nucleotides 268-630 of SEQ ID NO: 21, c) nucleotides 1-408 of SEQ ID NO: 13 and nucleotides 337-630 of SEQ ID NO: 21, d) nucleotides 1-465 of SEQ ID NO: 13 and nucleotides 403-630 of SEQ ID NO: 21, e) nucleotides 1-555 of SEQ ID NO: 13 and nucleotides 490-630 of SEQ ID NO: 21, f) nucleotides 1-624 of SEQ ID NO: 13 and nucleotides 547-630 of SEQ ID NO: 21, g) nucleotides 1-645 of SEQ ID NO: 13 and nucleotides 601-630 of SEQ ID NO: 21, and h) nucleotides 1-717 of SEQ ID NO: 13 and nucleotides 613-630 of SEQ ID NO: 21.

In another specific embodiment, the isolated truncated chimeric RXR LBD comprises an amino acid sequence selected from the group consisting of a) SEQ ID NO: 46, b) amino acids 1-116 of SEQ ID NO: 19 and amino acids 90-210 of SEQ ID NO: 27, c) amino acids 1-136 of SEQ ID NO: NO: 19 and amino acids 113-210 of SEQ ID NO: 27, d) amino acids 1-155 of SEQ ID NO: 19 and amino acids 135-210 of SEQ ID NO: 27, e) amino acids 1-185 of SEQ ID NO: 19 and amino acids 164-210 of SEQ ID NO: 27, f) amino acids 1-208 of SEQ ID NO: 19 and amino acids 183-210 of SEQ ID NO: 27, g) amino acids 1-215 of SEQ ID NO: 19 and amino acids 201-210 of SEQ ID NO: 27, and h) amino acids 1-239 of SEQ ID NO: 19 and amino acids 205-210 of SEQ ID NO: 27.

The present invention relates to an isolated truncated chimeric RXR LBD comprising a truncation mutation that reduces ligand binding activity or ligand sensitivity of the truncated chimeric RXR LBD.

Thus, the present invention relates to an isolated truncated chimeric RXR LBD comprising a truncation mutation that reduces ligand binding activity or ligand sensitivity of the truncated chimeric RXR LBD.

In a specific embodiment, the present invention relates to an isolated truncated chimeric RXR LBD comprising a truncation mutation that reduces steroid binding activity or steroid sensitivity of the truncated chimeric RXR LBD.

In another specific embodiment, the present invention relates to an isolated truncated chimeric RXR LBD comprising a truncation mutation that reduces non-steroid binding activity or non-steroid sensitivity of the truncated chimeric RXR LBD.

In addition, the present invention relates to an isolated truncated chimeric RXR LBD comprising a truncation mutation that enhances ligand binding activity or ligand sensitivity of the truncated chimeric RXR LBD.

The present invention relates to an isolated truncated chimeric RXR LBD comprising a truncation mutation that enhances ligand binding activity or ligand sensitivity of the truncated chimeric RXR LBD. In a specific embodiment, the present invention relates to an isolated truncated chimeric RXR LBD comprising a truncation mutation that enhances steroid binding activity or steroid sensitivity of the truncated chimeric RXR LBD.

In another specific embodiment, the present invention relates to an isolated truncated chimeric RXR LBD comprising a truncation mutation that enhances non-steroid binding activity or non-steroid sensitivity of the truncated chimeric RXR LBD.

The present invention also relates to an isolated truncated chimeric RXR LBD comprising a truncation mutation that increases ligand sensitivity of a heterodimer comprising the truncated chimeric RXR LBD and a dimerization partner.

In a specific embodiment, the dimerization partner is an ecdysone receptor polypeptide. Preferably, the dimerization partner is a truncated EcR polypeptide. Preferably, the dimerization partner is an EcR polypeptide in which domains A/B or A/B/C have been deleted. Even more preferably, the dimerization partner is an EcR polypeptide comprising an amino acid sequence of SEQ ID NO: 57 (CfEcR-DEF), SEQ ID NO: 58 (DmEcR-DEF), SEQ ID NO: 70 (CfEcR-CDEF), SEQ ID NO: 72 (TmEcR-DEF) or SEQ ID NO: 74 (AmaEcR-DEF).

Method of Modulating Gene Expression of the Invention

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the first hybrid polypeptide; ii) a promoter that is activated by the transactivation domain of the second hybrid polypeptide; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette comprising i) a response element comprising a domain recognized by the DNA binding domain from the first hybrid polypeptide; ii) a promoter that is activated by the transactivation domain of the second hybrid polypeptide; and iii) a gene whose expression is to be modulated; and c) introducing into the host cell a ligand; whereby expression of the gene is modulated in the host cell.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Acceptable ligands are any that modulate expression of the gene when binding of the DNA binding domain of the two-hybrid system to the response element in the presence of the ligand results in activation or suppression of expression of the genes. Preferred ligands include ponasterone, muristerone A, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-allyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl-4-hydroxy-N-isobutyl-benzamide, 8-O-acetylharpagide, and the like.

In a preferred embodiment, the ligand for use in Applicants' method of modulating expression of gene is a compound of the formula:

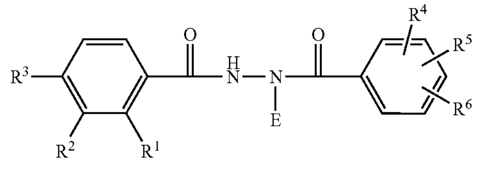

wherein:

E is a $(C_4-C_6)$alkyl containing a tertiary carbon or a cyano $(C_3-C_5)$alkyl containing a tertiary carbon;

$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, OH, OMe, OEt, cyclopropyl, $CF_2CF_3$, CH═CHCN, allyl, azido, SCN, or $SCHF_2$;

$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C°CH, 1-propynyl, 2-propynyl, vinyl, Ac, F, Cl, OH, OMe, OEt, O-n-Pr, OAc, $NMe_2$, $NEt_2$, SMe, SEt, $SOCF_3$, $OCF_2CF_2H$, COEt, cyclopropyl, $CF_2CF_3$, CH═CHCN, allyl, azido, $OCF_3$, $OCHF_2$, O-i-Pr, SCN, $SCHF_2$, SOMe, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;

$R^4$, $R^5$, and $R^6$ are independently H, Me, Et, F, Cl, Br, formyl, $CF_3$, $CHF_2$, $CHCl_2$, $CH_2F$, $CH_2Cl$, $CH_2OH$, CN, C°CH, 1-propynyl, 2-propynyl, vinyl, OMe, OEt, SMe, or SEt.

In another preferred embodiment, a second ligand may be used in addition to the first ligand discussed above in Applicants' method of modulating expression of a gene, wherein the second ligand is 9-cis-retinoic acid or a synthetic analog of retinoic acid.

Applicants' invention provides for modulation of gene expression in prokaryotic and eukaryotic host cells. Thus, the present invention also relates to a method for modulating gene expression in a host cell selected from the group consisting of a bacterial cell, a fungal cell, a yeast cell, an animal cell, and a mammalian cell. Preferably, the host cell is a yeast cell, a hamster cell, a mouse cell, a monkey cell, or a human cell.

Expression in transgenic host cells may be useful for the expression of various polypeptides of interest including but not limited to therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Host Cells and Non-Human Organisms of the Invention

As described above, the gene expression modulation system of the present invention may be used to modulate gene expression in a host cell. Expression in transgenic host cells may be useful for the expression of various genes of interest. Thus, Applicants' invention provides an isolated host cell comprising a gene expression system according to the invention. The present invention also provides an isolated host cell comprising a gene expression cassette according to the invention. Applicants' invention also provides an isolated host cell comprising a polynucleotide or a polypeptide according to the invention. The isolated host cell may be either a prokaryotic or a eukaryotic host cell.

Preferably, the host cell is selected from the group consisting of a bacterial cell, a fungal cell, a yeast cell, an animal cell, and a mammalian cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*, animal, and mammalian host cells.

In a specific embodiment, the host cell is a yeast cell selected from the group consisting of a *Saccharomyces*, a *Pichia*, and a *Candida* host cell.

In another specific embodiment, the host cell is a hamster cell.

In another specific embodiment, the host cell is a murine cell.

In another specific embodiment, the host cell is a monkey cell.

In another specific embodiment, the host cell is a human cell.

Host cell transformation is well known in the art and may be achieved by a variety of methods including but not limited to electroporation, viral infection, plasmid/vector transfection, non-viral vector mediated transfection, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. Preferably, the non-human organism is selected from the group consisting of a bacterium, a fungus, a yeast, an animal, and a mammal. More preferably, the non-human organism is a yeast, a mouse, a rat, a rabbit, a cat, a dog, a bovine, a goat, a pig, a horse, a sheep, a monkey, or a chimpanzee.

In a specific embodiment, the non-human organism is a yeast selected from the group consisting of *Saccharomyces, Pichia*, and *Candida*.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybidizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "μl" means microliter(s), "ml" means milliliter(s), "L" means liter(s), "μM" means micromolar, "mM" means millimolar, "μg" means microgram(s), "mg" means milligram(s), "A" means adenine or adenosine, "T" means thymine or thymidine, "G" means guanine or guanosine, "C" means cytidine or cytosine, "×g" means times gravity, "nt" means nucleotide(s), "aa" means amino acid(s), "bp" means base pair(s), "kb" means kilobase(s), "k" means kilo, "μ" means micro, and "° C." means degrees Celsius.

Example 1

Applicants' EcR/chimeric RXR-based inducible gene expression modulation system is useful in various applications including gene therapy, expression of proteins of interest in host cells, production of transgenic organisms, and cell-based assays. Applicants have made the surprising discovery that a chimeric retinoid X receptor ligand binding domain can substitute for either parent RXR polypeptide and function inducibly in an EcR/chimeric RXR-based gene expression modulation system upon binding of ligand. In addition, the chimeric RXR polypeptide may also function better than either parent/donor RXR ligand binding domain. Applicants' surprising discovery and unexpected superior results provide a novel inducible gene expression system for bacterial, fungal, yeast, animal, and mammalian cell applications. This Example describes the construction of several gene expression cassettes for use in the EcR/chimeric RXR-based inducible gene expression system of the invention.

Applicants constructed several EcR-based gene expression cassettes based on the spruce budworm *Choristoneura fumiferana* EcR ("CfEcR"), *C. fumiferana* ultraspiracle ("CfUSP"), *Drosophila melanogaster* EcR ("DmEcR"), *D. melanogaster* USP ("DmUSP"), *Tenebrio Molitor* EcR ("TmEcR"), *Amblyomma americanum* EcR("AmaEcR"), *A. americanum* RXR homolog 1 ("AmaRXR1"), *A. americanum* RXR homolog 2 ("AmaRXR2"), mouse *Mus musculus* retinoid X receptor α isoform ("MmRXRα"), human *Homo sapiens* retinoid X receptor β isoform ("HsRXRβ"), and locust *Locusta migratoria* ultraspiracle ("LmUSP").

The prepared receptor constructs comprise 1) an EcR ligand binding domain (LBD), a vertebrate RXR (MmRXRα or HsRXRβ) LBD, an invertebrate USP (CfUSP or DmUSP) LBD, an invertebrate RXR (LmUSP, AmaRXR1 or AmaRXR2) LBD, or a chimeric RXR LBD comprising a vertebrate RXR LBD fragment and an invertebrate RXR LBD fragment; and 2) a GAL4 or LexA DNA binding domain (DBD) or a VP16 or B42 acidic activator transactivation domain (AD). The reporter constructs include a reporter gene, luciferase or LacZ, operably linked to a synthetic promoter construct that comprises either a GAL4 response element or a LexA response element to which the Gal4 DBD or LexA DBD binds, respectively. Various combinations of these receptor and reporter constructs were cotransfected into mammalian cells as described in Examples 2-6 infra.

Gene Expression Cassettes:

Ecdysone receptor-based gene expression cassette pairs (switches) were constructed as followed, using standard cloning methods available in the art. The following is brief description of preparation and composition of each switch used in the Examples described herein.

1.1—GAL4CfEcR-CDEF/VP16MmRXRα-EF: The C, D, E, and F domains from spruce budworm *Choristoneura fumiferana* EcR ("CfEcR-CDEF"; SEQ ID NO: 59) were fused to a GAL4 DNA binding domain ("Gal4DNABD" or "Gal4DBD"; SEQ ID NO: 47) and placed under the control of an SV40e promoter (SEQ ID NO: 60). The EF domains from mouse *Mus musculus* RXRα ("MmRXRα-EF"; SEQ ID NO: 9) were fused to the transactivation domain from VP16 ("VP16AD"; SEQ ID NO: 51) and placed under the control of an SV40e promoter (SEQ ID NO: 60). Five consensus GAL4 response element binding sites ("5XGAL4RE"; comprising 5 copies of a GAL4RE comprising SEQ ID NO: 55) were fused to a synthetic E1b minimal promoter (SEQ ID NO: 61) and placed upstream of the luciferase gene (SEQ ID NO: 62).

1.2—Gal4CfEcR-CDEF/VP16LmUSP-EF: This construct was prepared in the same way as in switch 1.1 above except MmRXRα-EF was replaced with the EF domains from *Locusta Migratoria* ultraspiracle ("LmUSP-EF"; SEQ ID NO: 21).

1.3—Gal4CfEcR-CDEF/VP16MmRXRα(1-7)-LmUSP(8-12)-EF: This construct was prepared in the same way as in switch 1.1 above except MmRXRα-EF was replaced with helices 1 through 7 of MmRXRα-EF and helices 8 through 12 of LmUSP-EF (SEQ ID NO: 45).

1.4—Gal4CfEcR-CDEF/VP16MmRXRα(1-7)-LmUSP(8-12)-EF-MmRXRα-F: This construct was prepared in the same way as in switch 1.1 above except MmRXRα-EF was replaced with helices 1 through 7 of MmRXRα-EF and helices 8 through 12 of LmUSP-EF (SEQ ID NO: 45), and wherein the last C-terminal 18 nucleotides of SEQ ID NO: 45 (F domain) were replaced with the F domain of MmRXRα ("MmRXRα-F", SEQ ID NO: 63).

1.5—Gal4CfEcR-CDEF/VP16MmRXRα(1-12)-EF-LmUSP-F: This construct was prepared in the same way as in switch 1.1 above except MmRXRα-EF was replaced with helices 1 through 12 of MmRXRα-EF (SEQ ID NO: 9) and wherein the last C-terminal 18 nucleotides of SEQ ID NO: 9 (F domain) were replaced with the F domain of LmUSP ("LmUSP-F", SEQ ID NO: 64).

1.6—Gal4CfEcR-CDEF/VP16LmUSP(1-12)-EF-MmRXRα-F: This construct was prepared in the same way as in switch 1.1 above except MmRXRα-EF was replaced with helices 1 through 12 of LmUSP-EF (SEQ ID NO: 21) and wherein the last C-terminal 18 nucleotides of SEQ ID NO: 21 (F domain) were replaced with the F domain of MmRXRα ("MmRXRα-F", SEQ ID NO: 63).

1.7—GAL4CfEcR-DEF/VP16CfUSP-EF: The D, E, and F domains from spruce budworm *Choristoneura fumiferana* EcR ("CfEcR-DEF"; SEQ ID NO: 65) were fused to a GAL4 DNA binding domain ("Gal4DNABD" or "Gal4DBD"; SEQ ID NO: 47) and placed under the control of an SV40e promoter (SEQ ID NO: 60). The EF domains from *C. fumiferana* USP ("CfUSP-EF"; SEQ ID NO: 66) were fused to the transactivation domain from VP16 ("VP16AD"; SEQ ID NO: 51) and placed under the control of an SV40e promoter (SEQ ID NO: 60). Five consensus GAL4 response element binding sites ("5XGAL4RE"; comprising 5 copies of a GAL4RE comprising SEQ ID NO: 55) were fused to a synthetic E1b minimal promoter (SEQ ID NO: 61) and placed upstream of the luciferase gene (SEQ ID NO: 62).

1.8—GAL4CfEcR-DEF/VP16DmUSP-EF: This construct was prepared in the same way as in switch 1.7 above except CfUSP-EF was replaced with the corresponding EF domains from fruit fly *Drosophila melanogaster* USP ("DmUSP-EF", SEQ ID NO: 75).

1.9—Gal4CfEcR-DEF/VP16LmUSP-EF: This construct was prepared in the same way as in switch 1.7 above except CfUSP-EF was replaced with the EF domains from *Locusta migratoria* USP ("LmUSP-EF"; SEQ ID NO: 21).

1.10—GAL4CfEcR-DEF/VP16MmRXRα-EF: This construct was prepared in the same way as in switch 1.7 above except CfUSP-EF was replaced with the EF domains of *M. musculus* MmRXRα ("MmRXRα-EF", SEQ ID NO: 9).

1.11—GAL4CfEcR-DEF/VP16MmRXRα-EF: This construct was prepared in the same way as in switch 1.7 above except CfUSP-EF was replaced with the EF domains of *Amblyomma americanum* RXR homolog 1 ("AmaRXR1-EF", SEQ ID NO: 22).

1.12—GAL4CfEcR-DEF/VP16MmRXRα-EF: This construct was prepared in the same way as in switch 1.7 above except CfUSP-EF was replaced with the EF domains of tick *A. americanum* RXR homolog 2 ("AmaRXR2-EF", SEQ ID NO: 23).

1.13—Gal4CfEcR-DEF/VP16MmRXRα(1-7)-LmUSP(8-12)-EF ("αChimera#7"): This construct was prepared in the same way as in switch 1.7 above except CfUSP-EF was replaced with helices I through 7 of MmRXRα-EF and helices 8 through 12 of LmUSP-EF (SEQ ID NO: 45).

1.14—GAL4DmEcR-DEF/VP16CfUSP-EF: The D, E, and F domains from fruit fly *Drosophila melanogaster* EcR ("DmEcR-DEF"; SEQ ID NO: 67) were fused to a GAL4 DNA binding domain ("Gal4DNABD" or "Gal4DBD"; SEQ ID NO: 47) and placed under the control of an SV40e promoter (SEQ ID NO: 60). The EF domains from *C. fumiferana*

USP ("CfUSP-EF"; SEQ ID NO: 66) were fused to the transactivation domain from VP16 ("VP16AD"; SEQ ID NO: 51) and placed under the control of an SV40e promoter (SEQ ID NO: 60). Five consensus GAL4 response element binding sites ("5XGAL4RE"; comprising 5 copies of a GAL4RE comprising SEQ ID NO: 55) were fused to a synthetic E1b minimal promoter (SEQ ID NO: 61) and placed upstream of the luciferase gene (SEQ ID NO: 62).

1.15—GAL4DmEcR-DEF/VP16DmUSP-EF: This construct was prepared in the same way as in switch 1.14 above except CfUSP-EF was replaced with the corresponding EF domains from fruit fly *Drosophila melanogaster* USP ("DmUSP-EF", SEQ ID NO: 75).

1.16—Gal4DmEcR-DEF/VP16LmUSP-EF: This construct was prepared in the same way as in switch 1.14 above except CfUSP-EF was replaced with the EF domains from *Locusta migratoria* USP ("LmUSP-EF"; SEQ ID NO: 21).

1.17—GAL4DmEcR-DEF/VP16MmRXRα-EF: This construct was prepared in the same way as in switch 1.14 above except CfUSP-EF was replaced with the EF domains of *Mus musculus* MmRXRα ("MmRXRα-EF", SEQ ID NO: 9).

1.18—GAL4DmEcR-DEF/VP16AmaRXR1-EF: This construct was prepared in the same way as in switch 1.14 above except CfUSP-EF was replaced with the EF domains of ixodid tick *Amblyomma americanum* RXR homolog 1 ("AmaRXR1-EF", SEQ ID NO: 22).

1.19—GAL4DmEcR-DEF/VP16AmaRXR2-EF: This construct was prepared in the same way as in switch 1.14 above except CfUSP-EF was replaced with the EF domains of ixodid tick *A. americanum* RXR homolog 2 ("AmaRXR2-EF", SEQ ID NO: 23).

1.20—GAl4DmEcR-DEF/VP16MmRXRα(1-7)-LmUSP (8-12)-EF: This construct was prepared in the same way as in switch 1.14 above except CfUSP-EF was replaced with helices 1 through 7 of MmRXRα-EF and helices 8 through 12 of LmUSP-EF (SEQ ID NO: 45).

1.21—GAL4TmEcR-DEF/VP16MmRXRα(1-7)-LmUSP (8-12)-EF: This construct was prepared in the same way as in switch 1.20 above except DmEcR-DEF was replaced with the corresponding D, E, and F domains from beetle *Tenebrio molitor* EcR ("TmEcR-DEF", SEQ ID NO: 71), fused to a GAL4 DNA binding domain ("Gal4DNABD" or "Gal4DBD"; SEQ ID NO: 47) and placed under the control of an SV40e promoter (SEQ ID NO: 60). Chimeric EF domains comprising helices 1 through 7 of MmRXRα-EF and helices 8 through 12 of LmUSP-EF (SEQ ID NO: 45) were fused to the transactivation domain from VP16 ("VP16AD"; SEQ ID NO: 51) and placed under the control of an SV40e promoter (SEQ ID NO: 60). Five consensus GAL4 response element binding sites ("5XGAL4RE"; comprising 5 copies of a GAL4RE comprising SEQ ID NO: 55) were fused to a synthetic E1b minimal promoter (SEQ ID NO: 61) and placed upstream of the luciferase gene (SEQ ID NO: 62).

1.22—GAl4AmaEcR-DEF/VP16MmRXRα(1-17)-LmUSP (8-12)-EF: This construct was prepared in the same way as in switch 1.21 above except TmEcR-DEF was replaced with the corresponding DEF domains of tick *Amblyomma americanum* EcR ("AmaEcR-DEF", SEQ ID NO: 73).

1.23—GAL4CfEcR-CDEF/VP16HsRXRβ-EF: The C, D, E, and F domains from spruce budworm *Choristoneura fumiferana* EcR ("CfEcR-CDEF"; SEQ ID NO: 59) were fused to a GAL4 DNA binding domain ("Gal4DNABD" or "Gal4DBD"; SEQ ID NO: 47) and placed under the control of an SV40e promoter (SEQ ID NO: 60). The EF domains from human *Homo sapiens* RXRβ ("HsRXRβ-EF"; SEQ ID NO: 13) were fused to the transactivation domain from VP16 ("VP16AD"; SEQ ID NO: 51) and placed under the control of an SV40e promoter (SEQ ID NO: 60). Five consensus GAL4 response element binding sites ("5XGAL4RE"; comprising 5 copies of a GAL4RE comprising SEQ ID NO: 55) were fused to a synthetic E1b minimal promoter (SEQ ID NO: 61) and placed upstream of the luciferase gene (SEQ ID NO: 62).

1.24—GAL4CfEcR-DEF/VP16HsRXRβ-EF: This construct was prepared in the same way as in switch 1.23 above except CfEcR-CDEF was replaced with the DEF domains of *C. fumiferana* EcR ("CfEcR-DEF"; SEQ ID NO: 65).

1.25—GAL4CfEcR-DEF/VP16HsRXRβ(1-6)-LmUSP(7-12)-EF ("βChimera #6"): This construct was prepared in the same way as in switch 1.24 above except HsRXRβ-EF was replaced with helices 1 through 6 of HsRXRβ-EF (nucleotides 1-348 of SEQ ID NO: 13) and helices 7 through 12 of LmUSP-EF (nucleotides 268-630 of SEQ ID NO: 21).

1.26—GAL4CfEcR-DEF/VP16HsRXRβ(1-7)-LmUSP(8-12)-EF ("βChimera #8"): This construct was prepared in the same way as in switch 1.24 above except HsRXRβ-EF was replaced with helices 1 through 7 of HsRXRβ-EF (nucleotides 1-408 of SEQ ID NO: 13) and helices 8 through 12 of LmUSP-EF (nucleotides 337-630 of SEQ ID NO: 21).

1.27—GAL4CfEcR-DEF/VP16HsRXRβ(1-8)-LmUSP(9-12)-EF ("βChimera #9"): This construct was prepared in the same way as in switch 1.24 above except HsRXRβ-EF was replaced with helices 1 through 8 of HsRXRβ-EF (nucleotides 1-465 of SEQ ID NO: 13) and helices 9 through 12 of LmUSP-EF (nucleotides 403-630 of SEQ ID NO: 21).

1.28—GAL4CfEcR-DEF/VP16HsRXRβ(1-9)-LmUSP(10-12)-EF ("βChimera #10"): This construct was prepared in the same way as in switch 1.24 above except HsRXRβ-EF was replaced with helices 1 through 9 of HsRXRβ-EF (nucleotides 1-555 of SEQ ID NO: 13) and helices 10 through 12 of LmUSP-EF (nucleotides 490-630 of SEQ ID NO: 21).

1.29—GAL4CfEcR-DEF/VP16HsRXRβ(1-10)-LmUSP (11-12)-EF ("Chimera #1"): This construct was prepared in the same way as in switch 1.24 above except HsRXRβ-EF was replaced with helices 1 through 10 of HsRXRβ-EF (nucleotides 1-624 of SEQ ID NO: 13) and helices 11 through 12 of LmUSP-EF (nucleotides 547-630 of SEQ ID NO: 21).

1.30—GAL4DmEcR-DEF/VP16HsRXRβ(1-6)-LmUSP(7-12)-EF ("βChimera #6"): This construct was prepared in the same way as in switch 1.25 above except CfEcR-DEF was replaced with DmEcR-DEF (SEQ ID NO: 67).

1.31—GAL4DmEcR-DEF/VP16HsRXRβ(1-7)-LmUSP(8-12)-EF ("βChimera #8"): This construct was prepared in the same way as in switch 1.26 above except CfEcR-DEF was replaced with DmEcR-DEF (SEQ ID NO: 67).

1.32—GAL4DmEcR-DEF/VP16HsRXRβ(1-8)-LmUSP(9-12)-EF ("βChimera #9"): This construct was prepared in the same way as in switch 1.27 above except CfEcR-DEF was replaced with DmEcR-DEF (SEQ ID NO: 67).

1.33—GAL4DmEcR-DEF/VP16HsRXRβ(1-9)-LmUSP (10-12)-EF ("βChimera #10"): This construct was prepared in the same way as in switch 1.28 above CfEcR-DEF was replaced with DmEcR-DEF (SEQ ID NO: 67).

1.34—GAL4DmEcR-DEF/VP16HsRXRβ(1-10)-LmUSP (11-12)-EF ("βChimera #11"): This construct was prepared in the same way as in switch 1.29 above except CfEcR-DEF was replaced with DmEcR-DEF (SEQ ID NO: 67).

Example 2

Applicants have recently made the surprising discovery that invertebrate RXRs and their non-Lepidopteran and non-Dipteran RXR homologs can function similarly to or better than vertebrate RXRs in an ecdysone receptor-based inducible gene expression modulation system in both yeast and mammalian cells (U.S. provisional application Ser. No. 60/294,814). Indeed, Applicants have demonstrated that LmUSP is a better partner for CfEcR than mouse RXR in mammalian cells. Yet for most gene expression system applications, particularly those destined for mammalian cells, it is desirable to have a vertebrate RXR as a partner. To identify a minimum region of LmUSP required for this improvement, Applicants have constructed and analyzed vertebrate RXR/invertebrate RXR chimeras (referred to herein interchangeably as "chimeric RXR's" or "RXR chimeras") in an EcR-based inducible gene expression modulation system. Briefly, gene induction potential (magnitude of induction) and ligand specificity and sensitivity were examined using a non-steroidal ligand in a dose-dependent induction of reporter gene expression in the transfected NIH3T3 cells and A549 cells.

In the first set of RXR chimeras, helices 8 to 12 from MmRXRα-EF were replaced with helices 8 to 12 from LmUSP-EF (switch 1.3 as prepared in Example 1). Three independent clones (RXR chimeras Cb #1, Ch #2, and Ch #3 in FIGS. 1-3) were picked and compared with the parental MmRXRα-EF and LmUSP-EF switches (switches 1.1 and 1.2, respectively, as prepared in Example 1). The RXR chimera and parent DNAs were transfected into mouse NIH3T3 cells along with Gal4/CfEcR-CDEF and the reporter plasmid pFRLuc. The transfected cells were grown in the presence of 0, 0.2, 1, 5, and 10 μM non-steroidal ligand N-(2-ethyl-3-methoxybenzoyl)-N'-(3,5-dimethylbenzoyl)-N'-tert-butylhydrazine (GS-E™ ligand). The cells were harvested at 48 hours post treatment and the reporter activity was assayed. The numbers on top of bars correspond to the maximum fold activation/induction for that treatment.

Transfections:

DNAs corresponding to the various switch constructs outlined in Example 1, specifically switches 1.1 through 1.6 were transfected into mouse NH3T3 cells (ATCC) and human A549 cells (ATCC) as follows. Cells were harvested when they reached 50% confluency and plated in 6-, 12- or 24-well plates at 125,000, 50,000, or 25,000 cells, respectively, in 2.5, 1.0, or 0.5 ml of growth medium containing 10% fetal bovine serum (FBS), respectively. NIH3T3 cells were grown in Dulbecco's modified Eagle medium (DMEM; LifeTechnologies) and A549 cells were grown in F12K-nutrient mixture (LifeTechnologies). The next day, the cells were rinsed with growth medium and transfected for four hours. Superfect™ (Qiagen Inc.) was found to be the best transfection reagent for 3T3 cells and A549 cells. For 12-well plates, 4 μl of Superfect™ was mixed with 100 μl of growth medium 1.0 μg of reporter construct and 0.25 μg of each receptor construct of the receptor pair to be analyzed were added to the transfection mix. A second reporter construct was added [pTKRL (Promega), 0.1 μg/transfection mix] that comprises a *Renilla luciferase* gene operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 400 μl growth medium. The cells were maintained at 37° C. and 5% $CO_2$ for four hours. At the end of incubation, 500 μl of growth medium containing 20% FBS and either dimethylsulfoxide (DMSO; control) or a DMSO solution of 0.2, 1, 5, 10, and 50 μM N-(2-ethyl-3-methoxybenzoyl)N'-(3,5-dimethylbenzoyl)-N'-tert-butylhydrazine non-steroidal ligand was added and the cells were maintained at 37° C. and 5% $CO_2$ for 48 hours. The cells were harvested and reporter activity was assayed. The same procedure was followed for 6 and 24 well plates as well except all the reagents were doubled for 6 well plates and reduced to half for 24-well plates.

Ligand:

The non-steroidal ligand N-(2-ethyl-3-methoxybenzoyl)-N'-(3,5-dimethylbenzoyl)-N'-t-butylhydrazine (GS™-E non-steroidal ligand) is a synthetic stable ecdysteroid ligand synthesized at Rohm and Haas Company. Ligands were dissolved in DMSO and the final concentration of DMSO was maintained at 0.1% in both controls and treatments.

Reporter Assays:

Cells were harvested 48 hours after adding ligands. 125, 250, or 500 μl of passive lysis buffer (part of Dual-luciferase™ reporter assay system from Promega Corporation) were added to each well of 24- or 12- or 6-well plates respectively. The plates were placed on a rotary shaker for 15 minutes. Twenty μl of lysate were assayed. Luciferase activity was measured using Dual-luciferase™ reporter assay system from Promega Corporation following the manufacturer's instructions. β-Galactosidase was measured using Galacto-Star™ assay kit from TROPIX following the manufacturer's instructions. All luciferase and β-galactosidase activities were normalized using *Renilla* luciferase as a standard. Fold activities were calculated by dividing normalized relative light units ("RLU") in ligand treated cells with normalized RLU in DMSO treated cells (untreated control).

Results:

Surprisingly, all three independent clones of the RXR chimera tested (switch 1.3) were better than either parent-based switch, MmRXRα-EF (switch 1.1) and LmUSP-EF (switch 1.2), see FIG. 1. In particular, the chimeric RXR demonstrated increased ligand sensitivity and increased magnitude of induction. Thus, Applicants have made the surprising discovery that a chimeric RXR ligand binding domain may be used in place of a vertebrate RXR or an invertebrate RXR in an EcR-based inducible gene expression modulation system. This novel EcR/chimeric RXR-based gene expression system provides an improved system characterized by both increased ligand sensitivity and increased magnitude of induction.

Figure 2:
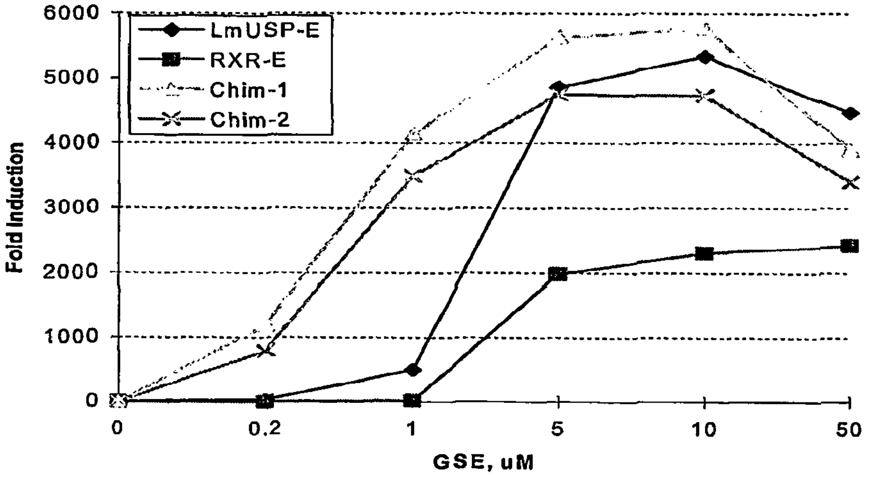
FIG. 2: Expression data of VP16LmUSP-EF, VP16MmRXRα-EF and two independent clones of VP16MmRXRα(1-7)-LmUSP (8-12)-EF in NIH3T3 cells along with GAL4CfEcR-CDEF and pFRLuc in the presence of non-steroid (GSE) ligand.

The best two RXR chimeras clones of switch 1.3 ("Ch #1" and "Ch #2" of FIG. 2) were compared with the parent-based switches 1.1 and 1.2 in a repeated experiment ("Chim-1" and "Chim-2" in FIG. 2, respectively). In this experiment, the chimeric RXR-based switch was again more sensitive to non-steroidal ligand than either parent-based switch (see FIG. 2). However, in this experiment, the chimeric RXR-based switch was better than the vertebrate RXR (MmRXRα-EF)-based switch for magnitude of induction but was similar to the invertebrate RXR (LmUSP-EF)-based switch.

Figure 3:
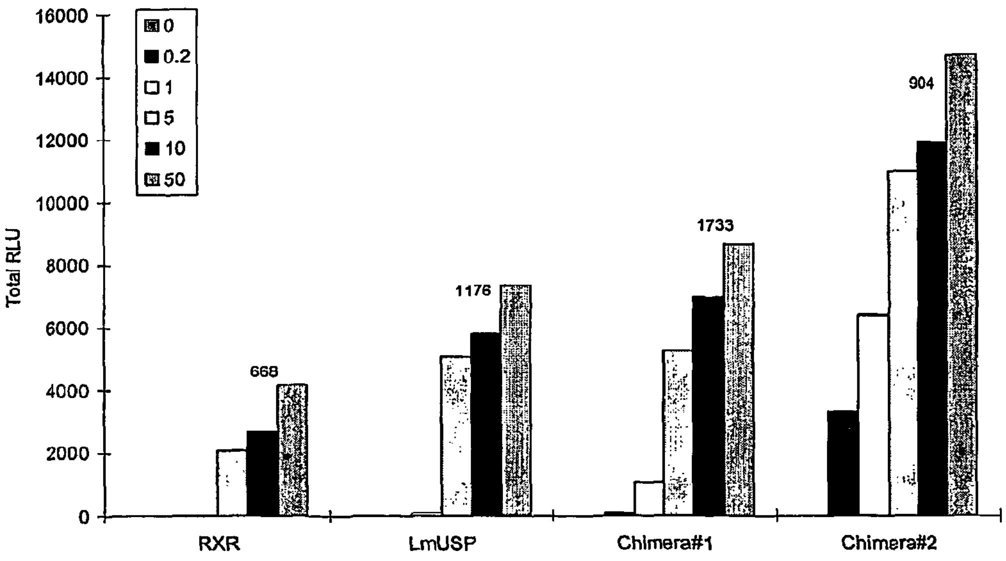
FIG. 3: Expression data of VP16LmUSP-EF, VP16MmRXRα-EF and two independent clones of VP16MmRXRα(1-7)-LmUSP (8-12)-EF in A549 cells along with GAL4CfEcR-CDEF and pFRLuc in the presence of non-steroid (GSE) ligand.

The same chimeric RXR- and parent RXR-based switches were also examined in a human lung carcinoma cell line A549 (ATCC) and similar results were observed (FIG. 3).

Thus, Applicants have demonstrated for the first time that a chimeric RXR ligand binding domain can function effectively in partnership with an ecdysone receptor in an inducible gene expression system in mammalian cells. Surprisingly, the EcR/chimeric RXR-based inducible gene expression system of the present invention is an improvement over both the EcR/vertebrate RXR- and EcR/invertebrate RXR-based gene expression modulation systems since less ligand is required for transactivation and increased levels of transactivation can be achieved.

Based upon Applicant's discovery described herein, one of ordinary skill in the art is able to predict that other chimeric RXR ligand binding domain comprising at least two different species RXR polypeptide fragments from a vertebrate RXR LBD, an invertebrate RXR LBD, or a non-Dipteran and non-Lepidopteran invertebrate RXR homolog will also function in Applicants' EcR/chimeric RXR-based inducible gene expression system. Based upon Applicants' invention, the means to make additional chimeric RXR LBD embodiments within the scope of the present invention is within the art and no undue experimentation is necessary. Indeed, one of skill in the art can routinely clone and sequence a polynucleotide encoding a vertebrate or invertebrate RXR or RXR homolog LBD, and based upon sequence homology analyses similar to that presented in FIG. 4, and determine the corresponding polynucleotide and polypeptide fragments of that particular species RXR LBD that are encompassed within the scope of the present invention.

One of ordinary skill in the art is also able to predict that Applicants' novel inducible gene expression system will also work to modulate gene expression in yeast cells. Since the Dipteran RXR homolog/and Lepidopteran RXR homolog/EcR-based gene expression systems function constitutively in yeast cells (data not shown), similar to how they function in mammalian cells, and non-Dipteran and non-Lepidopteran invertebrate RXRs function inducibly in partnership with an EcR in mammalian cells, the EcR/chimeric RXR-based inducible gene expression modulation system is predicted to function inducibly in yeast cells, similar to how it functions in mammalian cells. Thus, the EcR/chimeric RXR inducible gene expression system of the present invention is useful in applications where modulation of gene expression levels is desired in both yeast and mammalian cells. Furthermore, Applicants' invention is also contemplated to work in other cells, including but not limited to bacterial cells, fungal cells, and animal cells.

Example 3

There are six amino acids in the C-terminal end of the LBD that are different between MmRXRα and LmUSP (see sequence alignments presented in FIG. 4). To verify if these six amino acids contribute to the differences observed between MmRXRα and LmUSP transactivation abilities, Applicants constructed RXR chimeras in which the C-terminal six amino acids, designated herein as the F domain, of one parent RXR were substituted for the F domain of the other parent RXR. Gene switches comprising LmUSP-EF fused to MmRXRα-F (VP16/LmUSP-EF-MmRXRα-F, switch 1.6), MmRXRα-EF fused to LmUSP-F (VP16/MmRXRαEF-LmUSP-F, switch 1.5), and MmRXRα-EF(1-7)-LmUSP-EF (8-12) fused to a MmRXRα-F (Chimera/RXR-F, switch 1.4) were constructed as described in Example 1. These constructs were transfected in NIH3T3 cells and transactivation potential was assayed in the presence of 0, 0.2, 1, and 10 μM N-(2-ethyl-3-methoxybenzoyl)N'-(3,5-dimethylbenzoyl)-N'-tert-butylhydrazine non-steroidal ligand. The F-domain chimeras (gene switches 1.4-1.6) were compared to the MmRXRα-EF(1-7)-LmUSP-EF(8-12) chimeric RXR LBD of gene switch 1.3. Plasmid pFRLUC (Stratagene) encoding a luciferase polypeptide was used as a reporter gene construct and pTKRL (Promega) encoding a *Renilla* luciferase polypeptide under the control of the constitutive TK promoter was used to normalize the transfections as described above. The cells were harvested, lysed and luciferase reporter activity was measured in the cell lysates. Total fly luciferase relative light units are presented. The number on the top of each bar is the maximum fold induction for that treatment. The analysis was performed in triplicate and mean luciferase counts [total relative light units (RLU)] were determined as described above.

Figure 5:
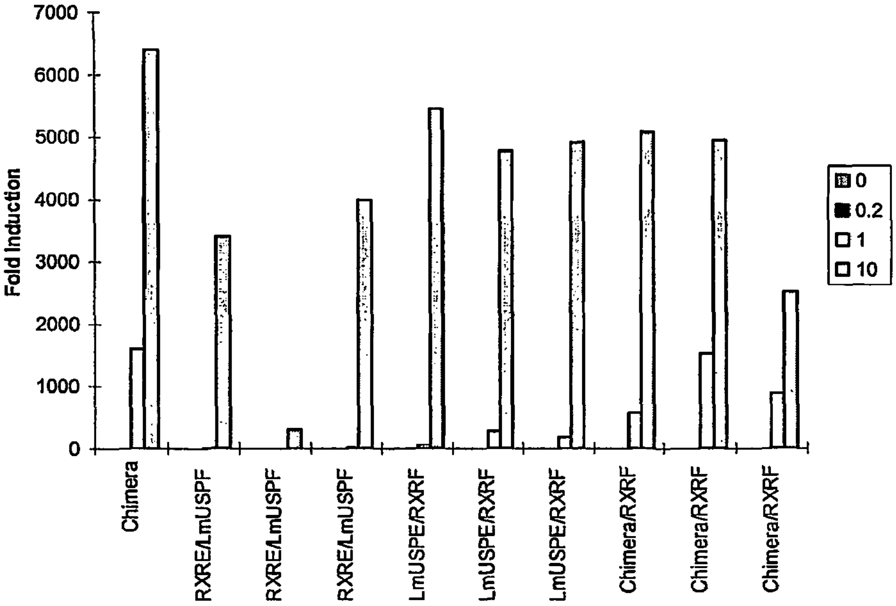
FIG. 5: Expression data of GAL4CfEcR-CDEF/VP16chimeric RXR-based gene switches 1.3-1.6 in NIH3T3 cells along with pFRLuc in the presence of non-steroid (GSE) ligand.

As shown in FIG. 5, the six amino acids in the C-terminal end of the LBD (F domain) do not appear to account for the differences observed between vertebrate RXR and invertebrate RXR transactivation abilities, suggesting that helices 8-12 of the EF domain are most likely responsible for these differences between vertebrate and invertebrate RXRs.

Example 4

This Example describes the construction of four EcR-DEF-based gene switches comprising the DEF domains from *Choristoneura fumiferana* (Lepidoptera), *Drosophila melanogaster* (Diptera), *Tenebrio molitor* (Coleoptera), and *Amblyomma americanum* (Ixodidae) fused to a GAL4 DNA binding domain. In addition, the EF domains of vertebrate RXRs, invertebrate RXRs, or invertebrate USPs from *Choristoneura fumiferana* USP, *Drosophila melanogaster* USP, *Locusta migratoria* USP (Orthoptera), *Mus musculus* RXRα (Vertebrata), a chimera between MmRXRα and LmUSP (Chimera; of switch 1.13), *Amblyomma americanum* RXR homolog 1 (Ixodidae), *Amblyomma americanum* RXR homolog 2 (Ixodidae) were fused to a VP16 activation domain. The receptor combinations were compared for their ability to transactivate the reporter plasmid pFRLuc in mouse NIH3T3 cells in the presence of 0, 0.2, 1, or 10 μM PonA steroidal ligand (Sigma Chemical Company) or 0, 0.04, 0.2, 1, or 10 μM N-(2-ethyl-3-methoxybenzoyl)N'-(3,5-dimethylbenzoyl)-N'-tert-butylhydrazine non-steroidal ligand as described above. The cells were harvested, lysed and luciferase reporter activity was measured in the cell lysates. Total fly luciferase relative light units are presented. The number on the top of each bar is the maximum fold induction for that treatment. The analysis was performed in triplicate and mean luciferase counts [total relative light units (RLU)] were determined as described above.

Figure 6:
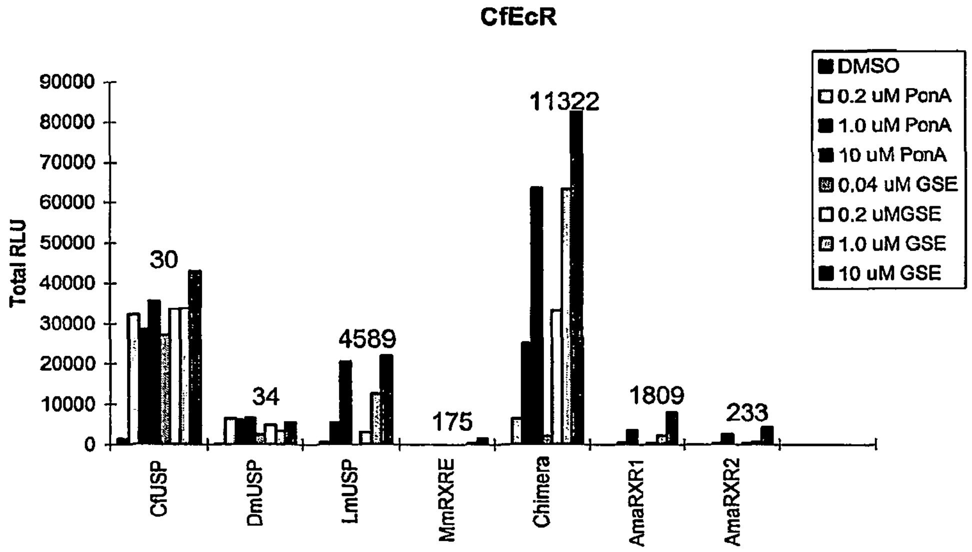
FIG. 6: Expression data of gene switches comprising the DEF domains of EcRs from CfEcR, DmEcR, TmEcR, or AmaEcR fused to GAL4 DNA binding domain and the EF domains of RXR/USPs from CfUSP, DmUSP, LmUSP, MmRXRα, a chimera between MmRXRα and LmUSP (Chimera), AmaRXR1, or AmaRXR2 fused to a VP 16 activation domain along with pFRLuc in NIH3T3 cells in the presence of steroid (PonA) or non-steroid (GSE) ligand. The different RXR/USP constructs were compared in partnership with GAL4CfEcR-DEF.
Figure 7:
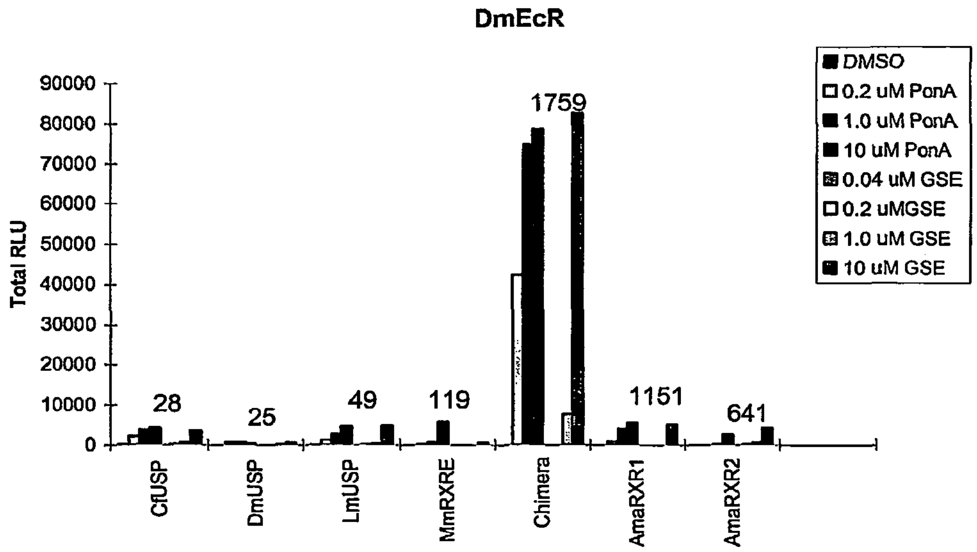
FIG. 7: Expression data of gene switches comprising the DEF domains of EcRs from CfEcR, DmEcR, TmEcR, or AmaEcR fused to GAL4 DNA binding domain and the EF domains of RXR/USPs from CfUSP, DmUSP, LmUSP, MmRXRα, a chimera between MmRXRα and LmUSP (Chimera), AmaRXR1, or AmaRXR2 fused to a VP16 activation domain along with pFRLuc in NIH3T3 cells in the presence of steroid (PonA) or non-steroid (GSE) ligand. The different RXR/USP constructs were compared in partnership with GAL4DmEcR-DEF.
Figure 8:
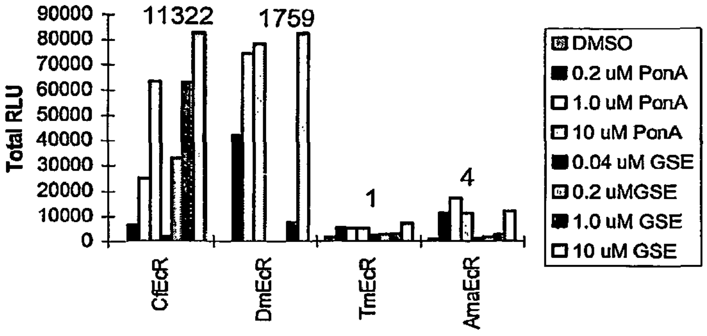
FIG. 8: Expression data of gene switches comprising the DEF domains of EcRs from CfEcR, DmEcR, TmEcR, or AmaEcR fused to GAL4 DNA binding domain and the EF domains of RXR/USPs from CfUSP, DmUSP, LmUSP, MmRXRα, a chimera between MmRXRα and LmUSP (Chimera), AmaRXR1, or AmaRXR2 fused to a VP16 activation domain along with pFRLuc in NIH3T3 cells in the presence of steroid (PonA) or non-steroid (GSE) ligand. The different EcR constructs were compared in partnership with a chimeric RXR-EF (MmRXRα(1-7)-LmUSP(8-12)-EF).

FIGS. 6-8 show the results of these analyses. The MmRXR-LmUSP chimera was the best partner for CfEcR (11,000 fold induction, FIG. 6), DmEcR (1759 fold induction, FIG. 7). For all other EcRs tested, the RXR chimera produced higher background levels in the absence of ligand (see FIG. 8). The CfEcR/chimeric RXR-based switch (switch 1.13) was more sensitive to non-steroid than PonA whereas, the DmEcR/chimeric RXR-based switch (switch 1.20) was more sensitive to PonA than non-steroid. Since these two switch formats produce decent levels of induction and show differential sensitivity to steroids and non-steroids, these may be exploited for applications in which two or more gene switches are desired.

Except for CfEcR, all other EcRs tested in partnership the chimeric RXR are more sensitive to steroids than to non-steroids. The TmEcR/chimeric RXR-based switch (switch 1.21; FIG. 8) is more sensitive to PonA and less sensitive to non-steroid and works best when partnered with either MmRXRα, AmaRXR1, or AmaRXR2. The AmaEcR/chimeric RXR-based switch (switch 1.22; FIG. 8) is also more sensitive to PonA and less sensitive to non-steroid and works best when partnered with either an LmUSP, MmRXR, AmaRXR1 or AmaRXR2-based gene expression cassette. Thus, TmEcR/ and AmaEcR/chimeric RXR-based gene switches appear to form a group of ecdysone receptors that is different from lepidopteran and dipteran EcR/chimeric RXR-based gene switches group (CfEcR/chimeric RXR and DmEcR/chimeric RXR, respectively). As noted above, the differential ligand sensitivities of Applicants' EcR/chimeric RXR-based gene switches are advantageous for use in applications in which two or more gene switches are desired.

Example 5

This Example describes Applicants' further analysis of gene expression cassettes encoding various chimeric RXR polypeptides comprising a mouse RXRα isoform polypeptide fragment or a human RXRβ isoform polypeptide fragment and an LmUSP polypeptide fragment in mouse NIH3T3 cells. These RXR chimeras were constructed in an effort to identify the helix or helices of the EF domain that account for the observed transactivational differences between vertebrate and invertebrate RXRs. Briefly, five different gene expression cassettes encoding a chimeric RXR ligand binding domain were constructed as described in Example 1. The five chimeric RXR ligand binding domains encoded by these gene expression cassettes and the respective vertebrate RXR and invertebrate RXR fragments they comprise are depicted in Table 1.

TABLE 1

HsRXRβ/LmUSP EF Domain Chimeric RXRs

| Chimera Name | HsRXRβ-EF Polypeptide Fragment(s) | LmUSP-EF Polypeptide Fragment(s) |
|---|---|---|
| β Chimera #6 | Helices 1-6 | Helices 7-12 |
| β Chimera #8 | Helices 1-7 | Helices 8-12 |
| β Chimera #9 | Helices 1-8 | Helices 9-12 |
| β Chimera #10 | Helices 1-9 | Helices 10-12 |
| β Chimera #11 | Helices 1-10 | Helices 11-12 |

Figure 9:
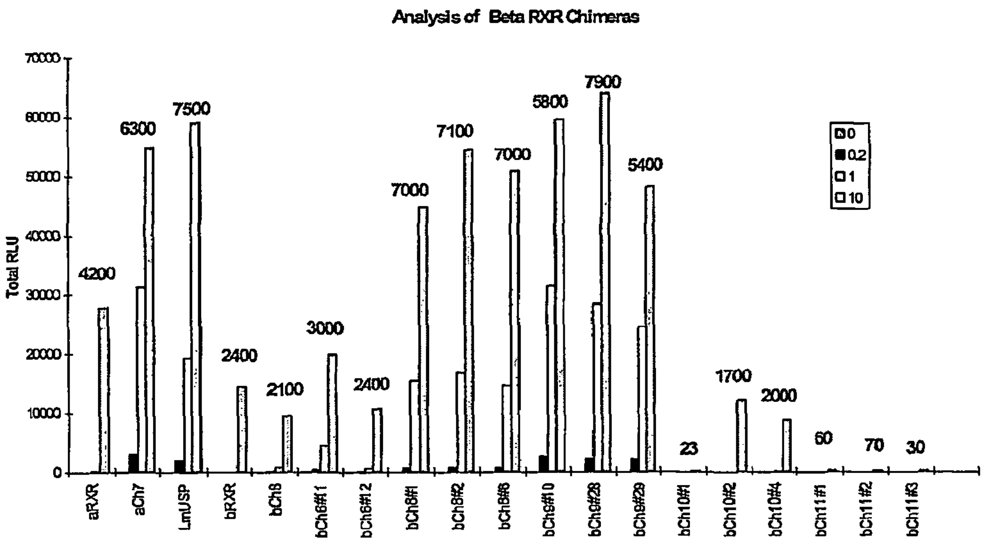
FIG. 9: Expression data of VP16/MmRXRα-EF (aRXR), VP16/Chimera between MmRXRα-EF and LmUSP-EF (MmRXRα(1-7)-LmUSP(8-12)-EF; aCh7), VP16/LmUSP-EF (LmUSP) and three independent clones from each of five VP16/chimeras between HsRXRβ-EF and LmUSP-EF (see Table 1 for chimeric RXR constructs; bRXRCh6, bRXRCh8, bRXRCh9, bRXRCh10, and bRXRCh11) were transfected into NIH3T3 cells along with GAL4/CfEcR-DEF and pFRLuc. The transfected cells were grown in the presence of 0, 0.2, 1 and 10 μM non-steroidal ligand (GSE). The reporter activity was quantified 48 hours after adding ligands.
Figure 10:
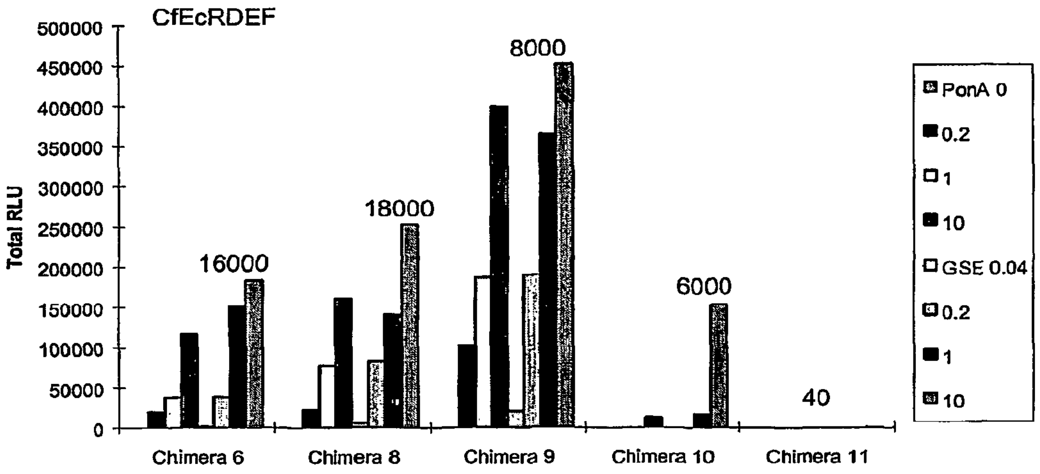
FIG. 10: Expression data of VP16/MmRXRα-EF (aRXR), VP16/Chimera between MmRXRα-EF and LmUSP-EF (MmRXRα-(1-7)-LmUSP(8-12)-EF; aCh7), VP16/LmUSP-EF (LmUSP) and three independent clones from each of five VP16/chimeras between HsRXRβ-EF and LmUSP-EF (see Table 1 for chimeric RXR constructs; bRXRCh6, bRXRCh8, bRXRCh9, bRXRCh10, and bRXRCh11) were transfected into NIH3T3 cells along with GAL4/CfEcR-DEF and pFRLuc. The transfected cells were grown in the presence of 0, 0.2, 1 and 10 μM steroid ligand (PonA) or 0, 0.04, 0.2, 1, and 10 μM non-steroidal ligand (GSE). The reporter activity was quantified 48 hours after adding ligands.
Figure 11:
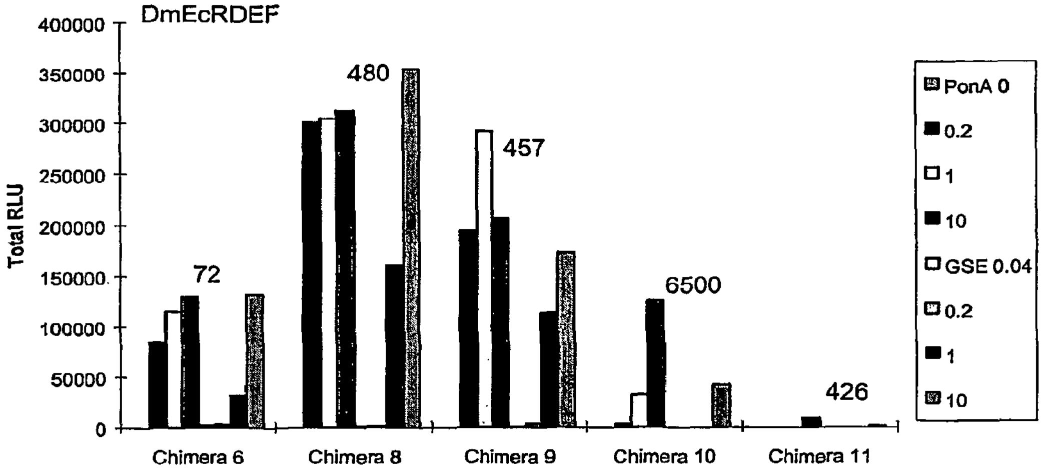
FIG. 11: Expression data of VP16/MmRXRα-EF (aRXR), VP16/Chimera between MmRXRα-EF and LmUSP-EF (MmRXRα-(1-7)-LmUSP(8-12)-EF; aCh7), VP16/LmUSP-EF (LmUSP) and three independent clones from each of five VP16/chimeras between HsRXRβ-EF and LmUSP-EF (see Table 1 for chimeric RXR constructs; bRXRCh6, bRXRCh8, bRXRCh9, bRXRCh10, and bRXRCh11) were transfected into NIH3T3 cells along with GAL4/DmEcR-DEF and pFRLuc. The transfected cells were grown in the presence of 0, 0.2, 1 and 10 μM steroid ligand (PonA) or 0, 0.04, 0.2, 1, and 10 μM non-steroidal ligand (GSE). The reporter activity was quantified 48 hours after adding ligands.

Three individual clones of each chimeric RXR LBD of Table 1 were transfected into mouse NIH3T3 cells along with either GAL4CfEcR-DEF (switches 1.25-1.29 of Example 1; FIGS. 9 and 10) or GAL4DmEcR-DEF (switches 1.30-1.34 of Example 1; FIG. 11) and the reporter plasmid pFRLuc as described above. The transfected cells were cultured in the presence of either a) 0, 0.2, 1, or 10 μM non-steroidal ligand (FIG. 9), or b) 0, 0.2, 1, or 10 μM steroid ligand PonA or 0, 0.4, 0.2, 1, or 10 μM non-steroid ligand (FIGS. 10 and 11) for 48 hours. The reporter gene activity was measured and total RLU are shown. The number on top of each bar is the maximum fold induction for that treatment and is the mean of three replicates.

As shown in FIG. 9, the best results were obtained when an HsRXRβH1-8 and LmUSP H9-12 chimeric RXR ligand binding domain (of switch 1.27) was used, indicating that helix 9 of LmUSP may be responsible for sensitivity and magnitude of induction.

Using CfEcR as a partner, chimera 9 demonstrated maximum induction (see FIG. 10). Chimeras 6 and 8 also produced good induction and lower background, as a result the fold induction was higher for these two chimeras when compared to chimera 9. Chimeras 10 and 11 produced lower levels of reporter activity.

Using DmEcR as a partner, chimera 8 produced the reporter activity (see FIG. 11). Chimera 9 also performed well, whereas chimeras 6, 10 and 11 demonstrated lower levels of reporter activity.

The selection of a particular chimeric RXR ligand binding domain can also influence the performance EcR in response to a particular ligand. Specifically, CfEcR in combination with chimera 11 responded well to non-steroid but not to PonA (see FIG. 10). Conversely, DmEcR in combination with chimera 11 responded well to PonA but not to non-steroid (see FIG. 11).

Example 6

This Example demonstrates the effect of introduction of a second ligand into the host cell comprising an EcR/chimeric RXR-based inducible gene expression modulation system of the invention. In particular, Applicants have determined the effect of 9-cis-retinoic acid on the transactivation potential of the GAL4CfEcR-DEF/VP16HsRXRβ-(1-8)-LmUSP-(9-12)-EF (βchimera 9; switch 1.27) gene switch along with pFRLuc in NIH 3T3 cells in the presence of non-steroid (GSE) for 48 hours.

Briefly, GAL4CfEcR-DEF, pFRLuc and VP16HsRXRβ-(1-8)-LmUSP-(9-12)-EF (chimera #9) were transfected into NIH3T3 cells and the transfected cells were treated with 0, 0.04, 0.2, 1, 5 and 25 μM non-steroidal ligand (GSE) and 0, 1, 5 and 25 μM 9-cis-retinoic acid (Sigma Chemical Company). The reporter activity was measured at 48 hours after adding ligands.

Figure 12:
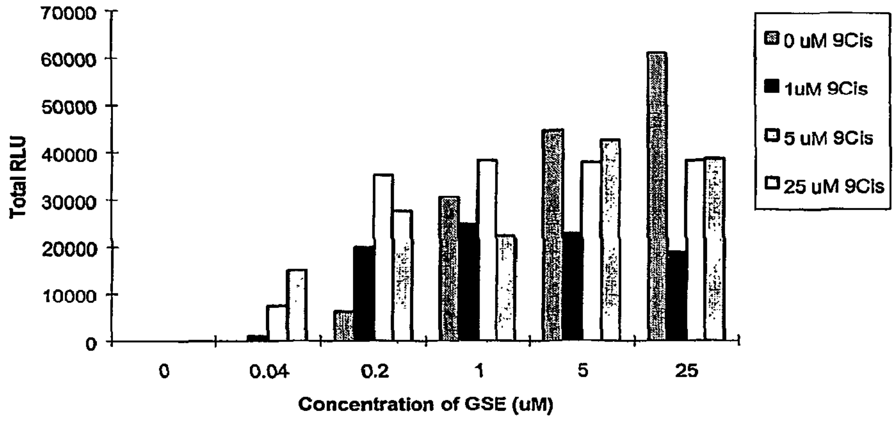
FIG. 12: Effect of 9-cis-retinoic acid on transactivation potential of the GAL4CfEcR-DEF/VP16HsRXRβ-(1-8)-LmUSP-(9-12)-EF (βchimera 9) gene switch along with pFRLuc in NIH 3T3 cells in the presence of non-steroid (GSE) and 9-cis-retinoic acid (9Cis) for 48 hours.

As shown in FIG. 12, the presence of retinoic acid increased the sensitivity of CfEcR-DEF to non-steroidal ligand. At a non-steroid ligand concentration of 0.04 μM, there is very little induction in the absence of 9-cis-retinoic acid, but when 1 μM 9-cis-retinoic acid is added in addition to 0.04 μM non-steroid, induction is greatly increased.

The invention claimed is:

1. A transgenic, non-human organism comprising a gene expression modulation system comprising:

a) a first gene expression cassette that is capable of being expressed in said organism comprising a polynucleotide sequence that encodes a first hybrid polypeptide comprising:

i) a DNA-binding domain that recognizes a response element associated with a gene whose expression is to be modulated; and ii) an ecdysone receptor ligand binding domain; and b) a second gene expression cassette that is capable of being expressed in said organism comprising a polynucleotide sequence that encodes a second hybrid polypeptide comprising:

i) a transactivation domain; and ii) a chimeric retinoid X receptor ligand binding domain comprising a vertebrate retinoid X receptor amino acid sequence and an invertebrate retinoid X receptor amino acid sequence, wherein at least one alpha helix of said vertebrate retinoid X receptor ligand binding domain is replaced with the same number of alpha helices from an invertebrate retinoid X receptor ligand binding domain or the same number of alpha helices from an ultraspiracle (USP) receptor ligand binding domain, wherein the genome of said non-human organism comprises said gene expression modulation system, and wherein said system modulates the expression of said gene.

2. The transgenic, non-human organism according to claim 1, wherein the non-human organism is selected from the group consisting of a bacterium, a fungus, and a yeast.

3. The transgenic, non-human organism according to claim 2, wherein said organism is a yeast selected from the group consisting of an *Aspergillus*, a *Trichoderma*, a *Saccharomyces*, a *Pichia*, a *Candida*, and a *Hansenula.*

4. The transgenic, non-human organism according to claim 2, wherein said organism is selected from the group consisting of a *Synechocystis*, a *Synechococcus*, a *Salmonella*, a *Bacillus*, an *Acinetobacter*, a *Rhodococcus*, a *Streptomyces*, an *Escherichia*, a *Pseudomonas*, a *Methylomonas*, a *Methylobacter*, an *Alcaligenes*, an *Anabaena*, a *Thiobacillus*, a *Methanobacterium*, and a *Klebsiella.*

5. The transgenic, non-human organism according to claim 1, wherein the organism is a mouse.

6. The transgenic, non-human organism according to claim 1, wherein the ecdysone receptor ligand binding domain is a *Choristoneura fumiferana* ecdysone receptor ligand binding domain or a *Drosophila melanogaster* ecdysone receptor ligand binding domain.

7. The transgenic, non-human organism according to claim 1, further comprising a third gene expression cassette comprising:

(a) a response element recognized by the DNA-binding domain of the first hybrid polypeptide;

(b) a promoter that is activated by the transactivation domain of the second hybrid polypeptide; and (c) a gene whose expression is to be modulated.

8. The transgenic, non-human organism according to claim 1, wherein the invertebrate retinoid X receptor amino acid sequence is non-Dipteran/non-Lepidopteran invertebrate retinoid X receptor amino acid sequence.

9. The transgenic, non-human organism according to claim 1, wherein the chimeric retinoid X receptor ligand binding domain of the second hybrid polypeptide is encoded by a polynucleotide comprising a nucleic acid sequence selected from the group consisting of a) nucleotides 1-348 of SEQ ID NO: 13 and nucleotides 268-630 of SEQ ID NO: 21, b) nucleotides 1-408 of SEQ ID NO: 13 and nucleotides 337-630 of SEQ ID NO: 21, c) nucleotides 1-465 of SEQ ID NO: 13 and nucleotides 403-630 of SEQ ID NO: 21, d) nucleotides 1-555 of SEQ ID NO: 13 and nucleotides 490-630 of SEQ ID NO: 21, e) nucleotides 1-624 of SEQ ID NO: 13 and nucleotides 547-630 of SEQ ID NO: 21, f) nucleotides 1-645 of SEQ ID NO: 13 and nucleotides 601-630 of SEQ ID NO: 21, and g) nucleotides 1-717 of SEQ ID NO: 13 and nucleotides 613-630 of SEQ ID NO: 21.

10. The transgenic, non-human organism according to claim 1, wherein the chimeric retinoid X receptor ligand binding domain of the second hybrid polypeptide comprises an amino acid sequence selected from the group consisting of a) amino acids 1-116 of SEQ ID NO: 19 and amino acids 90-210 of SEQ ID NO: 27, b) amino acids 1-136 of SEQ ID NO: 19 and amino acids 113-210 of SEQ ID NO: 27, c) amino acids 1-155 of SEQ ID NO: 19 and amino acids 135-210 of SEQ ID NO: 27, d) amino acids 1-185 of SEQ ID NO: 19 and amino acids 164-210 of SEQ ID NO: 27, e) amino acids 1-208 of SEQ ID NO: 19 and amino acids 183-210 of SEQ ID NO: 27, f) amino acids 1-215 of SEQ ID NO: 19 and amino acids 201-210 of SEQ ID NO: 27, and g) amino acids 1-239 of SEQ ID NO: 19 and amino acids 205-210 of SEQ ID NO: 27.

11. The transgenic, non-human organism according to claim 1, wherein the DNA-binding domain is selected from a GAL4 DNA-binding domain and a LexA DNA-binding domain.

12. The method transgenic, non-human organism of claim 1, wherein the transactivation domain is selected from the group consisting of an a VP16 transactivation domain, a B42 acidic activator transactivation domain, a steroid/thyroid hormone nuclear receptor transactivation domain, a polyglutamine transactivation domain, a basic or acidic amino acid transactivation domain, a GAL4 transactivation domain, an NF-κB transactivation domain, and a BP64 transactivation domain.

13. The transgenic, non-human organism according to claim 1, wherein said ecdysone receptor ligand binding domain is selected from the group consisting of an invertebrate ecdysone receptor ligand binding domain, an Arthropod ecdysone receptor ligand binding domain, a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm *Choristoneura fumiferana* ecdysone receptor ligand binding domain, a beetle *Tenebrio molitor* ecdysone receptor ligand binding domain, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain and a leafhopper *Nephotetix cincticeps* ecdysone receptor ligand binding domain.

14. The transgenic, non-human organism according to claim 1, wherein said gene expression modulation system is contained in a vector.

15. The transgenic, non-human organism according to claim 14, wherein said vector is selected from the group consisting of a retrovirus vector, an adeno-associated virus vector, a pox virus vector, a baculovirus vector, a vaccinia virus vector, a herpes simplex virus vector, an Epstein-Barr virus vector, a geminivirus vector, a caulimovirus vector, and an adenovirus vector.

16. The transgenic, non-human organism according to claim 1, wherein said organism is an animal.

17. The transgenic, non-human organism according to claim 16, wherein said animal is a mammal.

18. The transgenic, non-human organism according to claim 1, wherein said mammal is selected from the group consisting of:

a) a rat;

b) a rabbit;

c) a cat;

d) a dog;

e) a bovine;

f) a goat;

g) a pig;

h) a horse;

i) a sheep;

j) a monkey; and, k) a chimpanzee.

19. A transgenic, non-human organism comprising a gene expression modulation system comprising:

a) a first gene expression cassette that is capable of being expressed in said organism comprising a polynucleotide sequence that encodes a first hybrid polypeptide comprising:

i) a DNA-binding domain that recognizes a response element associated with a gene whose expression is to be modulated; and ii) a chimeric retinoid X receptor ligand binding domain comprising a vertebrate retinoid X receptor amino acid sequence and an invertebrate retinoid X receptor amino acid sequence, wherein at least one alpha helix of said vertebrate retinoid X receptor ligand binding domain is replaced with the same number of alpha helices from an invertebrate retinoid X receptor ligand binding domain or the same number of alpha helices from an ultraspiracle USP receptor ligand binding domain; and b) a second gene expression cassette that is capable of being expressed in said organism comprising a polynucleotide sequence that encodes a second hybrid polypeptide comprising:

i) a transactivation domain; and ii) an ecdysone receptor ligand binding domain, wherein the genome of said non-human organism comprises said gene expression modulation system, and wherein said system modulates the expression of said gene.

20. The transgenic, non-human organism according to claim 19, wherein the non-human organism is selected from the group consisting of a bacterium, a fungus, and a yeast.

21. The transgenic, non-human organism according to claim 20, wherein said organism is a yeast selected from the group consisting of an *Aspergillus*, a *Trichoderma*, a *Saccharomyces*, a *Pichia*, a *Candida*, and a *Hansenula*.

22. The transgenic, non-human organism according to claim 20, wherein said organism is selected from the group consisting of a *Synechocystis*, a *Synechococcus*, a *Salmonella*, a *Bacillus*, an *Acinetobacter*, a *Rhodococcus*, a *Streptomyces*, an *Escherichia*, a *Pseudomonas*, a *Methylomonas*, a *Methylobacter*, an *Alcaligenes*, an *Anabaena*, a *Thiobacillus*, a *Methanobacterium*, and a *Klebsiella*.

23. The transgenic, non-human organism according to claim 19, wherein the organism is a mouse.

24. The transgenic, non-human organism according to claim 19, wherein the ecdysone receptor ligand binding domain is a *Choristoneura fumiferana* ecdysone receptor ligand binding domain or a *Drosophila melanogaster* ecdysone receptor ligand binding domain.

25. The transgenic, non-human organism according to claim 19, further comprising a third gene expression cassette comprising:

(a) a response element recognized by the DNA-binding domain of the first hybrid polypeptide;
(b) a promoter that is activated by the transactivation domain of the second hybrid polypeptide; and
(c) a gene whose expression is to be modulated.

26. The transgenic, non-human organism according to claim 19, wherein the invertebrate retinoid X receptor amino acid sequence is non-Dipteran/non-Lepidopteran invertebrate retinoid X receptor amino acid sequence.

27. The transgenic, non-human organism according to claim 19, wherein the chimeric retinoid X receptor ligand binding domain of the first hybrid polypeptide is encoded by a polynucleotide comprising a nucleic acid sequence selected from the group consisting of a) nucleotides 1-348 of SEQ ID NO: 13 and nucleotides 268-630 of SEQ ID NO: 21,
b) nucleotides 1-408 of SEQ ID NO: 13 and nucleotides 337-630 of SEQ ID NO: 21,
c) nucleotides 1-465 of SEQ ID NO: 13 and nucleotides 403-630 of SEQ ID NO: 21,
d) nucleotides 1-555 of SEQ ID NO: 13 and nucleotides 490-630 of SEQ ID NO: 21,
e) nucleotides 1-624 of SEQ ID NO: 13 and nucleotides 547-630 of SEQ ID NO: 21,
f) nucleotides 1-645 of SEQ ID NO: 13 and nucleotides 601-630 of SEQ ID NO: 21, and
g) nucleotides 1-717 of SEQ ID NO: 13 and nucleotides 613-630 of SEQ ID NO: 21.

28. The transgenic, non-human organism according to claim 19, wherein the chimeric retinoid X receptor ligand binding domain of the first hybrid polypeptide comprises an amino acid sequence selected from the group consisting of a) amino acids 1-116 of SEQ ID NO: 19 and amino acids 90-210 of SEQ ID NO: 27,
b) amino acids 1-136 of SEQ ID NO: 19 and amino acids 113-210 of SEQ ID NO: 27,
c) amino acids 1-155 of SEQ ID NO: 19 and amino acids 135-210 of SEQ ID NO: 27,
d) amino acids 1-185 of SEQ ID NO: 19 and amino acids 164-210 of SEQ ID NO: 27,
e) amino acids 1-208 of SEQ ID NO: 19 and amino acids 183-210 of SEQ ID NO: 27,
f) amino acids 1-215 of SEQ ID NO: 19 and amino acids 201-210 of SEQ ID NO: 27, and
g) amino acids 1-239 of SEQ ID NO: 19 and amino acids 205-210 of SEQ ID NO: 27.

29. The transgenic, non-human organism according to claim 19, wherein the DNA-binding domain is selected from a GAL4 DNA-binding domain and a LexA DNA-binding domain.

30. The transgenic, non-human organism of claim 19, wherein the transactivation domain is selected from the group consisting of an a VP16 transactivation domain, a B42 acidic activator transactivation domain, a steroid/thyroid hormone nuclear receptor transactivation domain, a polyglutamine transactivation domain, a basic or acidic amino acid transactivation domain, a GAL4 transactivation domain, an NF-κB transactivation domain, and a BP64 transactivation domain.

31. The transgenic, non-human organism according to claim 19, wherein said ecdysone receptor ligand binding domain is selected from the group consisting of an invertebrate ecdysone receptor ligand binding domain, an Arthropod ecdysone receptor ligand binding domain, a Lepidopteran ecdysone receptor ligand binding domain, a Dipteran ecdysone receptor ligand binding domain, an Orthopteran ecdysone receptor ligand binding domain, a Homopteran ecdysone receptor ligand binding domain, a Hemipteran ecdysone receptor ligand binding domain, a spruce budworm *Choristoneura fumiferana* ecdysone receptor ligand binding domain, a beetle *Tenebrio molitor* ecdysone receptor ligand binding domain, a *Manduca sexta* ecdysone receptor ligand binding domain, a *Heliothies virescens* ecdysone receptor ligand binding domain, a midge *Chironomus tentans* ecdysone receptor ligand binding domain, a silk moth *Bombyx mori* ecdysone receptor ligand binding domain, a squinting bush brown *Bicyclus anynana* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a blowfly *Lucilia cuprina* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Celuca pugilator* ecdysone receptor ligand binding domain, an ixodid tick *Amblyomma americanum* ecdysone receptor ligand binding domain, a whitefly *Bamecia argentifoli* ecdysone receptor ligand binding domain and a leafhopper *Nephotetix cincticeps* ecdysone receptor ligand binding domain.

32. The transgenic, non-human organism according to claim 19, wherein said gene expression modulation system is contained in a vector.

33. The transgenic, non-human organism according to claim 32, wherein said vector is selected from the group consisting of a retrovirus vector, an adeno-associated virus vector, a pox virus vector, a baculovirus vector, a vaccinia virus vector, a herpes simplex virus vector, an Epstein-Barr virus vector, a geminivirus vector, a caulimovirus vector, and an adenovirus vector.

34. The transgenic, non-human organism according to claim 19, wherein said organism is an animal.

35. The transgenic, non-human organism according to claim 19, wherein said animal is a mammal.

36. The transgenic, non-human organism according to claim 19, wherein said mammal is selected from the group consisting of:

a) a rat;
b) a rabbit;
c) a cat;
d) a dog;
e) a bovine;
f) a goat;

g) a pig;

h) a horse;

i) a sheep;

j) a monkey; and, k) a chimpanzee.

* * * * *

UNITED STATES PATENT AND TRADEMARK OFFICE

CERTIFICATE OF CORRECTION

PATENT NO. : 8,598,409 B2
APPLICATION NO. : 11/841648
DATED : December 3, 2013
INVENTOR(S) : Kapitskaya et al.

It is certified that error appears in the above-identified patent and that said Letters Patent is hereby corrected as shown below:

In the Claims

Column 133

Line 35, please replace "The method transgenic" with --The transgenic--

Signed and Sealed this
Twenty-eighth Day of October, 2014

Michelle K. Lee

Michelle K. Lee
*Deputy Director of the United States Patent and Trademark Office*